(12) United States Patent
Zhang et al.

(10) Patent No.: US 9,611,235 B2
(45) Date of Patent: Apr. 4, 2017

(54) METHODS AND COMPOSITIONS RELATED TO A RETINOID RECEPTOR-SELECTIVE PATHWAY

(75) Inventors: Xiao-kun Zhang, San Diego, CA (US); Ying Su, San Diego, CA (US); Hu Zhou, San Diego, CA (US); Wen Liu, La Jolla, CA (US); Pei-Qiang Huang, Xiamen (CN)

(73) Assignees: SANFORD-BURNHAM MEDICAL RESEARCH INSTITUTE, La Jolla, CA (US); XIAMEN UNIVERSITY, Xiamen, Fujian (CN)

( * ) Notice: Subject to any disclaimer, the term of this patent is extended or adjusted under 35 U.S.C. 154(b) by 997 days.

(21) Appl. No.: 13/102,475

(22) Filed: May 6, 2011

(65) Prior Publication Data

US 2015/0266842 A1    Sep. 24, 2015

Related U.S. Application Data

(60) Provisional application No. 61/332,124, filed on May 6, 2010.

(51) Int. Cl.

| C07D 295/112 | (2006.01) |
| A61K 38/19 | (2006.01) |
| C07C 57/62 | (2006.01) |
| C07C 59/72 | (2006.01) |
| C07C 255/57 | (2006.01) |
| C07D 213/55 | (2006.01) |
| G01N 33/50 | (2006.01) |

(52) U.S. Cl.
CPC ........ *C07D 295/112* (2013.01); *A61K 38/191* (2013.01); *C07C 57/62* (2013.01); *C07C 59/72* (2013.01); *C07C 255/57* (2013.01); *C07D 213/55* (2013.01); *G01N 33/5011* (2013.01); *G01N 2333/70567* (2013.01); *G01N 2510/00* (2013.01)

(58) Field of Classification Search
None
See application file for complete search history.

(56) References Cited

U.S. PATENT DOCUMENTS

| 2005/0054008 A1 | 3/2005 | Zhang et al. |
| 2006/0235080 A1 | 10/2006 | Weissbach et al. |

FOREIGN PATENT DOCUMENTS

| CN | 102030642 A | 4/2011 |
| DE | 10163426 A1 | 7/2003 |
| DE | 10163426 A1 | 7/2003 |
| JP | 2005-247807 | 9/2005 |
| WO | WO 01/12858 A1 | 2/2001 |
| WO | WO 2004047772 A2 * | 6/2004 |
| WO | WO-2011140525 A2 | 11/2011 |
| WO | WO-2015100267 A1 | 7/2015 |

OTHER PUBLICATIONS

Felts et al., Sulindac Derivatives that Activate teh Peroxisome Proliferator-activated Receptor gamma but Lack Cyclooxygenase Inhibition, 2008, J. Med. Chem., vol. 51, pp. 4911-4919.*
Baldwin et al., Structural requirements for the binding of non-steroidal anti-inflammatory drugs to the 78 kDa gastrin binding protein, 1999, Biochimica et Biophysica Acta, 1428, pp. 68-76.*
Baldwin, et al; Structural requirements for the binding of non-steroidal anti-inflammatory drugs to the 78 kDa gastrin binding protein; Biochim Biophys Acta. Jun. 28, 1999;1428(1):68-76.
Felts, et al; Sulindac derivatives that activate the peroxisome proliferator-activated receptor gamma but lack cyclooxygenase inhibition; J Med Chem. Aug. 28, 2008;51(16):4911-9. doi: 10.1021/jm700969c. Epub Jul. 30, 2008.
Keller, et al; Change in apoptosis in patients treated with sulindac; Gastroenterology. Apr. 15, 1998, col. 114, p. A620.
Masunaga, et al; Sulindac inhibits growth of rat colon carcinoma by inducing apoptosis.; Eur Surg Res. 2000;32(5):305-9.
Zhou, et al; NSAID sulindac and its analog bind RXRalpha and inhibit RXRalpha-dependent AKT signaling.; Cancer Cell. Jun. 15, 2010;17(6):560-73. doi: 10.1016/j.ccr.2010.04.023.
Kolluri et al., "The R-enantiomer of the nonsteroidal antiinflammatory drug etodolac binds retinoid X receptor and induces tumor-selective apoptosis", PNAS 2005, 102(7):2525-2530.
Liou et al., "Nonsteroidal Anti-inflammatory Drugs Induce Colorectal Cancer Cell Apoptosis by Suppressing 14-3-3E", Cancer Res 2007, 67(7):3185-3191.
Yasui et al., "Combination of Tumor Necrosis Factor-α with Sulindac Augments Its Apoptotic Potential and Suppresses Tumor Growth of Human Carcinoma Cells in Nude Mice", Cancer 2003, 97(6): 1412-1420.
International Search Report and Written Opinion mailed Jan. 27, 2012 for International Patent Application No. PCT/US11/356651, filed May 6, 2011.
Wang, Zhi-Gang et al., *Synthesis and SAR study of modulators inhibiting tRXRα-dependent AKT activation*, European Journal of Medicinal Chemistry, 62 (2013) 632-648.
Walters, Matthew J., et al., *The influence of double bond geometry in the inhibition of cyclooxygenases by sulindac derivatives*, Bioorganic & Medicinal Chemistry Letters, 19 (2009) 3271-3274.
Balkwill. Tumour necrosis factor and cancer. Nat Rev Cancer 9(5):361-371 (2009).
Cao et al. Retinoid X receptor regulates Nur77/TR3-dependent apoptosis [corrected] by modulating its nuclear export and mitochondrial targeting. Mol Cell Biol 24(22):9705-9725 (2004).

(Continued)

*Primary Examiner* — Kortney L Klinkel
*Assistant Examiner* — Tori M Strong
(74) *Attorney, Agent, or Firm* — Wilson, Sonsini, Goodrich & Rosati

(57) ABSTRACT

Provided herein are methods and compositions related to a retinoid receptor-selective pathway. As described herein, this pathway can be targeted to manipulate a tumor microenvironment. For example, the methods and compositions described herein can be used to induce apoptosis in a cancer cell. Further, the compositions described herein, including Sulindac and analogs thereof, can be used to target this pathway for the treatment or prevention of cancer in human patients.

9 Claims, 24 Drawing Sheets

(56) References Cited

OTHER PUBLICATIONS

Clifford et al. RXRalpha-null F9 embryonal carcinoma cells are resistant to the differentiation, anti-proliferative and apoptotic effects of retinoids. Embo J 15(16):4142-4155 (1996).
Han et al. Regulation of Nur77 nuclear export by c-Jun N-terminal kinase and Akt. Oncogene 25(21):2974-2986 (2006).
Kashfi et al. Non-COX-2 targets and cancer: expanding the molecular target repertoire of chemoprevention. Biochem Pharmacol 70(7):969-986 (2005).
Li et al. Cleavage of BID by caspase 8 mediates the mitochondrial damage in the Fas pathway of apoptosis. Cell 94(4):491-501 (1998).
Masia et al. Rapid, nongenomic actions of retinoic acid on phosphatidylinositol-3-kinase signaling pathway mediated by the retinoic acid receptor. Mol Endocrinol 21(10):2391-2402 (2007).
Ohashi et al. Activation of the P13 kinase pathway by retinoic acid mediates sodium/iodide symporter induction and iodide transport in MCF-7 breast cancer cells. Cancer Res 69(8):3443-3450 (2009).
Tegeder et al. Cyclooxygenase-independent actions of cyclooxygenase inhibitors. FASEB J 15(12):2057-2072 (2001).
Zhang et al. Homodimer formation of retinoid X receptor induced by 9-cis retinoic acid. Nature 358:587-591 (1992).
Zhang et al. Retinoid X receptor is an auxiliary protein for thyroid hormone and retinoic acid receptors. Nature 355:441-446 (1992).
Adams et al. PHENIX: a comprehensive Python-based system for macromolecular structure solution. Acta crystallographica Section D, Biological crystallography 66:213-221 (2010).
Arnold et al. Discovery of Small Molecule Inhibitors of the Interaction of the Thyroid Hormone Receptor with Transcriptional Coregulators. J Biol Chem 280:43048-43055 (2005).
Bourguet et al. Purification, functional characterization, and crystallization of the ligand binding domain of the retinoid X receptor. Protein Exp Purif 6:604-608 (1995).
Bushue et al. Retinoid pathway and cancer therapeutics. Adv Drug Deliv Rev 62:1285-1298 (2010).
Buzon et al. A conserved surface on the ligand binding domain of nuclear receptors for allosteric control. Mole Cell Endocrinol 348:394-402 (2012.
Caboni et al. "True" antiandrogens-selective non-ligand-binding pocket disruptors of androgen receptor-coactivator interactions: novel tools for prostate cancer. J Med Chem 55:1635-1644 (2012).
Casas et al. Endocrine regulation of mitochondrial activity: involvement of truncated RXRalpha and c-Erb Aalpha1 proteins. FASEB J 17:426-436 (2003).
Chen et al. Ligand- and DNA-induced dissociation of RXR tetramers. J Mol Biol 275:55-65 (1998).
Collaborative computational Project, No. 4. The CCP4 suite: programs for protein crystallography. Acta Crystallogr. D Biol. Crystallogr. 50:760-763 (1994).
Davies et al. Clinical Pharmacokinetics of Sulindac: A Dynamic Old Drug. Clinical Pharmacokinetics 32:437-459 (1997).
Dawson et al. Discovery and design of retinoic acid receptor and retinoid X receptor class- and subtype-selective synthetic analogs of all-trans-retinoic acid and 9-cis-retinoic acid. Curr Med Chem 9:623-637 (2002).
De Lera et al. Design of selective nuclear receptor modulators: RAR and RXR as a case study. Nat Rev Drug Discov 6:811-820 (2007).
Dufour et al. Cellular and subcellular localization of six retinoid receptors in rat testis during postnatal development: identification of potential heterodinieric receptors. Biol Reprod 61:1300-1308 (1999).
Duggan et al. Kinetics of the tissue distributions of sulindac and metabolites. Relevance to sites and rates of bioactivation. Drug Metabolism and Disposition 8:241-246 (1980).
Egea et al. Crystal structure of the human RXRαligand-binding domain bound to its natural ligand: 9-cis retinoic acid. EMBO J 79:2592-2601 (2000).
Emsley et al. Coot: model-building tools for molecular graphics. Acta crystallographica Section D, Biological crystallography 60:2126-2132 (2004).
Fukunaka et al. Changes in expression and subcellular localization of nuclear retinoic acid receptors in human endometrial epithelium during the menstrual cycle. Mol Hum Reprod 7:437-446 (2001).
Gampe et al. Structural basis for autorepression of retinoid X receptor by tetramer formation and the AF-2 helix. Genes Dev 14:2229-2241 (2000).
Germain et al. International Union of Pharmacology. LXIII. Retinoid X receptors. Pharm Rev 58:760-772 (2006).
Grootenhuis et al. Molecular Modelling of Protein—Ligand Interactions. Bull. Soc. Chim. Belg. 101:661-662 (1992).
Gunther et al. Amphipathic Benzenes Are Designed Inhibitors of the Estrogen Receptor alpha/Steroid Receptor Coactivator Interaction. ACS Chem Biol 3:282-286 (2008).
Herr. 5-Substituted-IH-tetrazoles as carboxylic acid isosteres: medicinal chemistry and synthetic methods. Bioorg Med Chem 10:3379-3393 (2002).
Hwang et al. Improvement of Pharmacological Properties of Irreversible Thyroid Receptor Coactivator Binding Inhibitors. J Med Chem 52:3892-3901 (2009).
Kabsch. XDS. Acta crystallographica Section D, Biological crystallography 66:125-132 (2010).
Kersten et al. Auto- silencing by the retinoid X receptor. J Mol Biol 284:21-32 (1998).
Kersten et al. Retinoid X receptor alpha forms tetramers in solution. PNAS USA 92:8645-8649 (1995).
Kirkpatrick et al. Structure-based drug design: combinatorial chemistry and molecular modeling. Comb Chem High Throughput Screen 2:211-221 (1999).
Kojetin et al. Implications of the binding of tamoxifen to the coactivator recognition site of the estrogen receptor. Endocr Relat Cancer 15:851-870 (2008).
Lawrence et al. CLIX: a search algorithm for finding novel ligands capable of binding proteins of known three-dimensional structure. Proteins 12:31-41 (1992).
Lazebnik et al. Cleavage of poly(ADP-ribose) polymerase by a proteinase with properties like ICE. Nature 371:346-347 (1994).
Lu et al. The effect of antagonists on the conformational exchange of the retinoid X receptor alpha ligand-binding domain. Mag Reson Chem 47:1071-1080 (2009).
Matta et al. The bioisosteric similarity of the tetrazole and carboxylate anions: Clues from the topologies of the electrostatic potential and of the electron density. Eur J Med Chem 45:1868-1872 (2010).
McCoy et al. Phaser crystallographic software. J Appl Crystall 40:658-674 (2007).
Miranker et al. Functionality maps of binding sites: a multiple copy simultaneous search method.Proteins 11:29-34 (1991).
Mita et al. LXXLL peptide mimetics as inhibitors of the interaction of vitamin D receptor with coactivators. Bioorg Med Chem Lett 20:1712-1717 (2010).
Mizwicki et al. Identification of an alternative ligand-binding pocket in the nuclear vitamin D receptor and its functional importance in 1alpha,25(OH)2-vitamin D3 signaling. PNAS USA 101:12876-12881 (2004).
Moore et al. Minireview: Not Picking Pockets: Nuclear Receptor Alternate-Site Modulators (NRAMs). Mol Endocrinol 24:683-695 (2010).
PCT/US2014/071989 International Preliminary Report on Patentability dated Jul. 7, 2016.
PCT/US2014/071989 International Search Report and Written Opinion dated Apr. 27, 2015.
Peet et al. Engineering novel specificities for ligand-activated transcription in the nuclear hormone receptor RXR. Chem Biol 5:13-21 (1998).
Rodriguez et al. Design, Synthesis, and in Vitro Biological Evaluation of Small Molecule Inhibitors of Estrogen Receptor a Coactivator Binding. J Med Chem 47:600-611 (2004).
Sato et al. The "Phantom Effect" of the Rexinoid LG100754: structural and functional insights. PLoS one 5:e15119 (2010).
Sun et al. Discovering small-molecule estrogen receptor alpha/coactivator binding inhibitors: high-throughput screening, ligand development, and models for enhanced potency. ChemMedChem 6:654-666 (2011).

(56) References Cited

OTHER PUBLICATIONS

Szanto et al. Retinoid X receptors: X-ploring their (patho)physiological functions. Cell Death Differ 11:S126-S143 (2004).
Whittle et al. Protein structure—based drug design. Annu. Rev. Biophys. Biomol. Struct. 23:349-375 (1994).

* cited by examiner

Figure 10
Sulindac Reference
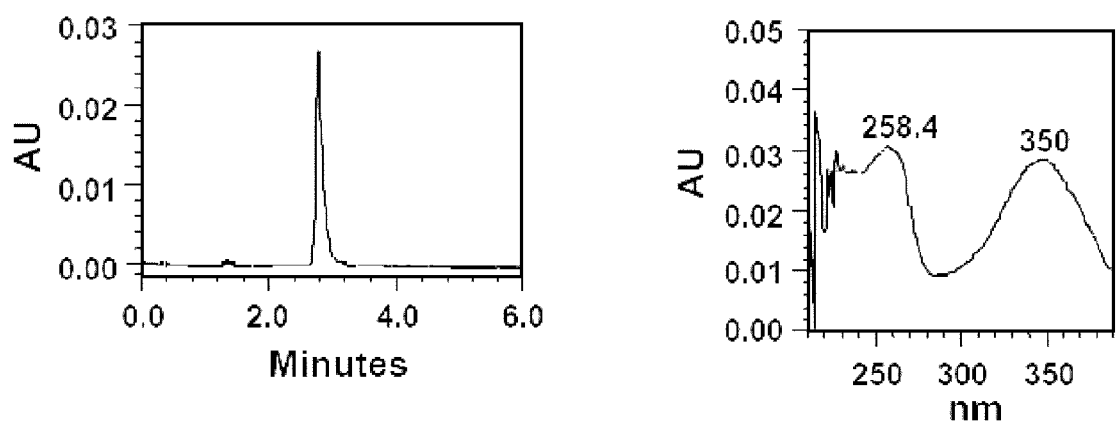
RXRα + Sulindac
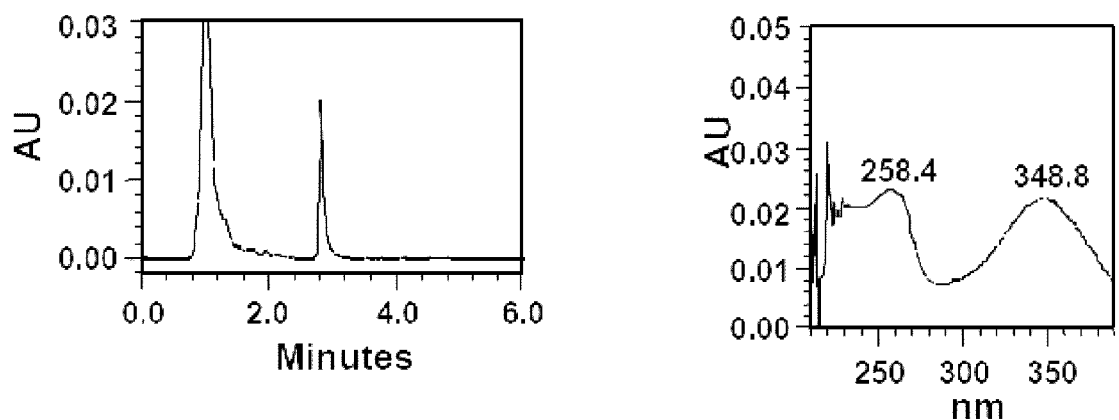
RXRα Reference
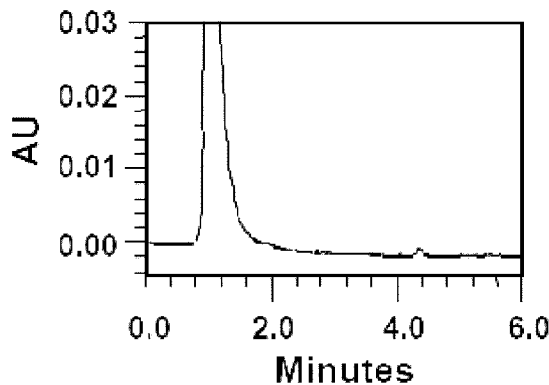

Figure 15
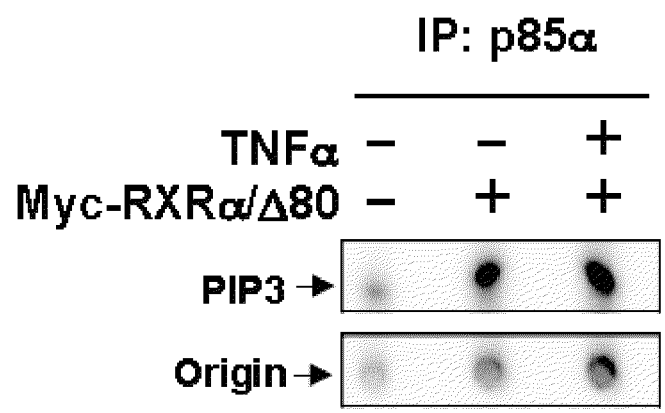
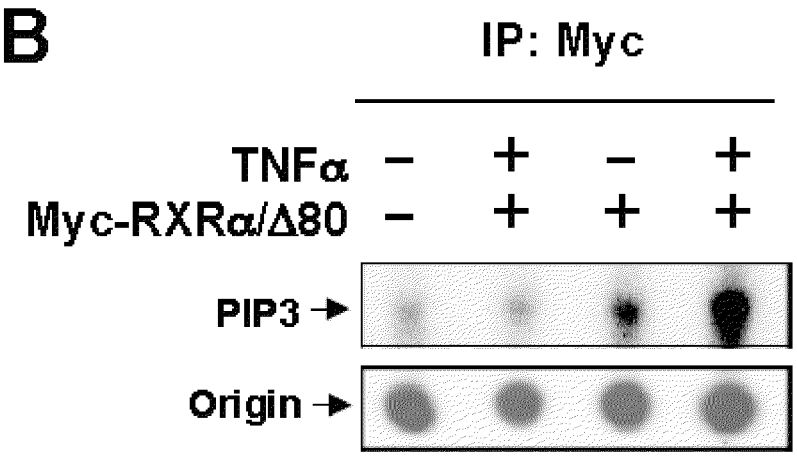

A

Figure 21 (cont'd)
B
Control
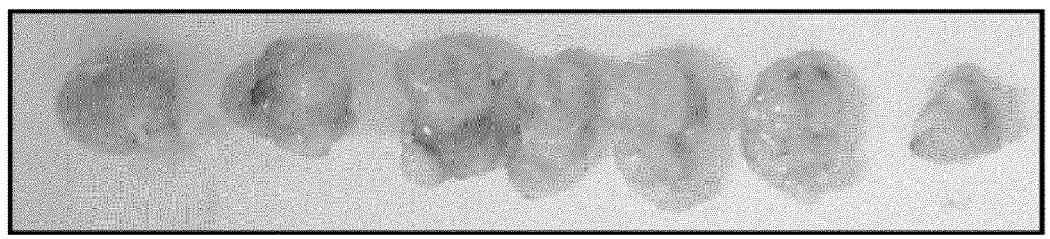
C
K-80003
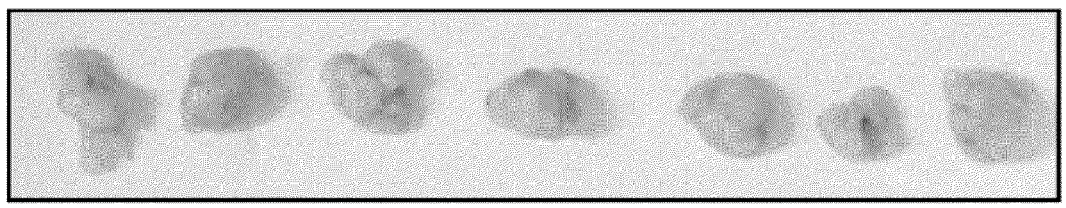

| Parameters | Unit | IV (3 mg/kg) | PO (30 mg/kg) | PO (60 mg/kg) |
|---|---|---|---|---|
| CL | mL/min/kg | 7.3 | | |
| Vd | L/kg | 0.7 | | |
| T1/2 | hr | 1.1 | 2.0 | 2.2 |
| AUC(0-t) | µg*hr/mL | 6.8 | 72.6 | 172.4 |
| AUC(0-∞) | µg*hr/mL | 6.9 | 77.4 | 187.9 |
| Cmax | µg/mL | 11.3 | 24.8 | 49.0 |
| Tmax | hr | | 0.5 | 1.0 |
| F | % | | 111.6% | 135.5% |

SEQUENCE LISTING

```
<160> NUMBER OF SEQ ID NOS: 6

<210> SEQ ID NO 1
<211> LENGTH: 29
<212> TYPE: DNA
<213> ORGANISM: Homo sapien

<400> SEQUENCE: 1
ccggaattcc atgagtgctg aggggtacc                                     29

<210> SEQ ID NO 2
<211> LENGTH: 30
<212> TYPE: DNA
<213> ORGANISM: Homo sapien

<400> SEQUENCE: 2
acgcgtcgac tcatcgcctc tgctgtgcat                                    30

<210> SEQ ID NO 3
<211> LENGTH: 56
<212> TYPE: DNA
<213> ORGANISM: Homo sapien

<400> SEQUENCE: 3
ggaacgagct gctgatcgcc tcctcctccc acgagtccat agctgtgaaa gatggg       56

<210> SEQ ID NO 4
<211> LENGTH: 56
<212> TYPE: DNA
<213> ORGANISM: Homo sapien

<400> SEQUENCE: 4
cccatctttc acagctatgg actcgtggga ggaggaggcg atcagcagct cgttcc       56
```

```
<210> SEQ ID NO 5
<211> LENGTH: 29
<212> TYPE: DNA
<213> ORGANISM: Homo sapien

<400> SEQUENCE: 5
ccggaattcg gaccacaccc accctgggc                                    29

<210> SEQ ID NO 6
<211> LENGTH: 29
<212> TYPE: DNA
<213> ORGANISM: Homo sapien

<400> SEQUENCE: 6
ccgctcgagc taagtcattt ggtgcggcg                                    29
```

METHODS AND COMPOSITIONS RELATED TO A RETINOID RECEPTOR-SELECTIVE PATHWAY

RELATED APPLICATIONS

This application claims priority under 35 U.S.C. §119(e) to U.S. Provisional Patent Application Ser. No. 61/332,124, filed on May 6, 20010, which is incorporated herein by reference in its entirety.

STATEMENT REGARDING FEDERALLY SPONSORED R&D

This invention was made with government support under CA109345 awarded by the NIH and under W81XWH-08-1-0478 awarded by the U.S. Army Medical Research and Material Command. The government has certain rights in the invention.

SEQUENCE LISTING

The present application is being filed along with a Sequence Listing in electronic format. The Sequence Listing is provided as a file entitled BURNHAM.029A_Sequence_Listing.TXT, created Jul. 20, 2011, which is 1.23 Kb in size. The information in the electronic format of the Sequence Listing is incorporated herein by reference in its entirety.

FIELD OF THE INVENTION

The present invention is in the field of methods and compositions related to a retinoid receptor-selective pathway.

BACKGROUND OF THE INVENTION

The anticancer effects of nonsteroidal antiinflammatory drugs (NSAIDs) are well-recognized (Tegeder, I. et al., *FASEB J* 15 (12), 2057-2072 (2001); Kashfi, K. & Rigas, B., *Biochem Pharmacol* 70 (7), 969-986 (2005)). NSAIDs block eicosanoid production through inhibition of cyclooxygenases (COX-1 and COX-2). NSAIDs have received significant attention as promising cancer chemopreventive agents since the discovery that regular use of aspirin reduced the incidence of colon cancer. Unfortunately, the promising anti-cancer effects of NSAIDs have been overshadowed by concomitantly emerging side effects, including life-threatening cardiovascular complications known to be associated with COX-2 inhibition. Despite the link between COX-2 and carcinogenesis, NSAIDs induce apoptosis in cancer cells containing neither COX-1 nor COX-2, indicating that other intracellular targets exist (Tegeder, I. et al., *FASEB J* 15 (12), 2057-2072 (2001); Kashfi, K. & Rigas, B., *Biochem Pharmacol* 70 (7), 969-986 (2005)).

SUMMARY OF THE INVENTION

Embodiments pertain to methods and compositions related to a retinoid receptor-selective pathway. In some embodiments, this pathway is targeted to manipulate a tumor microenvironment. In one embodiment, a method of inducing apoptosis in a cancer cell is provided. For example, a composition for preventing or treating cancer, such as the compound of formula (II) described herein, may be provided. In some embodiments a composition comprising the compound K-80003, or a K-80003 analog, as described herein, is used for the treatment of cancer.

As shown herein, Sulindac sulfide (hereinafter "Sulindac" or "Suldinac sulfide") binds to the compound RXRα at clinically relevant concentrations and induces apoptosis in a RXRα-dependent manner, identifying RXRα as an intracellular target of Sulindac action. As also shown herein, Sulindac potently inhibits activation of AKT (protein kinase B), a critical survival kinase in cancer cells. Further, an N-terminally truncated RXRα (tRXRα) is shown to mediate survival signaling in cancer cells. As shown herein, when combined with TNFα, Sulindac inhibits a TNFα-induced tRXRα/p85α interaction, leading to activation of the death receptor-mediated apoptotic pathway. Further, Sulindac analog K-80003, designed and synthesized as described herein, exhibits increased affinity to RXRα without COX inhibitory activity, and displays enhanced efficacy in inhibiting tRXRα-dependent AKT activation and tRXRα tumor growth in animals.

Described herein are Sulindac-derived RXRα ligands targeting an apoptotic pathway for cancer therapy. In one embodiment, a method of inducing apoptosis in a cancer cell is provided, comprising: upregulating tumor necrosis factor-α (TNFα) activity in a cancer cell, thereby sensitizing the cancer cell to the suppression of AKT; and contacting the sensitized cancer cell with a compound, where the compound is known to interact with retinoid X receptor-α (RXRα), and where the compound is known to suppress the activity of protein kinase B (AKT) independent of the cyclooxygenase-2 (COX-2) pathway. In one aspect of this embodiment, upregulating TNFα activity comprises introducing exogenous TNFα to the cancer cell. In another aspect of this embodiment, upregulating TNFα activity comprises upregulating endogenous TNFα in the cancer cell. In a further aspect of this embodiment, the cancer cell is a cancer cell selected from the group consisting of a lung cancer cell, a breast cancer cell, a prostate cancer cell, a liver cancer cell, and a colon cancer cell. In a further aspect of this embodiment, the cancer cell is a cancer cell selected from the group consisting of an A549 cell, an H460 cell, a ZR-75-1 cell, a MCF-7 cell, a LNCaP cell, a PC3 cell, a HepG2 cell, a Caco2 cell, and a SW480 cell. In a further aspect of this embodiment, the candidate compound is an analog of Sulindac, and where the analog exhibits at least one property selected from the group consisting of an $IC_{50}$ less than that of Sulindac when bound to RXRα and an $IC_{50}$ greater than that of Sulindac when bound to COX-2. In a further aspect of this embodiment, the analog is a compound selected from the group consisting of K-80001, K-80002, K-80003, K-80004, and K-80005. In a further aspect of this embodiment, the analog is K-80003.

In another embodiment, a method of screening a candidate compound for the ability to induce apoptosis in a cancer cell is provided, comprising: providing a candidate compound to a cancer cell; and determining whether the candidate compound is capable of at least one activity selected from the group consisting of: suppressing the activity of AKT, activating caspase-8, activating BAX, inhibiting cFLIP, and degrading Bid in the cancer cell. In one aspect of this embodiment, determining whether the candidate compound is capable of suppressing the activity of AKT comprises: activating AKT by pretreating the cancer cells with all-trans-retinoic acid (ATRA) or 9-cis-RA; and measuring a change in the level of AKT in the cancer cell following administration of the candidate compound.

In a further embodiment, a method of screening a candidate compound for the ability to induce apoptosis in a cell is provided, comprising: providing a candidate compound to a cell; and determining whether the candidate compound is capable of selectively binding to a truncated RXRα (tRXRα) protein. In one aspect of this embodiment, the candidate compound is a compound selected from the group consisting of a peptide, a protein, a nucleic acid, and a small molecule.

In a further embodiment, a method of screening a candidate compound for the ability to induce apoptosis in a cell is provided, comprising: providing a candidate compound to a cell; and determining whether the candidate compound is capable of regulating a tRXRα protein. In one aspect of this embodiment, the candidate compound is a compound selected from the group consisting of a peptide, a protein, a nucleic acid, and a small molecule. In another aspect of this embodiment, determining whether the candidate compound is capable of regulating a tRXRα protein comprises determining whether the candidate compound is capable of preventing tRXRα from binding to the p85α protein. In a further aspect of this embodiment, determining whether the candidate compound is capable of regulating a tRXRα protein comprises determining whether the candidate compound is capable of preventing RXRα from undergoing a protein modification. In a further aspect of this embodiment, the protein modification comprises phosphorylation. In a further aspect of this embodiment, determining whether the candidate compound is capable of regulating a tRXRα protein comprises determining whether the candidate compound is capable of preventing the tRXRα protein from migrating from the nucleus to the cytoplasm.

In a further embodiment, a method of screening a candidate compound for the ability to induce apoptosis in a cell is provided, comprising: identifying a cell expressing tRXRα; contacting the cell with a candidate compound; and determining whether the candidate compound induces apoptosis of the cell. In one aspect of this embodiment, the candidate compound is a compound selected from the group consisting of a peptide, a protein, a nucleic acid, and a small molecule. In another aspect of this embodiment, the candidate compound is a compound from a small molecule library. In a further aspect of this embodiment, the candidate compound is a compound from a peptide library. In a further aspect of this embodiment, the cell is from the breast or liver.

In a further embodiment, a method of screening a candidate compound for the ability to inhibit the growth of a tumor is provided, comprising: identifying a tumor expressing tRXRα; contacting the tumor with a candidate compound; and determining whether the candidate compound inhibits the growth of the tumor. In one aspect of this embodiment, the candidate compound is a compound selected from the group consisting of a peptide, a protein, a nucleic acid, and a small molecule. In another aspect of this embodiment, the candidate compound is a compound from a small molecule library. In a further aspect of this embodiment, the candidate compound is a compound from a peptide library. In a further aspect of this embodiment, the tumor is a tumor of the breast or liver.

In a further embodiment, a method of preventing cancer in a subject is provided, comprising: identifying a subject with an elevated risk for cancer relative to the general population; and providing to the subject an agent that suppresses the activity of AKT, where the binding of the agent to RXRα on the surface of a cell in the subject results in the suppression of AKT activity. In one aspect of this embodiment, the method further comprises administering TNFα to the subject prior to administering the agent, thereby sensitizing cancer cells in the subject to AKT inhibition by the agent. In another aspect of this embodiment, the agent is an analog of Sulindac. In a further aspect of this embodiment, the analog is a compound selected from the group consisting of K-80001, K-80002, K-80003, K-80004, and K-80005. In a further aspect of this embodiment, the analog is K-80003.

In a further embodiment, a method of treating cancer in a mammal is provided, comprising: identifying a mammal suffering from cancer and providing to the mammal a therapeutically effective amount of an agent known to suppresses the activity of AKT independent of the cyclooxygenase-2 (COX-2) pathway. In one aspect of this embodiment, the method further comprises administering TNFα to the mammal prior to administering the agent, thereby sensitizing cancer cells in the mammal to AKT inhibition by the agent. In another aspect of this embodiment, the agent is an analog of Sulindac. In a further aspect of this embodiment, the analog is a compound selected from the group consisting of K-80001, K-80002, K-80003, K-80004, and K-80005. In a further aspect of this embodiment, the analog is K-80003. In a further aspect of this embodiment, the mammal is a human.

In a further embodiment, a method of preventing or treating cancer in a mammal is provided, comprising administering to a mammal in need thereof a composition comprising the compound of formula (I), where A is an aryl or a heteroaryl, and where A can optionally be substituted by $R_3$ and 0, 1, or 2 $R_4$; where B is an aryl or a heteroaryl, and where B can optionally be substituted by 0, 1, or 2 $R_4$; where $R_1$ is $(CR_5R_6)_n COOH$; where $R_2$ is selected from the group consisting of H, a $C_{1-10}$ alkyl, an arylalkyl, a cycloalkyl, a cycloalkylalkyl, a haloalkyl, alkylO, alkylS, and haloalkylO; where $R_3$ and $R_4$ are independently selected from the group consisting of H, a $C_{1-10}$ alkyl, a haloalkyl, a halo, CN, an aryl, a heteroaryl, an arylalkyl, a heteroarylalkyl, alkylO, alkylS, $(CR_4R_6)_n CONR_7R_8$, OH, a cycloalkyl, a cycloalkylalkyl, cycloalkylO, and an alkoxyalkyl; where $R_5$ and $R_6$ are independently selected from the group consisting of H, a $C_{1-7}$alkyl, OH, an alkoxy, a cycloalkyl; or together form a cycloalkyl or heterocyclyl group; and where n is 0, 1, 2, or 3.

In a further embodiment, a method of preventing or treating cancer in a mammal is provided, comprising administering to a mammal in need thereof a composition comprising the compound of formula (II), where the compound exhibits at least one property selected from the group consisting of an $IC_{50}$ less than that of Sulindac when bound to RXRα and an $IC_{50}$ greater than that of Sulindac when bound to COX-2. In one aspect of this embodiment, $R_1$ is selected from the group consisting of $CH_2COOH$ and $CH_2CH_2COOH$; where $R_2$ is selected from the group consisting of $CH_3$ and H; and where $R_3$ is selected from the group consisting of 4-$SCH_3$, 4-$CH_3$, 4-$CH_2CH_3$, and 4-$CH(CH_3)_2$.

In a further embodiment, a method of screening a candidate compound for the ability to induce apoptosis in a cancer cell in an RXRα-selective manner is provided, comprising: providing a candidate compound to a cancer cell; and determining whether the candidate compound is capable of binding to RXRα without inhibiting COX-2 activity in the cancer cell. In one aspect of this embodiment, determining whether the candidate compound is capable of binding to RXRα comprises detecting an altered sensitivity of RXRα to chymotrypsin digestion in the cancer cell. In another aspect of this embodiment, determining whether the candidate compound is capable of binding to RXRα comprises detecting an altered differential scanning calorimetry (DSC) profile in the cancer cell.

In a further embodiment, a composition comprising a compound of formula (I) is provided, where A is an aryl or a heteroaryl, and where A can optionally be substituted by $R_3$ and 0, 1, or 2 $R_4$; where B is an aryl or a heteroaryl, and where B can optionally be substituted by 0, 1, or 2 $R_4$; where $R_1$ is $(CR_5R_6)_n$COOH; where $R_2$ is selected from the group consisting of H, a $C_{1-10}$ alkyl, an arylalkyl, a cycloalkyl, a cycloalkylalkyl, a haloalkyl, alkylO, alkylS, and haloalkylO; where $R_3$ and $R_4$ are independently selected from the group consisting of H, a $C_{1-10}$ alkyl, a haloalkyl, a halo, CN, an aryl, a heteroaryl, an arylalkyl, a heteroarylalkyl, alkylO, alkylS, $(CR_4R_6)_n$CONR$_7R_8$, OH, a cycloalkyl, a cycloalkylalkyl, cycloalkylO, and an alkoxyalkyl; where $R_5$ and $R_6$ are independently selected from the group consisting of H, a $C_{1-7}$alkyl, OH, an alkoxy, a cycloalkyl; or together form a cycloalkyl or heterocyclyl group; and where n is 0, 1, 2, or 3.

In a further embodiment, a composition comprising a compound of formula (II) is provided, where the composition exhibits at least one property selected from the group consisting of an $IC_{50}$ less than that of Sulindac when bound to RXRα and an $IC_{50}$ greater than that of Sulindac when bound to COX-2.

In a further embodiment, a composition comprising a compound of formula (II) is provided, where $R_1$ is selected from the group consisting of $CH_2$COOH and $CH_2CH_2$COOH; where $R_2$ is selected from the group consisting of $CH_3$ and H; and where $R_3$ is selected from the group consisting of 4-SCH$_3$, 4-CH$_3$, 4-CH$_2$CH$_3$, and 4-CH(CH$_3$)$_2$. In one aspect of this embodiment, the composition is selected from the group consisting of K-80001, K-80002, K-80003, K-80004, and K-80005. In another aspect of this embodiment, the composition is K-80003.

In a further embodiment, a composition comprising a compound of formula (III) is provided, where $R_1$ is selected from the group consisting of $CH_3$, F, and Cl; where $R_2$ is selected from the group consisting of H, $CH_3$, Cl, and F; and where $R_3$ is selected from the group consisting of $CH_3$, $CH_2CH_3$, $CH(CH_3)_2$, $C(CH_3)_3$, $CH_2$Cl, $OCH_3$, and $SCH_3$.

In a further embodiment, a composition comprising a compound of formula (IV) is provided, where $R_1$ is selected from the group consisting of $CH_3$, F, and Cl; where $R_2$ is selected from the group consisting of H, $CH_3$, Cl, and F; and where $R_3$ is selected from the group consisting of $CH_3$, $CH_2CH_3$, $CH(CH_3)_2$, $C(CH_3)_3$, $CH_2$Cl, $OCH_3$, and $SCH_3$.

In a further embodiment, a composition comprising a compound of formula (V) is provided, where $R_1$ is selected from the group consisting of COOH, $CH_2CH_2$COOH, CH=CHCOOH, $CH_2$-Tetrazole, $CH_2$—$CH_2$-Tetrazole, $CH_2$COOCH$_3$, $CH_3$, $CH_2$CONH$_2$, $CH_2$CONHCH$_3$, $CH_2$OH, $CH_2CH_2$OH, and $CH_2$NH$_2$; where $R_2$ is selected from the group consisting of H, Cl, $CH_2CH_3$, $OCH_3$, $NH_2$, NHCH$_3$, CF$_3$, $CH_2$NH$_2$, $CH_2$OH, $CH_2$Cl, $CH(CH_3)_2$, and $OCH_2CH_3$; where $R_3$ is selected from the group consisting of H, CH=CH$_2$, CCH, $C(CH_3)_3$, CF$_3$, OH, $OCH_3$, $OCH_2CH_3$, $NH_2$, NHCH$_3$, CN, NHCOCH$_3$,

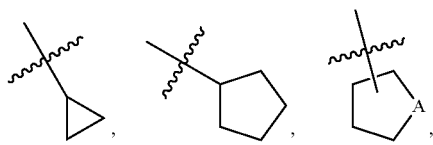

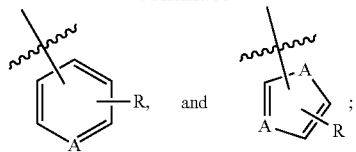

and where $R_4$ is selected from the group consisting of H, Cl, $CH_3$, $CH_2CH_3$, $CH(CH_3)_2$, $OCH_3$, OCHCH$_3$, $NH_2$, and NHCH$_3$.

In a further embodiment, a composition comprising a compound of formula (III) is provided, where $R_1$ is selected from the group consisting of $CH_3$, F, and Cl; $R_2$ is selected from the group consisting of H, $CH_3$, Cl, and F; and wherein $R_3$ is selected from the group consisting of $CH_3$, $CH_2CH_3$, $CH(CH_3)_2$, $C(CH_3)_3$, $CH_2$Cl, $OCH_3$, and $SCH_3$.

In a further embodiment, a composition comprising a compound of formula (IV) is provided, where $R_1$ is selected from the group consisting of $CH_3$, F, and Cl; where $R_2$ is selected from the group consisting of H, $CH_3$, Cl, and F; and where $R_3$ is selected from the group consisting of $CH_3$, $CH_2CH_3$, $CH(CH_3)_2$, $C(CH_3)_3$, $CH_2$Cl, $OCH_3$, and $SCH_3$.

In a further embodiment, a composition comprising a compound of formula (V) is provided, where $R_1$ is selected from the group consisting of COOH, $CH_2CH_2$COOH, CH=CHCOOH, $CH_2$-Tetrazole, $CH_2$—$CH_2$-Tetrazole, $CH_2$COOCH$_3$, $CH_3$, $CH_2$CONH$_2$, $CH_2$CONHCH$_3$, $CH_2$OH, $CH_2CH_2$OH, and $CH_2$NH$_2$, where $R_2$ is selected from the group consisting of H, Cl, $CH_2CH_3$, $OCH_3$, $NH_2$, NHCH$_3$, CF$_3$, $CH_2$NH$_2$, $CH_2$OH, $CH_2$Cl, $CH(CH_3)_2$, and $OCH_2CH_3$; and where $R_3$ is selected from the group consisting of H, CH=CH$_2$, CCH, $C(CH_3)_3$, CF$_3$, OH, $OCH_3$, $OCH_2CH_3$, $NH_2$, NHCH$_3$, CN, NHCOCH$_3$,

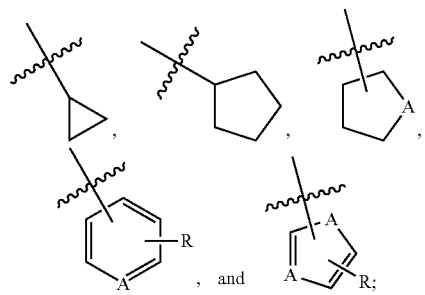

and where $R_4$ is selected from the group consisting of H, Cl, $CH_3$, $CH_2CH_3$, $CH(CH_3)_2$, $OCH_3$, OCHCH$_3$, $NH_2$, and NHCH$_3$.

In a further embodiment, a composition comprising an analog of Sulindac is provided, where the analog exhibits at least one property selected from the group consisting of an $IC_{50}$ less than that of Sulindac when bound to RXRα and an $IC_{50}$ greater than that of Sulindac when bound to COX-2.

In a further embodiment, a composition comprising a compound selected from the group consisting of 3-(4-Fluorophenyl)-2-methylacrylic acid; 3-(4-Fluorophenyl)-2-methylpropanoic acid, 6-Fluoro-2-methyl-2,3-dihydroinden-1-one; Ethyl 2-(6-Fluoro-2-methyl-3H-inden-1-yl)acetate; (Z)-2-(3-(4-(Methylthio)benzylidene)-6-fluoro-2-methyl-3H-inden-1-yl)acetic acid; (Z)-2-(3-(4-Methylbenzylidene)-6-fluoro-2-methyl-3H-inden-1-yl) acetic acid; (Z)-2-(3-(4-Ethylbenzylidene)-6-fluoro-2-methyl-3H-inden-1-yl)acetic acid; (Z)-2-(3-(4-Isopropylbenzylidene)-6-fluoro-2-methyl-3H-inden-1-yl)acetic acid; Ethyl 2-(6-fluoro-3H-inden-1-yl)acetate; (E)-2-(3-(4-(Methylthio)benzylidene)-6-fluoro-3H-inden-1-yl)acetic acid; Spiro(dihydro-2(3H)furanone-5-1'(2'H)(3'H)-6-fluoroindane; Methyl 3-(6-Fluoro-3H-inden-1-yl) propanoate; (E)-Methyl 3-(3-(4-(methylthio)benzylidene)-6-fluoro-3H-inden-1-yl)propanoate; K-80003 Analog No. 1; K-80003 Analog No. 2; K-80003 Analog No. 3; K-80003 Analog No. 4; K-80003 Analog No. 5; K-80003 Analog No. 6; K-80003 Analog No. 7; K-80003 Analog No. 8; K-80003 Analog No. 9; K-80003 Analog No. 10; K-80003 Analog No. 11; K-80003 Analog No. 12; K-80003 Analog No. 13; K-80003 Analog No. 14; K-80003 Analog No. 15; K-80003 Analog No. 16; K-80003 Analog No. 17; K-80003 Analog No. 18; K-80003 Analog No. 19; K-80003 Analog No. 20; K-80003 Analog No. 21; K-80003 Analog No. 22; K-80003 Analog No. 23; K-80003 Analog No. 24; K-80003 Analog No. 25; K-80003 Analog No. 26; K-80003 Analog No. 27; K-80003 Analog No. 28; K-80003 Analog No. 29; K-80003 Analog No. 30; K-80003 Analog No. 31; K-80003 Analog No. 32; K-80003 Analog No. 33; and K-80003 Analog No. 34 is provided.

BRIEF DESCRIPTION OF THE DRAWINGS

FIG. 10 is related to FIG. 1B and shows binding of Sulindac to RXRα protein as determined by HPLC analysis.

FIGS. 15A-B are related to FIG. 5E and show that tRXRα immunoprecipitates from A549 lung cancer cells.

DETAILED DESCRIPTION

Figure 1:
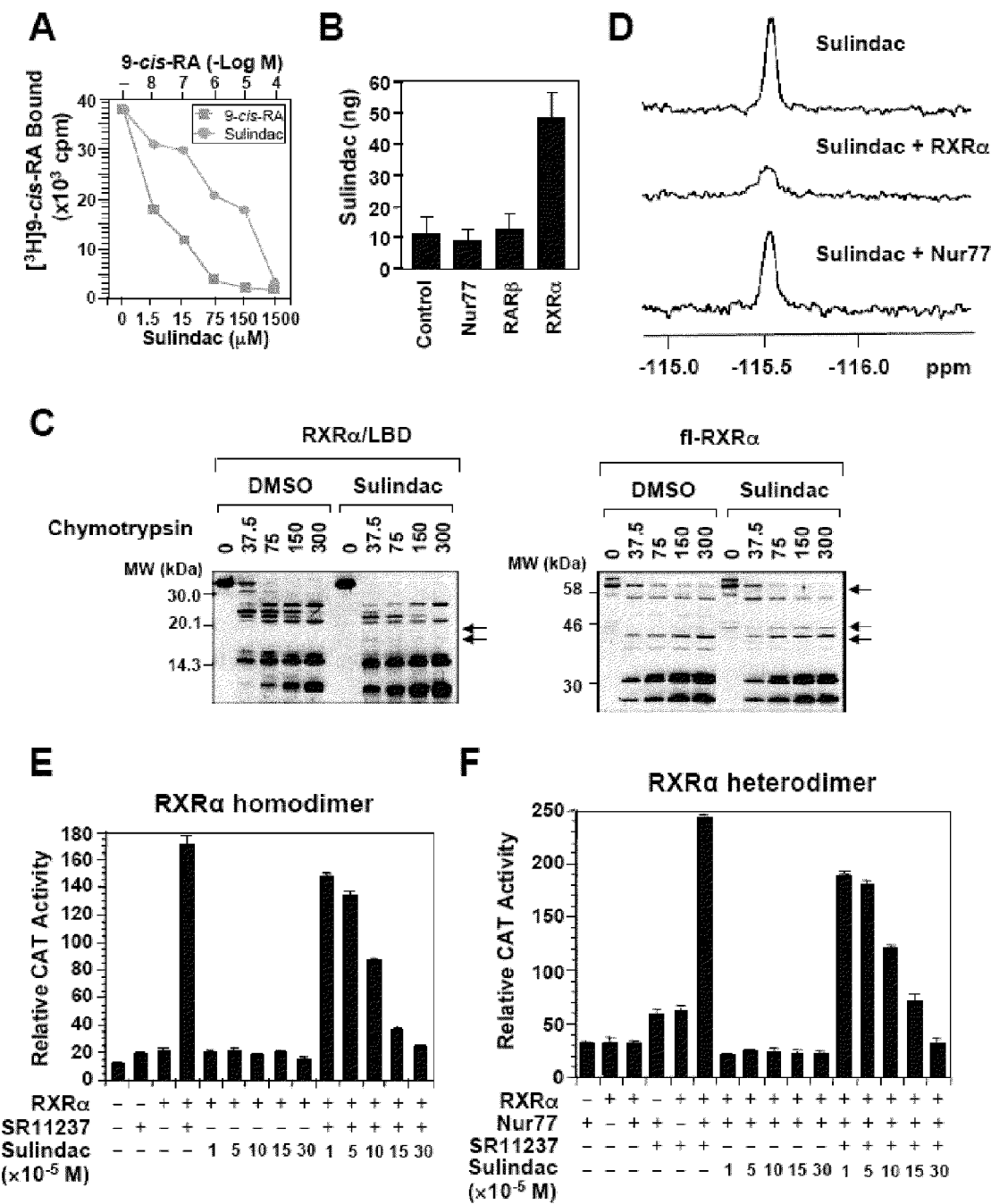
FIG. 1 shows Sulindac binding to RXRα. (a) Sulindac binding to RXRα LBD protein incubated with [$^3$H]9-cis-RA or unlabeled 9-cis-RA. (b) Sulindac binding to RXRα in HEK293 cells stably expressing RXRα, Nur77 or RARβ as determined by HPLC analysis. (c) Altered sensitivity of RXRα LBD or GST-RXRα to chymotrypsin by Sulindac. (d) Comparison of $^{19}$F NMR spectra of Sulindac in the absence and presence of RXRα LBD or Nur77 protein. Sulindac inhibits transactivation of RXRα homodimers and heterodimers as determined by (TREpal)2-tk-CAT activity (Zhang et al., Nature 358, 587-591 (1992a)) (e) or βRARE-tk-CAT activity (Zhang et al., Nature 355, 441-446 (1992b)) (f).

Various embodiments disclosed herein are generally directed towards compositions and methods related to a retinoid receptor-selective pathway. This pathway can be manipulated as described herein to treat or reduce the risk of developing cancer.

As shown herein, tRXRα constitutively resides in the cytoplasm, interacts with p85α, activates AKT, and confers anchorage-independent growth of cells. These observations reveal a tRXRα-mediated survival pathway in cancer cells, providing new insights into the role of RXRα and its ligands in cancer. Such activation of the PI3K/AKT survival pathway by proteolytic processing of RXRα is similar to the activation of apoptotic pathways by truncated Bid (tBid) and the activation of the Notch pathway by truncated Notch protein. Interestingly, cleavage of Bid and Notch also alters their subcellular localization, similar to the effect on RXRα truncation. The finding that RXRα serves as an intracellular target of Sulindac action prompted the design of RXRα-selective Sulindac derivatives for suppressing AKT activity described herein. For example, provided herein is the design and synthesis of a Sulindac-derived RXRα ligand, K-80003, with greater affinity to RXRα, and enhanced efficacy in inhibiting AKT, but lacking COX inhibitory activity. In addition, as described herein, the upregulation of endogenous TNFα and/or the introduction of exogenous TNFα may be useful in priming cancer cells for responsiveness.

In some embodiments, the composition comprises a core structure having formula I:

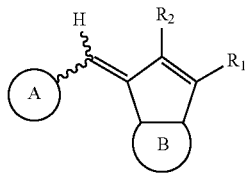

In some embodiments, A is an aryl or a heteroaryl, and can optionally be substituted by $R_3$ and 0, 1, or 2 $R_4$. In some embodiments, B is an aryl or a heteroaryl, and can optionally be substituted by 0, 1, or 2 $R_4$. In some embodiments, $R_1$ is $(CR_5R_6)_n$COOH. In some embodiments, $R_2$ is selected from the group consisting of H, a $C_{1-10}$ alkyl, an arylalkyl, a cycloalkyl, a cycloalkylalkyl, a haloalkyl, alkylO, alkylS, haloalkylO, $NH_2$, and alkylN. In some embodiments, $R_3$ and $R_4$ are independently selected from the group consisting of H, a $C_{1-10}$ alkyl, a haloalkyl, a halo, CN, an aryl, a heteroaryl, an arylalkyl, a heteroarylalkyl, alkylO, alkylS, $(CR_4R_6)_n$CONR$_7$R$_8$, OH, a cycloalkyl, a cycloalkylalkyl, cycloalkylO, and an alkoxyalkyl. In some embodiments, $R_5$ and $R_6$ are independently selected from the group consisting of H, a $C_{1-7}$alkyl, OH, an alkoxy, and a cycloalkyl; or together form a cycloalkyl or heterocyclyl group. In some embodiments, n is selected from the group consisting of 0, 1, 2, and 3.

In some embodiments, the composition comprises a core structure having formula II:

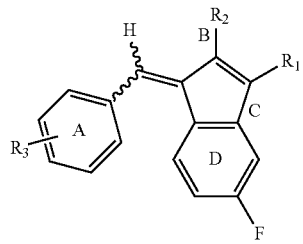

In some embodiments, $R_1$ is selected from the group consisting of $CH_2$COOH and $CH_2CH_2$COOH. In some embodiments, $R_2$ is selected from the group consisting of $CH_3$ and H. In some embodiments, $R_3$ is selected from the group consisting of 4-$SCH_3$, 4-$CH_3$, 4-$CH_2CH_3$, and 4-CH$(CH_3)_2$.

In some embodiments, the composition comprises a core structure having formula III:

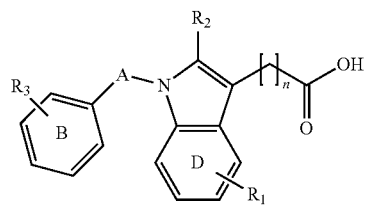

In some embodiments, n=2. In some embodiments, $R_1$ is selected from the group consisting of $CH_3$, F, and Cl. In some embodiments, $R_2$ is selected from the group consisting of H, $CH_3$, Cl, and F. In some embodiments, $R_3$ is selected from the group consisting of $CH_3$, $CH_2CH_3$, $CH(CH_3)_2$, $C(CH_3)_3$, $CH_2Cl$, $OCH_3$, and $SCH_3$. In some embodiments, B and/or D is a hetero ring (e.g., limited to a hetero atom).

In some embodiments, COOH from formula III is replaced with tetrazole. For example, in some embodiments, the composition comprises a core structure having formula IV:

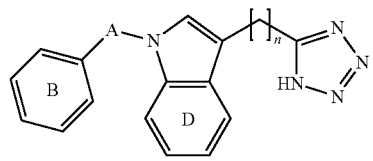

In some embodiments, n=2. In some embodiments, $R_1$ is selected from the group consisting of $CH_3$, F, and Cl. In some embodiments, $R_2$ is selected from the group consisting of H, $CH_3$, Cl, and F. In some embodiments, $R_3$ is selected from the group consisting of $CH_3$, $CH_2CH_3$, $CH(CH_3)_2$, $C(CH_3)_3$, $CH_2Cl$, $OCH_3$, and $SCH_3$. In some embodiments, B and/or D is a hetero ring (e.g., limited to a hetero atom).

In some embodiments, the composition comprises a core structure having formula V:

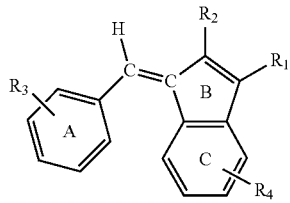

In some embodiments, $R_1$ is selected from the group consisting of COOH, $CH_2CH_2$COOH, CH=CHCOOH, $CH_2$-Tetrazole, $CH_2$—$CH_2$-Tetrazole, $CH_2$COOCH$_3$, $CH_3$, $CH_2$CONH$_2$, $CH_2$CONHCH$_3$, $CH_2$OH, $CH_2CH_2$OH, and $CH_2NH_2$. In some embodiments, $R_2$ is selected from the group consisting of H, Cl, $CH_2CH_3$, $OCH_3$, $NH_2$, NHCH$_3$, $CF_3$, $CH_2NH_2$, $CH_2$OH, $CH_2$Cl, $CH(CH_3)_2$, and $OCH_2CH_3$. In some embodiments, $R_3$ is selected from the group consisting of H, CH=CH$_2$, CCH, $C(CH_3)_3$, $CF_3$, OH, $OCH_3$, $OCH_2CH_3$, $NH_2$, NHCH$_3$, CN, NHCOCH$_3$,

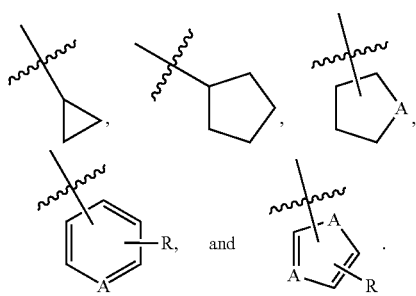

In some embodiments, $R_4$ is selected from the group consisting of H, Cl, $CH_3$, $CH_2CH_3$, $CH(CH_3)_2$, $OCH_3$, OCHCH$_3$, NH$_2$, and NHCH$_3$. Further, any of R$_1$ to R$_4$ can be any other suitable group known to one of skill in the art.

In some embodiments, the composition comprises a core structure having formula VI:

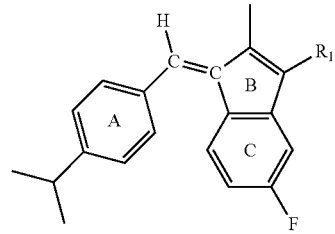

where R$_1$ is selected from the group consisting of COOH, CH$_2$CH$_2$COOH, CH=CHCOOH, CH$_2$-Tetrazole, CH$_2$—CH$_2$-Tetrazole, CH$_2$COOCH$_3$, CH$_3$, CH$_2$CONH$_2$, CH$_2$CONHCH$_3$, CH$_2$OH, CH$_2$CH$_2$OH, and CH$_2$NH$_2$.

In some embodiments, the composition comprises a core structure having formula VII:

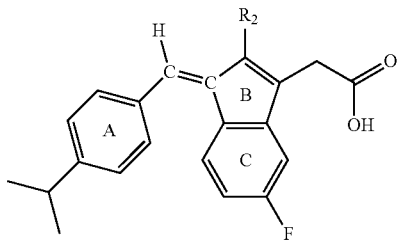

where R$_2$ is selected from the group consisting of H, Cl, CH$_2$CH$_3$, OCH$_3$, NH$_2$, NHCH$_3$, CF$_3$, CH$_2$NH$_2$, CH$_2$OH, CH$_2$Cl, CH(CH$_3$)$_2$, and OCH$_2$CH$_3$ In some embodiments, the composition comprises a core structure having formula VIII:

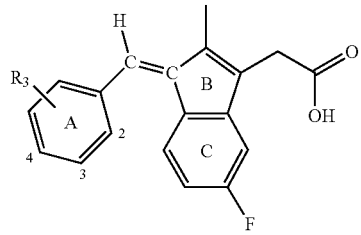

where R$_3$ is selected from the group consisting of H, CH=CH$_2$, CCH, C(CH$_3$)$_3$, CF$_3$, OH, OCH$_3$, OCH$_2$CH$_3$, NH$_2$, NHCH$_3$, CN, NHCOCH$_3$,

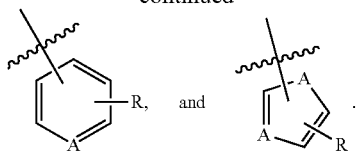

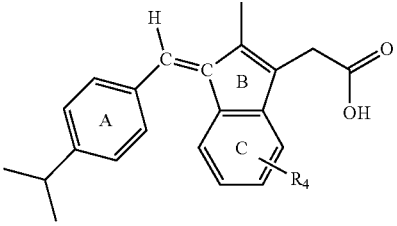

In some embodiments, the composition comprises a core structure having formula IX:

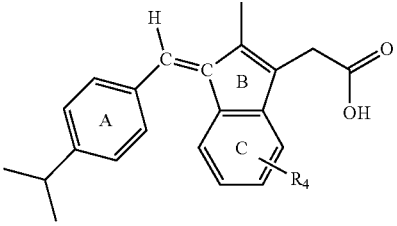

where R$_4$ is selected from the group consisting of H, Cl, CH$_3$, CH$_2$CH$_3$, CH(CH$_3$)$_2$, OCH$_3$, OCHCH$_3$, NH$_2$, and NHCH$_3$.

Some embodiments of the invention additionally provide analogs of compounds, including analogs and derivatives of the compounds shown in Example 16, having a core structure of any of formulas I to IX, and/or otherwise provided herein. It is understood that various modifications can be made to the compounds described herein to generate analogs using known methods. It is further understood that the R groups in the various core structures can be varied. It is also understood that analogs of the compounds disclosed herein can be readily prepared by one skilled in the art using known methods of chemical synthesis and performing structure activity relationship (SAR) studies. Furthermore, one skilled in the art can readily determine the activity of various analogs using the methods described herein.

In some embodiments, the IC$_{50}$ of the analog bound to RXRα is about 1%, 5%, 10%, 15%, 20%, 25%, 30%, 35%, 40%, 45%, 50%, 55%, 60%, 65%, 70%, 75%, 80%, 85%, 90%, 95%, or 99% of the IC$_{50}$ of Sulindac when bound to RXRα.

In some embodiments, the IC$_{50}$ of the analog bound to COX-1 is about 5%, 10%, 15%, 20%, 25%, 30%, 35%, 40%, 45%, 50%, 55%, 60%, 65%, 70%, 75%, 80%, 85%, 90%, 95%, or 100% greater than the IC$_{50}$ of Sulindac when bound to COX-1. In some embodiments, the IC$_{50}$ of the analog bound to COX-1 is about 1.5×, 2×, 2.5×, 3×, 3.5×, 4×, 4.5×, 5×, 6×, 7×, 8×, 9×, 10×, 50×, 100×, 250×, 500×, or 1000× greater than the IC$_{50}$ of Sulindac when bound to COX-1.

In some embodiments, the IC$_{50}$ of the analog bound to COX-2 is about 5%, 10%, 15%, 20%, 25%, 30%, 35%, 40%, 45%, 50%, 55%, 60%, 65%, 70%, 75%, 80%, 85%, 90%, 95%, or 100% greater than the IC$_{50}$ of Sulindac when bound to COX-2. In some embodiments, the IC$_{50}$ of the analog bound to COX-2 is about 1.5×, 2×, 2.5×, 3×, 3.5×, 4×, 4.5×, 5×, 6×, 7×, 8×, 9×, 10×, 50×, 100×, 250×, 500×, or 1000× greater than the IC$_{50}$ of Sulindac when bound to COX-2.

The following definitions are set forth to illustrate and define the meaning and scope of the various terms used to describe the invention herein.

As used herein, "alkoxy" refers to an alkyl group attached to the parent molecular moiety through an oxygen atom.

As used herein, "alkoxyalkyl" refers to an alkyl group substituted with one, two, or three alkoxy groups.

As used herein, "alkyl" refers to a group derived from a straight or branched chain saturated hydrocarbon containing from one to ten carbon atoms.

As used herein, "aryl" refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl.

As used herein, "arylalkyl" refers to an alkyl group substituted with one, two, or three aryl groups.

As used herein, "cycloalkyl" refers to a saturated monocyclic or bicyclic hydrocarbon ring system having three to ten carbon atoms and zero heteroatoms. Representative examples of cycloalkyl groups include, but are not limited to, cyclopropyl, cyclobutyl, and cyclopentyl.

As used herein, "cycloalkylalkyl" refers to an alkyl group substituted with one, two, or three cycloalkyl groups.

As used herein, "halo" and "halogen" refer to F, Cl, Br, and I.

As used herein, "haloalkyl" refers to an alkyl group substituted with one, two, three, or four halogen atoms.

As used herein, "heterocyclyl" refers to a five-, six-, or seven-membered ring containing one, two, or three heteroatoms independently selected from nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a four- to six-membered aromatic or non-aromatic carbocyclic ring or another monocyclic heterocyclyl group. The heterocyclyl groups of the present disclosure can be attached to the parent molecular moiety through a carbon atom or a nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl.

As used herein, "pharmaceutically or therapeutically acceptable carrier" refers to a carrier medium which does not interfere with the effectiveness of the biological activity of the active ingredients and which is minimally toxic to the host or patient.

As used herein, "stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers can have an optical rotation that is so slight that it is undetectable with present instrumentation. The compounds described herein can have one or more asymmetrical carbon atoms and therefore include various stereoisomers. All stereoisomers are included within the scope of the present invention.

As used herein, "suppressing" the activity of AKT refers to the prevention, amelioration, elimination, or any other reduction of AKT activity. For example, suppressing the activity of AKT can include decreasing basal levels of AKT or inhibiting AKT activation.

As used herein, "therapeutically- or pharmaceutically-effective amount" as applied to the disclosed compositions refers to the amount of composition sufficient to induce a desired biological result. That result can be prevention, alleviation, or amelioration of the signs, symptoms, causes of a disease, or any other desired alteration of a biological system. For example, the result can involve a decrease and/or reversal of cancerous cell growth.

As used herein, the term "inhibitor" is interchangeably used to denote "antagonist." Both these terms define compositions which have the capability of decreasing certain enzyme activity or competing with the activity or function of a substrate of said enzyme.

As used herein, "cancer" and "cancerous" refer to any malignant proliferation of cells in a mammal.

The pharmaceutical compositions disclosed herein can be used for prevention and treatment of any malignancy known to one of skill in the art, including hormone-refractory-prostate cancer, prostate cancer, breast cancer, ovarian cancer, colon cancer, melanoma or other skin cancer, lung cancer, hepatocarcinoma, acute myelogenous leukemia, bladder cancer, cervical cancer, cholangiocarcinoma, chronic myelogenous leukemia, colorectal cancer, gastric sarcoma, glioma, leukemia, lymphoma, multiple myeloma, osteosarcoma, pancreatic cancer, stomach cancer, or tumors at localized sites (including inoperable tumors or in tumors where localized treatment of tumors would be beneficial, and solid tumors).

For in vivo applications, the appropriate dose of a given cytotoxic agent depends on the agent and its formulation, and it is well within the ordinary skill of the art to optimize dosage and formulation for a given patient. Thus, for example, such agents can be formulated for administration via oral, subcutaneous, parenteral, submucosal, intravenous, or other suitable routes using standard methods of formulation. The effective amount and method of administration of compounds will vary based upon the sex, age, weight and disease stage of the patient, whether the administration is therapeutic or prophylactic, and other factors apparent to those skilled in the art.

Those skilled in the art will derive appropriate dosages and schedules of administration to suit the specific circumstances and needs of the patient, e.g., dependent on the subject's weight, the severity of the affliction, the manner of administration and the judgment of the prescribing physician. Typically, the dose range of the composition administered to the patient can be from about 0.5 to 1000 mg/kg of the patient's body weight. The dosage may be a single one or a series of two or more given in the course of one or more days, as is needed by the patient. In some embodiments, the present invention will use the same dosages, or dosages that are between about 0.1% and 500%, more preferably between about 25% and 250% of the established human dosage for analogs. Suitable human dosages can also be inferred from $ED_{50}$ or $ID_{50}$ values, or other appropriate values derived from in vitro or in vivo studies, e.g., as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between 0.1 mg and 500 mg, preferably between about 1 mg and about 250 mg, e.g., about 150 to about 200 mg. In some embodiments, the oral dosage form is about 5 mg, 10 mg, 25 mg, 50 mg, 100 mg, 125 mg, 150 mg, 175 mg, 200 mg, 225 mg, 250 mg, 300 mg, 350 mg, 400 mg, 450 mg, 500 mg, 600 mg, 700 mg, 800 mg, 900 mg, or 1000 mg.

Compounds can be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages for achieving the MEC will depend on individual characteristics and route of administration. However, HPLC assays or bioassays can be used to determine plasma concentrations.

The compositions may, if desired, be presented in a pack or dispenser device which may contain one or more unit dosage forms containing the active ingredient. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

EXAMPLES

Example 1

Sulindac Binding to RXRα

Competitive ligand-binding assays (FIG. 1A) and HPLC analysis of Sulindac binding to RXRα, Nur77, or RARβ in HEK293T cells (FIG. 1B) were performed. RXRα LBD protein was incubated with [$^3$H]9-cis-RA in the presence or absence of Sulindac or unlabeled 9-cis-RA. Bound [$^3$H]9-cis-RA was quantitated by liquid scintillation counting (FIG. 1A). HEK293T cells stably expressing RXRα fused to a C-terminal TAP tag (Stratagene, La Jolla, Calif.) were treated with or without 100 μM sulindac sulfide for 3 hr. After treatment, cells were purified and analyzed by HPLC for the presence of sulindac sulfide. A standard solution of sulindac sulfide was used to obtain the calibration curve. Characteristic peak spectrum and retention time was used for identification, and peak areas at max used for quantification were calculated (FIGS. 1B and 10). Sulindac sulfide bound to RXRα with an $IC_{50}$ of 80 μM (FIG. 1A), which is in the concentration range that induces apoptosis. HPLC analysis showed a direct binding of Sulindac to RXRα, but not other nuclear receptors such as RAR and Nur77 in cells (FIGS. 1B and 10).

Figure 9:
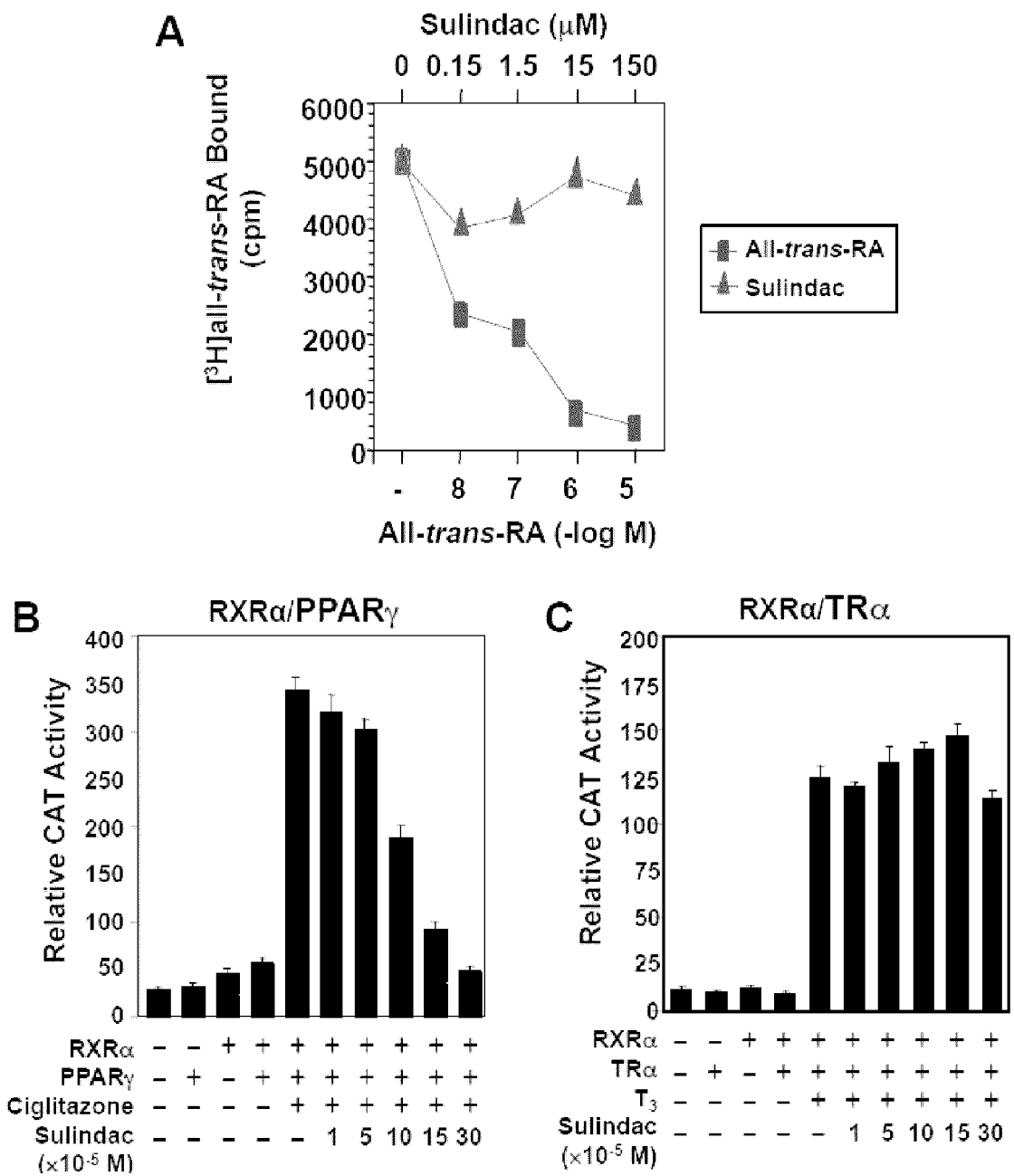
FIGS. 9A-C are related to FIG. 1 and show the binding of Sulindac to RXRα and its effect on RXRα transactivation.

Purified RARγ protein was incubated with [$^3$H]all-trans-RA in the presence or absence of Sulindac or unlabeled all-trans RA. Bound [$^3$H]all-trans-RA was quantitated by liquid scintillation counting. Sulindac did not bind to RARγ, consistent with the cell-based experiment shown in FIG. 1B (FIG. 9A).

Receptor expression vectors and a reporter gene (TREpal$_2$-tk-CAT for RXRα/TRα heterodimers (FIG. 9B), and DR1 tk-CAT for RXRα/PPARγ heterodimer (FIG. 9C)) were transiently transfected into CV-1 cells. Cells were treated with or without ligands (ciglitazone, $10^{-6}$ M; $T_3$, $10^{-7}$ M) in the presence or absence of Sulindac. CAT activity was determined. Sulindac inhibited transactivation of RXRα/PPARγ heterodimers, but not RXR/TR heterodimers FIGS. 9B, C)

Altered sensitivity of RXRα ligand-binding domain (LBD) to chymotrypsin (ug/ml) by Sulindac (100 μM) (FIG. 1C) and differential scanning calorimetry (DSC) scans comparing $^{19}$F NMR spectra of Sulindac (100 μM) in the absence and presence of 10 μM RXRα LBD or Nur77 protein (FIG. 1D) were also determined. Binding to RXRα was confirmed by altered sensitivity of RXRα to chymotrypsin digestion by Sulindac (FIG. 1C) and differential scanning calorimetry (DSC) (FIG. 1D). In addition, inhibition of SR11237 ($10^{-6}$ M)-activated RXRα transactivation by Sulindac was measured (FIG. 1F, see Example 2).

Nur77 and/or RXRα were transiently transfected into CV-1 cells. Cells were treated with or without SR11237 ($10^{-6}$ M), a RXR-selective agonist, in the presence or absence of Sulindac. (TREpal)2-tk-CAT (Zhang et al., Nature 358, 587-591 (1992a))) (FIG. 1E) and βRARE-tk-CAT (Zhang et al., Nature 355, 441-446 (1992b)) (FIG. 1F) CAT activity were determined. Sulindac binding inhibited RXRα homodimer and heterodimer transactivation in the reporter assays (FIGS. 1E,F and FIG. 10), demonstrating that Sulindac is a RXRα transcriptional antagonist.

Example 2

Death Effect of Sulindac

To determine the role of RXRα in Sulindac-induced apoptosis, the death effect of Sulindac in F9 cells and F9 cells lacking RXRα (F9-RXRα-/-) was examined.

For nuclear morphological change analysis, cells were trypsinized, washed with PBS, fixed with 3.7% paraformaldehyde, and stained with DAPI (4,6-diamidino-2-phenylindole) (1 mg/ml) to visualize the nuclei by fluorescent microscopy. The percentages of apoptotic cells were determined by counting at least 300 GFP-positive cells having nuclear fragmentation and/or chromatin condensation. For the determination of DNA fragmentation, the Cell Death Detection ELISA$^{PLUS}$ (Roche Applied Science, Penzberg, Bavaria, Germany) was used.

RXRα siRNA siGENOME SMARpool (M-003443-02), RARγ siRNA siGENOME SMARpool (M-003439-01), and siRNA Non-specific Control IX (D-001206-09-05) were purchased from DHARMACON (Lafayette, Colo.). A 2.5 μl aliquot of 20 mM siRNA per well was transfected into cells grown in 12-well plates by using oligofectamine reagent (Invitrogen, Carlsbad, Calif.) according to manufacturer's recommendations. Two days after transfection, the cells were harvested for Western blotting.

Figure 2:
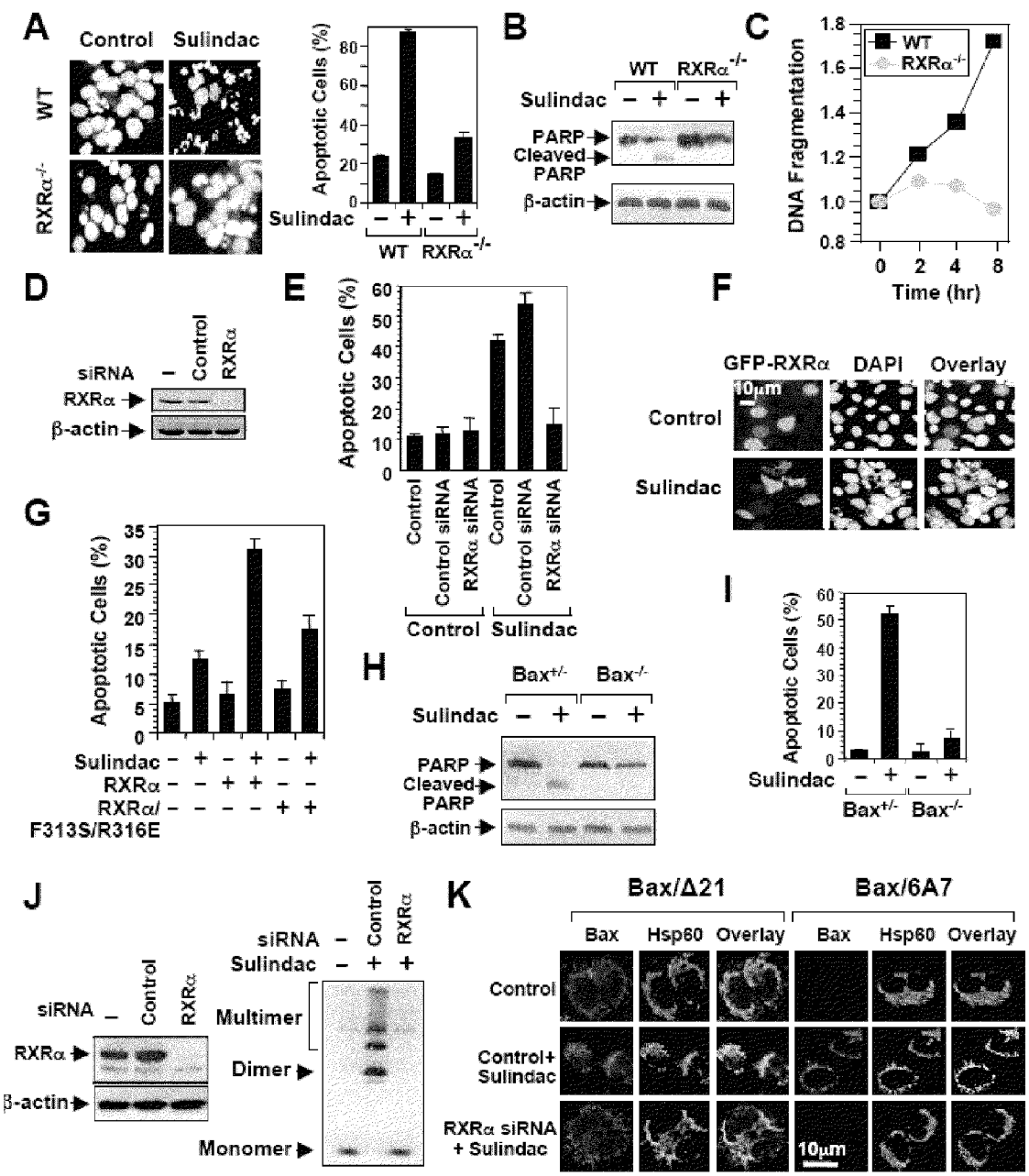
FIG. 2 shows Sulindac inducing RXRα-dependent apoptosis and Bax activation. Apoptotic effects of Sulindac in F9 or F9 cells lacking RXRα (F9 RXRα$^{-/-}$) as analyzed by DAPI staining (a), PARP cleavage (b), and DNA fragmentation (c). RXRα siRNA inhibits apoptosis induction by Sulindac. H460 lung cancer cells transfected with control or RXRα siRNA (d) treated with Sulindac and analyzed by DAPI staining for apoptosis (e). (f) Transfection of RXRα enhances the apoptotic effect of Sulindac. CV-1 cells transfected with GFP-RXRα were treated with Sulindac and analyzed by DAPI staining. (g) Disruption of the RXRα LBP impairs the apoptotic effect of Sulindac. CV-1 cells transfected with GFP-RXRα or GFP-RXRα/F313S/R316E were treated with Sulindac and analyzed by DAPI staining. Apoptosis scored in receptor transfected cells. Role of Bax in apoptosis induction. HCT116 cells or HCT116 cells lacking Bax (Bax$^{-/-}$) were treated with or without Sulindac. Apoptosis determined by PARP cleavage (h) and DAPI staining (i). (j,k) RXRα siRNA inhibits sulindac-induced Bax activation. Knocking down RXRα in HCT116 cells by RXRα siRNA revealed by immunoblotting. HCT116 cells transfected with or without RXRα siRNA or control siRNA were treated with Sulindac, and analyzed for Bax oligomerization (j) and Bax conformational change and mitochondrial targeting by immunostaining/confocal microscopy using Bax/Δ21, Bax/6A7, or anti-Hsp60 antibody (k).

F9 or F9 cells lacking RXRα (F9 RXRα-/-) were treated with Sulindac (75 μM) for 24 hr and analyzed by DAPI staining (FIG. 2A), poly (ADP-ribose) polymerase (PARP) cleavage (FIG. 2B), and DNA fragmentation (FIG. 2C). H460 lung cancer cells were transfected with control or RXRα siRNA, treated with Sulindac (75 μM) for 24 hr, and analyzed by DAPI staining for apoptosis (FIGS. 2D and 2E).

Figure 11:
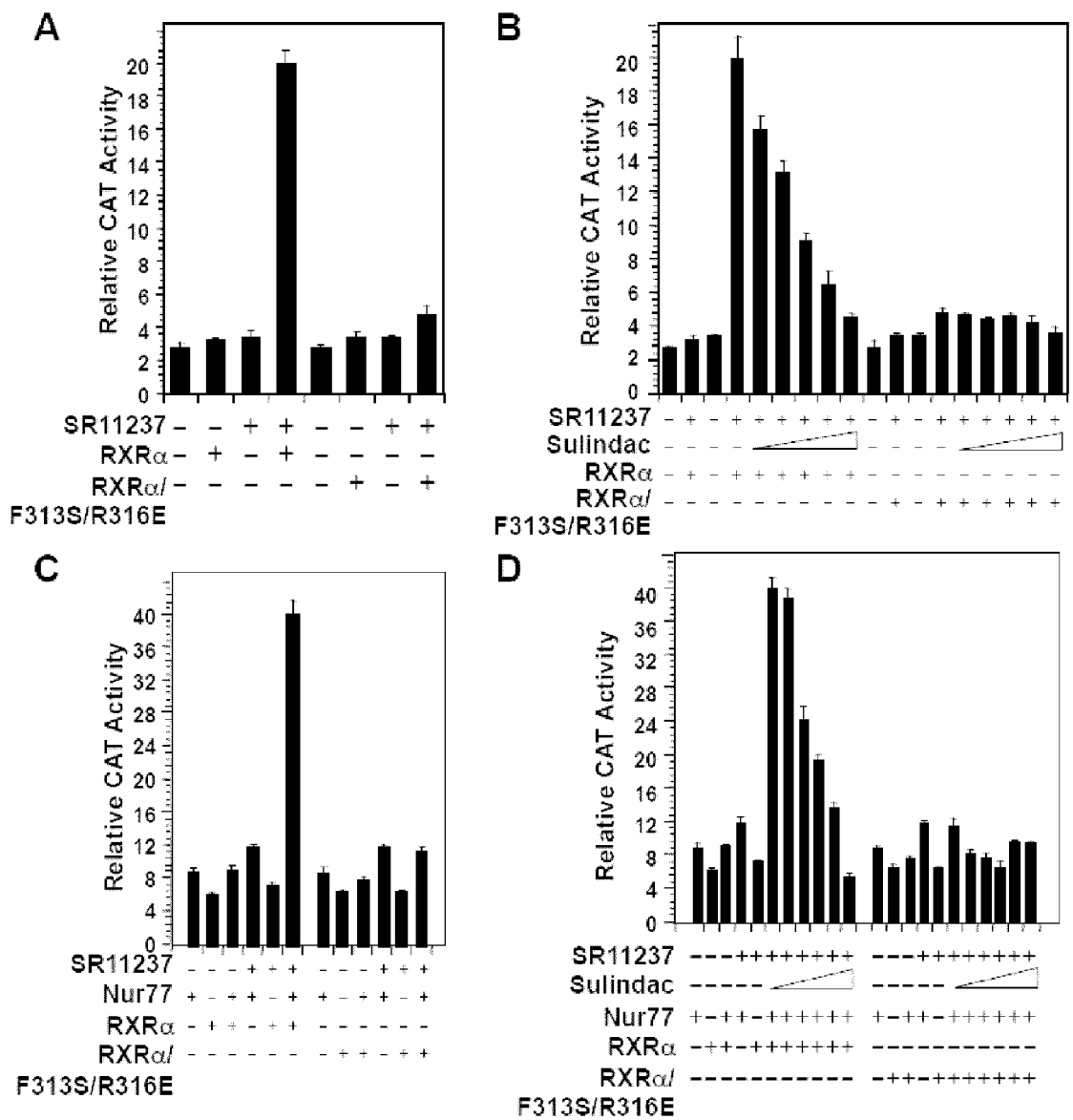
FIGS. 11A-D are related to FIG. 2G and show an impaired ability of RXRα mutant, RXR/F313S/R316E to mediate the apoptotic effect of Sulindac.

CV-1 cells were transfected with GFP-RXRα (FIG. 2F) or GFP-RXRα/F313S/R316E (FIG. 2G), treated with Sulindac (75 μM) for 24 hr, and analyzed by DAPI staining. GFP-RXRα-transfected cells underwent extensive nuclear fragmentation and condensation (FIG. 2F). Apoptosis was scored in receptor-transfected cells (FIGS. 2G and 11). Disruption of RXRα ligand-binding pocket impaired its homodimer transactivation (FIGS. 11A and 11B). Further, disruption of RXRα ligand-binding pocket impaired its heterodimer transactivation (FIGS. 11C, 11D). RXRα (20 ng), RXRα/F313S/R316E (20 ng), β-galactosidase (100 ng), and/or Nur77 (100 ng) expression vectors were transiently transfected together with (TREpal)2-tk-CAT (100 ng) (FIGS. 11A, 11B) or βRARE-tk-CAT (100 ng) (FIGS. 11C,D) into CV-1 cells. Cells were treated with or without SR11237 ($10^{-6}$ M) in the presence or absence of increasing concentrations of Sulindac (10, 37.5 75, 150 300 μM). CAT activity was determined.

Sulindac induced extensive apoptosis in F9 cells, while it had little effect in F9-RXRα−/− cells (FIGS. 2A-2C). The apoptotic effect of Sulindac was also reduced in cells transfected with RXRα siRNA (FIG. 2E), whereas transfection of RXRα enhanced its death effect (FIGS. 2F, G). RXRα/F313S/R316E failed to respond to ligandinduced homodimer or heterodimer transactivation (FIG. 11) and showed reduced apoptotic responses to Sulindac (FIG. 2G). Thus, RXRα was found to be involved in Sulindac-induced apoptosis.

HCT116 cells or HCT116 cells lacking Bax (Bax−/−) were treated with or without Sulindac (75 μM) for 24 hr. Apoptosis was determined by PARP cleavage (FIG. 2H) and DAPI staining (FIG. 2I). HCT116 cells transfected with or without RXRα siRNA or control siRNA for 48 hr were treated with Sulindac for 6 hr, and analyzed for Bax oligomerization (FIG. 2J) and Bax conformational change and mitochondrial targeting by immunostaining/confocal microscopy using Bax/Δ21, Bax/6A7, or anti-Hsp60 antibody (FIG. 2K). About 60% of cells showed BAX conformational change.

Sulindac induced cleavage of PARP (FIG. 2H) and apoptosis (FIG. 2I) in HCT116 colon cancer cells, but not HCT116 cells lacking Bax (Bax−/−). The fact that HCT116 cells are deficient of COX-2 demonstrated that Sulindac-induced apoptosis can be COX-2-independent. Immunoblotting assays showed that Bax underwent extensive oligomerization on mitochondria, which was abrogated by RXRα siRNA (FIG. 2J). In addition, immunostaining using anti-Bax antibody (Bax/Δ21) and a Bax conformation sensitive antibody Bax/6A7 (Nechushtan et al., *Biochem Biophys Res Commun* 254, 388-394 (1999)) demonstrated that Sulindac induced Bax conformational change and mitochondrial targeting were impaired by RXRα siRNA (FIG. 2K). Together, these results demonstrate that RXRα can act as an intracellular target mediating the apoptotic effect of Sulindac.

Example 3

RXRα Mutant

To address the role of Sulindac binding to RXRα, a RXRα mutant (RXRα/F313S/R316E) was constructed in which amino acids essential for maintaining the functional integrity of RXRα ligand-binding-pocket (LBP) (Bourguet, W. et al., *Mol Cell* 5 (2), 289-298 (2000)) were altered.

Flag-p85α was constructed by polymerase chain reaction (PCR) using forward primer, 5'-ccggaattccatgagtgctgagggg-tacc-3' (SEQ ID NO:1) and the reverse primer, 5'-acgcgtc-gactcatcgcctctgctgtgcat-3' (SEQ ID NO:2). PCR product was digested with Eco RI and Sal I and cloned into pCMV-Flag vector. RXRα mutants were constructed using the QUIKCHANGE® mutagenesis kit (Stratagene, La Jolla, Calif.) with the following oligonucleotides as primers: RXRα/F313S/R316E, 5'-GGAACGAGCTGCTGATCGC-CTCCTCCTCCCACGAGTCCATAGCTGT-GAAAGATGGG (forward—SEQ ID NO: 3) and 5'-CCCATCTTTCACAGCTATGGACTCGTGGGAG-GAGGAGGCGATCAGCAGCTCGTTCC (reverse—SEQ ID NO: 4); RXRα/Δ80, 5'-CCGGAATTCGGaccacacccac-cctgggc-3' (forward—SEQ ID NO: 5) and 5'-CCGCTC-GAGctaagtcatttggtgcggcg-3' (reverse—SEQ ID NO: 6); and RXRα/Δ100, 5'-CCGGAATTCGGgtcagcagcagcgaggac-3' (forward—SEQ ID NO:5) and 5'-CCGCTCGAGctaagt-catttggtgcggcg-3' (reverse—SEQ ID NO:6). PCR products were digested with EcoR I and Xho I, and ligated into pCMV-Myc vector.

RXRα (20 ng), RXRα/F313S/R316E (20 ng), β-galactosidase (100 ng), and/or Nur77 (100 ng) expression vectors were transiently transfected together with (TREpal) 2-tk-CAT (100 ng) (FIG. 11A) or βRARE-tk-CAT (100 ng) (FIG. 11B) into CV-1 cells. Cells were treated with or without SR11237 ($10^{-6}$ M). CAT activity was determined.

The mutant failed to respond to ligand-induced transactivation (FIG. 11) and showed reduced responses to Sulindac (FIG. 2G) (see Example 2).

Example 4

Inhibition of AKT Activation by Sulindac

The inhibition of AKT (a key protein responsible for cancer cell survival) activation by Sulindac was investigated.

Figure 3:
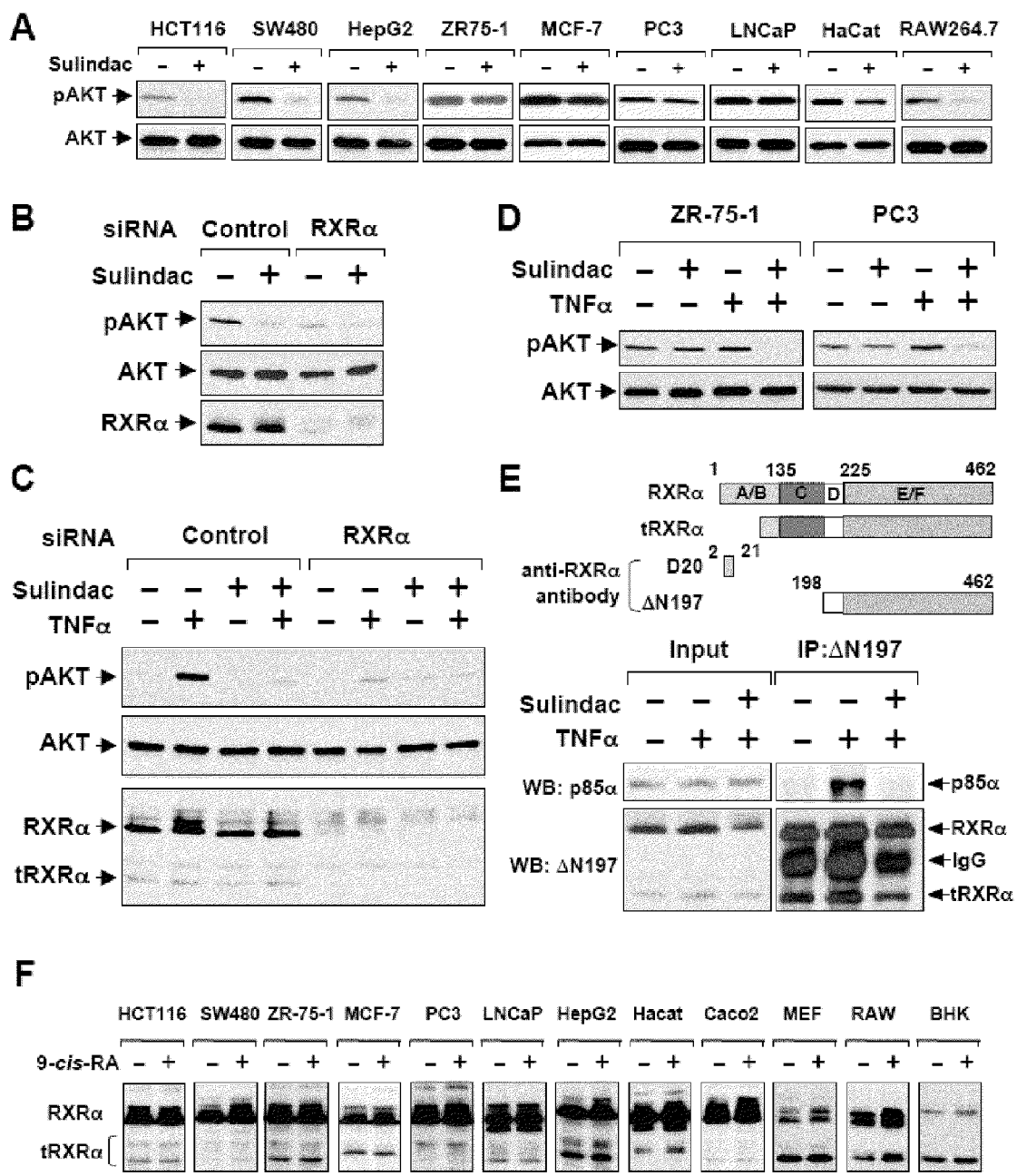
FIG. 3 shows Sulindac inhibiting TNFα-induced AKT activation and tRXRα-p85α interaction. (a) Inhibition of AKT activation by Sulindac. HCT116, SW480, HepG2, ZR75-1, MCF-7, PC3, LNCaP, HaCat, and RAW264.7 cells starved overnight and treated with Sulindac were analyzed for AKT activation by immunoblotting. (b) Inhibition of basal AKT activation by RXRα siRNA. HepG2 cells transfected with RXRα siRNA were treated with Sulindac. AKT activation and RXRα expression were analyzed by immunoblotting. (c) Inhibition of TNFα-induced AKT activation by Sulindac and RXRα siRNA. A549 lung cancer cells transfected with RXRα or control siRNA were pretreated with Sulindac and exposed to TNFα. AKT activation and RXRα expression were analyzed by immunoblotting. (d) Synergistic inhibition of AKT activation by TNFα and Sulindac. ZR-75-1 and PC3 cells were pretreated with Sulindac and exposed to TNFα. AKT activation was analyzed by immunoblotting. (e) Schematic representation of anti-RXRα antibodies used in co-immunoprecipitation and immunoblotting assays (above). D20 antibody recognized amino acids 2-21 in the N-terminal A/B domain, while ΔN197 antibody recognizes the C-terminal E/F domain (below). A RXR truncated protein with about 44 kDa is also shown. (f) Expression of tRXRα in various cancer cell lines. HCT116, SW480, ZR75-1, MCF-7, PC3, LNCaP, HepG2, HaCat, Caco2, MEF, RAW, and BHK cell lines treated with or without 9-cis-RA were analyzed by immunoblotting using the ΔN197 RXRα antibody.

HepG2, SW480, RAW264.7, HCT116, LNCaP, PC3, ZR-75-1, and HaCat cells were starved overnight and treated with Sulindac (100 μM) for 1 hr and analyzed for AKT activation by immunoblotting (FIG. 3A). HepG2 cells were also transfected with RXRα siRNA for 48 hours, treated with Sulindac (100 μM) for 1 hour, and analyzed for AKT activation and RXRα expression by immunoblotting (FIG. 3B).

Figure 12:
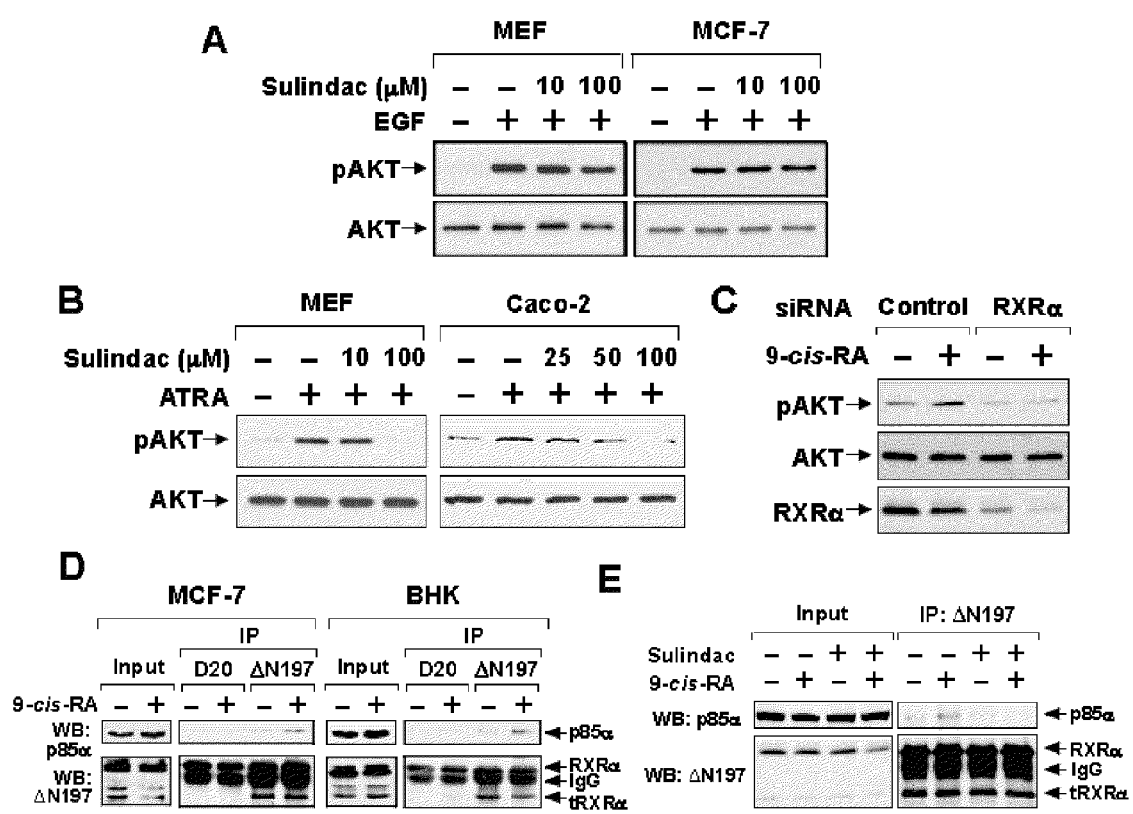
FIG. 12A-E are related to FIG. 3 and show that the inhibitory effect of Sulindac on AKT activation and tRXRα-p85α interaction.

MEF and MCF-7 cells were starved overnight, pretreated with Sulindac for 1 hr, and stimulated with EGF (100 ng/ml) for 15 min. AKT activation was analyzed by immunoblotting (FIG. 12A). MEF and Caco-2 cells were starved overnight and pretreated with Sulindac for 30 min before exposure to all-trans-retinoic acid (ATRA) ($10^{-7}$ M) for 30 min and analyzed for AKT activation (FIG. 12B). AKT activation in ZR-75-1 breast cancer cells transfected with RXRα siRNA for 48 hr before exposure to 9-cis-RA ($10^{-7}$ M) for 30 min was also analyzed by immunoblotting (FIG. 13C). A549 lung cancer cells transfected with RXRα or control siRNA (FIG. 3C) and ZR-75-1 and PC3 cells (FIG. 3D) were pretreated with Sulindac (100 μM) for 1 hr before exposure to TNFα (10 ng/ml) for 30 min and analyzed for AKT activation and RXRα expression by immunoblotting.

Significant inhibition of basal AKT activation by Sulindac was observed in various cancer cells lines, including COX-2-negative SW480 and HCT116 colon cancer cells (FIG. 3A), suggesting a COX-2-independent mechanism. Sulindac failed to inhibit AKT activation by EGF, but potently inhibited AKT activation by retinoic acid. Transfection of RXRα siRNA significantly reduced the constitutive AKT activation (FIG. 3B), similar to the effect of Sulindac. Treatment of cells with all-trans-RA (ATRA) for 30 min strongly induced AKT activation, which was inhibited by Sulindac in a dose dependent manner (FIG. 12B) and by RXRα siRNA (FIG. 12C). Although Sulindac failed to inhibit AKT activation induced by epidermal growth factor (FIG. 12A), it potently inhibited AKT activation induced by retinoic acid in a RXRα-dependent manner (FIGS. 12B,C). Thus, Sulindac can interfere with RA-induced rapid RXRα-dependent AKT activation.

Sulindac was examined for suppression of TNFα induced AKT activation. TNFα strongly activated AKT in A549 lung cancer cells, which was potently inhibited by Sulindac and RXRα siRNA (FIG. 3C), suggesting that TNFα activation of AKT was RXRα-dependent. Although TNFα failed to activate AKT in cells with high basal AKT activation (such as ZR-75-1 and PC3 cells) and Sulindac showed little inhibitory effect on AKT activation in these cells, a Sulindac combination with TNFα synergistically, and almost completely, inhibited AKT activation (FIG. 3D). Thus, TNFα is able to sensitize cancer cells to AKT inhibition by Sulindac, suggesting that TNFα can prime cancer cells for their responsiveness to Sulindac, possibly by converting AKT activation from a RXRα-independent to RXRα-dependent manner.

MCF-7 and baby hamster kidney (BHK) cells treated with 9-cis-RA ($10^{-7}$ M) for 30 min were analyzed for RXRα-p85α interaction by co-immunoprecipitation using D20 or ΔN197 anti-RXRα antibody (FIG. 12D). H292 lung cancer cells treated with 9-cis-RA and/or Sulindac (100 μM) for 30 min were analyzed for RXRα-p85α interaction by co-immunoprecipitation using ΔN197 antibody (FIG. 12E). Sulindac failed to inhibit AKT activation by EGF, but potently inhibited AKT activation by retinoic acid. Further, 9-cis-retinoic acid promoted tRXRα interaction with p85α when ΔN197 anti-RXRα, but not D20 anti-RXRα antibody, was used.

Example 5

Interaction of p85α with tRXRα and RXRα

RXRα interaction with p85α was examined. Anti-RXRα antibodies (Santa Cruz Biotechnology, Santa Cruz, Calif.) were used in co-immunoprecipitation (Co-IP) and Western blotting (WB) assays. BHK cells were treated with ATRA ($10^{-7}$ M) for 30 min. Lysates were prepared and analyzed for RXRα-p85α interaction using either D20 anti-RXRα or ΔN197 anti-RXRα antibody (FIG. 12D).

An initial attempt using anti-RXRα antibody against sequences in the NH2 terminus of RXRα (D20) by co-immunoprecipitation assays failed to detect clear interaction, although the antibody effectively immunoprecipitated the RXRα protein. However, when another anti-RXRα antibody against the COOH-terminal ligand-binding domain (LBD) of RXRα (ΔN197) was used, p85α was readily co-immunoprecipitated in a TNFα (FIG. 3E) or RA-dependent manner (FIGS. 12D,E). D20 anti-RXRα antibody recognized amino acids 2-21 in the N-terminal A/B domain, while ΔN197 anti-RXRα antibody recognized the C-terminal E/F domain (FIG. 3E). Co-immunoprecipitation of p85α by the ΔN197 anti-RXRα antibody was accompanied by immunoprecipitation of a truncated RXRα (tRXRα), which was not detected by D20 RXRα antibody, indicating its lack of N-terminal sequences (FIG. 12D). Using the ΔN197 anti-RXRα antibody, interaction of p85α with tRXRα and/or RXRα was enhanced by TNFα and inhibited by Sulindac (FIG. 3E). Interaction of p85α with tRXRα in the presence of TNFα was also inhibited by Sulindac (FIG. 12E). These results suggest that tRXRα binds to p85α, leading to AKT activation.

Example 6

Amino Acids 80 to 100 of RXRα are Critical for Binding to p85α

Intracellular proteolytic cleavage was examined. Cells were treated with or without 9-cis-RA ($10^{-7}$ M) for 30 min and lysates were analyzed by immunoblotting using the ΔN197 RXRα antibody (FIG. 3F). The immunoblots demonstrated that RXRα is often cleaved at its amino terminus in different cellular contexts and biological processes (FIG. 3F).

Figure 13:
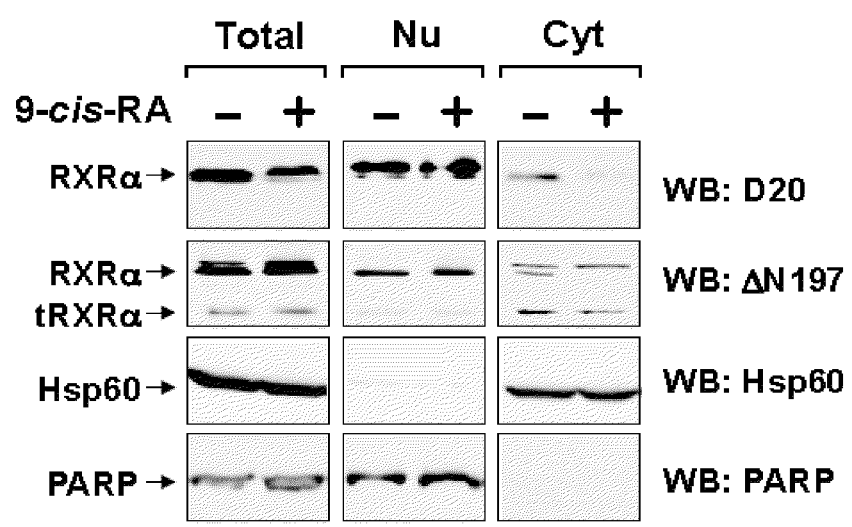
FIG. 13 is related to FIGS. 4B and 5D and shows the cytoplasmic localization of tRXRα using cellular fractionation assays.

A549 lung cancer cells were also treated with or without 9-cis-RA for 30 min. Nuclear (Nu) and cytoplasmic (Cyt) fractions were analyzed by immunoblotting using D20 or ΔN197 anti-RXRα antibody. To ensure the purity of preparations, fractions were also immunoblotted for the presence of Hsp60 (cytoplasmic specific) and PARP (nuclear specific) proteins (FIG. 13). Subcellular localization of endogenous RXRα in MEFs was visualized by confocal microscopy after immunostaining using anti-RXRα (ΔN197). Cells were also stained with DAPI to visualize the nucleus (FIG. 4B).

Figure 4:
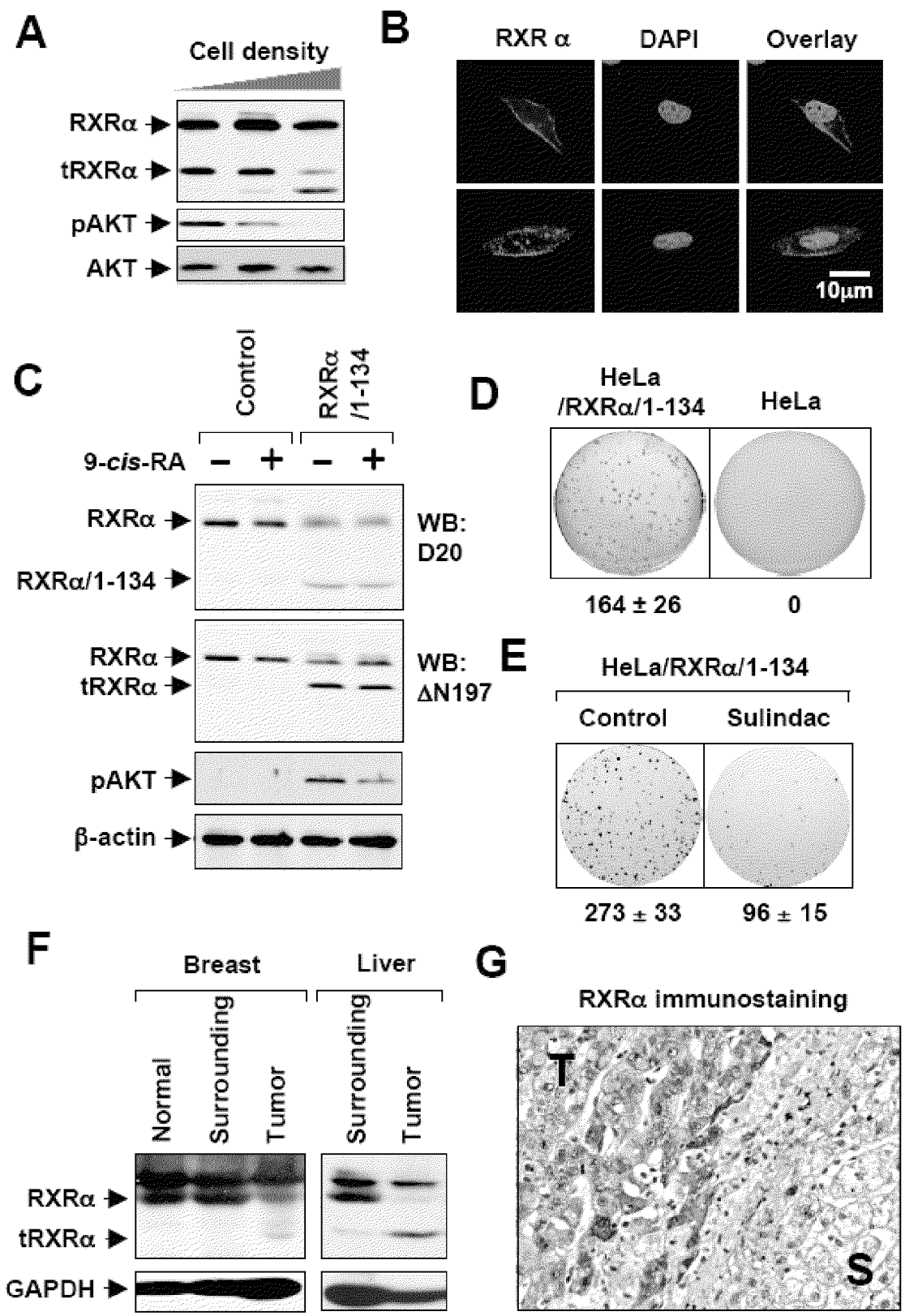
FIG. 4 shows the role of tRXRα in AKT activation and anchorage-independent cell growth. (a) Cell density-dependent production of tRXRα and AKT activation. MEFs seeded at different cell densities were analyzed for RXRα expression using ΔN197 antibody and for AKT activation by immunoblotting. (b) Subcellular localization of endogenous RXRα in MEFs was visualized by confocal microscopy after immunostaining using anti-RXRα (ΔN197). Cells were also stained with DAPI to visualize the nucleus. (c) Stable expression of RXRα/1-134 induces RXRα cleavage and AKT activation. HeLa or HeLa cells stably expressing RXRα/1-134 were treated with 9 cis-RA and analyzed for AKT activation and expression of RXRα. (d) Growth of HeLa/RXRα/1-134 and HeLa cells in soft agar. (e) Sulindac inhibits clonogenic survival of HeLa/RXRα/1-134 cells. (f) Production of tRXRα in human tumor tissues of breast (5 out of 6) or liver (4 out of 6) compared to tumor surrounding and normal tissues. (g) Cytoplasmic localization of RXRα in liver tumor specimens immunostained by ΔN197 antibody. T: tumor tissue; S: tumor surrounding tissue.

RXRα was found at the plasma membrane (FIG. 4A, top panel) and displayed punctate structure on cell membrane in some cells (FIG. 4A, bottom panel). The production of a 44-kDa tRXRα in MEFs was also regulated by cell density (FIG. 4A). Level of the 44-kDa tRXRα observed in cells cultured at low density was reduced when cells were grown at high density, which was accompanied with appearance of a smaller RXRα fragment. Interestingly, the levels of the 44-kDa tRXRα protein correlated with AKT activation (FIG. 4A), suggesting that cell density-dependent proteolytic cleavage of RXRα might be an important mechanism regulating AKT activation. Consistent with cytoplasmic localization of tRXRα (FIG. 13), RXRα was mainly found in the cytoplasm when MEF cells were immunostained by the ΔN197 anti-RXRα antibody (FIG. 4B). Thus, deletion of the very N-terminal end sequences of RXRα could alter its subcellular localization, conferring its ability to interact with p85α. Observations that p85α was co-immunoprecipitated with tRXRα as described herein suggest that tRXRα might bind to p85α, leading to tRXRα-dependent AKT activation.

MEF cells were seeded at different cell densities and lysates were prepared and analyzed for AKT activation by immunoblotting. Lysates were also examined by immunoblotting using ΔN197 anti-RXRα antibody (FIG. 4A). Levels of tRXRα in mouse embryonic fibroblasts (MEFs) correlated with AKT activation in a cell density-dependent manner (FIG. 4A). Consistent with the cytoplasmic localization of tRXRα, MEFs often displayed plasma membrane localization of RXRα (FIG. 4B).

Figure 5:
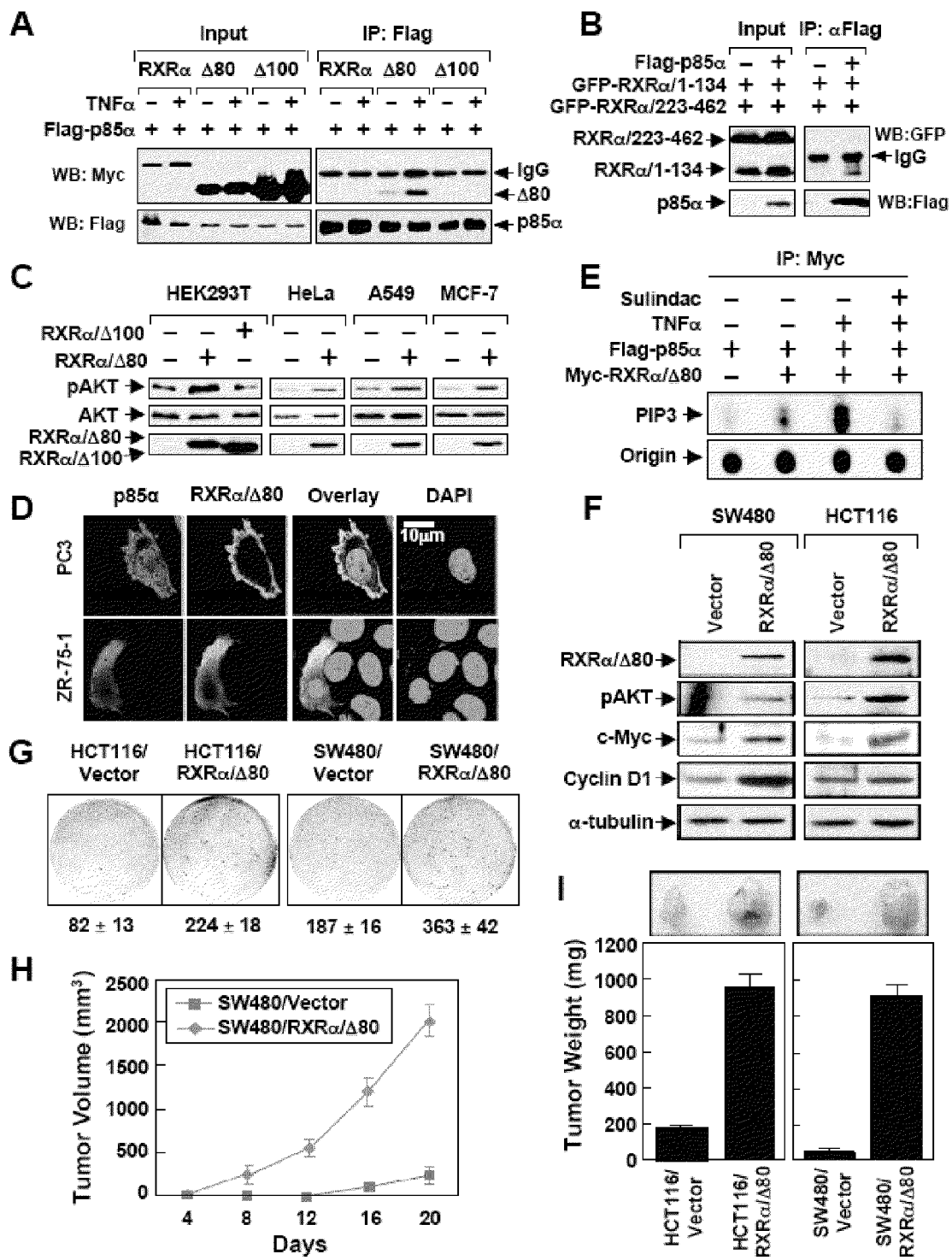
FIG. 5 shows the role of N-terminally truncated RXRα in PI3K/AKT activation by TNFα and cancer cell growth. (a) HEK293T cells were transfected with Flag-p85α and RXRα, RXRα/Δ80, or RXRα/Δ100 tagged with the Myc epitope, treated with TNFα, and analyzed for by co-immunoprecipitation using anti-Flag antibody. (b) N-terminal A/B domain of RXRα interacts with p85α. Flag-p85α was cotransfected with GFP-RXRα-1-134 and GFP-RXRα-224-462 into HEK293T cells, and analyzed for their interaction by co-immunoprecipitation using anti-Flag antibody. (c) RXRα/Δ80 is a potent AKT activator. AKT activation of HEK293T, HeLa, A549, and MCF-7 cells transfected with RXRα/Δ80 or RXRα/Δ100 as determined by immunoblotting. (d) Cytoplasmic co-localization of RXRα/Δ80 and p85α. Myc-RXRα/Δ80 and p85α were cotransfected into PC3 and ZR-75-1 cell lines, immunostained with anti-Myc and anti-p85α antibody, and their subcellular localization revealed by confocal microscopy. (e) Activation of PI3K by RXRα/Δ80 immunoprecipitates. A549 cells transfected with Flag-p85α and Myc-RXRα/Δ80 were treated with TNFα and/or Sulindac, immunoprecipitated with anti-Myc antibody, and subjected to an in vitro PI3K assay. (f) Stable expression of RXRα/Δ80. Cells stably transfected with GFP-RXRα/Δ80 or control GFP vector were analyzed by immunoblotting. (g) RXRα/Δ80 promotes clonogenic survival of cancer cells. (h,i) RXRα/Δ80 promotes cancer cell growth in nude mice.

To directly address the role of tRXRα in p85α interaction and AKT activation, a RXRα mutant lacking its N-terminal 80 amino acids (RXRα/Δ80) was constructed, which produced a RXRα mutant protein with a molecular weight similar to the endogenous tRXRα. When Myc-tagged RXRα/Δ80 was cotransfected with Flag-p85α into cells, they interacted strongly, which was further enhanced by TNFα (FIG. 5A). In contrast, the full-length RXRα or RXRα mutant lacking 100 N-terminal amino acids (RXRα/Δ100) failed to interact with Flag-p85α under the same conditions. Thus, amino acids 80 to 100 of RXRα are critical for binding to p85α. In support of this, the RXRα N-terminal A/B domain (RXRα/1-134), but not its LBD (RXRα/224-462), interacted with p85α (FIG. 5B). Consistent with cytoplasmic localization of tRXRα (FIG. 13) RXRα/Δ80 predominantly resided in the cytoplasm, displaying diffused and sometimes punctate plasma membrane localization (FIG. 5D). Transfection of RXRα/Δ80, but not RXRα/Δ100, also strongly activated AKT in various cell types (FIG. 5C).

The RXRα/Δ80 immunocomplex was examined for PI3K activity in vitro. Myc-tagged RXRα/Δ80 and p85α were cotransfected into A549 cells, and the Myc-RXRα/Δ80- containing complex was immunoprecipitated by anti-Myc antibody and assayed for PI3K activity. Specific Myc-RXRα/Δ80 immunoprecipitates prepared from cells exhibited strong PI3K activity in a TNFα-dependent manner (FIGS. 5E and 15), which correlated well with its ability to interact with p85α (FIG. 5A) and activation of AKT (FIG. 5C). Thus, TNFα-induced tRXRα/p85α interaction was found to activate PI3K/AKT signaling.

RXRα/Δ80 was stably expressed in SW480 and HCT116 colon cancer cells, and the resulting stable clones, SW480/RXRα/Δ80 and HCT116/RXRα/Δ80, showed elevated AKT activation and induction of its downstream targets c-Myc and cyclin D1 (FIG. 5F). Clonogenic survival assays were used to evaluate the growth of SW480/RXRα/Δ80 and HCT116/RXRα/Δ80. The stable clones formed much more colonies than the control cells (FIG. 5G). The effect of RXRα/Δ80 on the growth of cancer cells was examined in animals. To this end, the same number of RXRα/Δ80-expressing cells or control cells were injected into different flanks of same nude mice and their growth was determined. Tumors formed by SW480/RXRα/Δ80 and HCT116/RXRα/Δ80 grew much faster than those formed by the control cells in animals (FIGS. 5H-I). Together, these results demonstrate that the N-terminally truncated RXRα is a potent promoter of cancer cell growth in vivo.

Example 7

Endogenous tRXRα in AKT Activation and Cell Transformation

Figure 8:
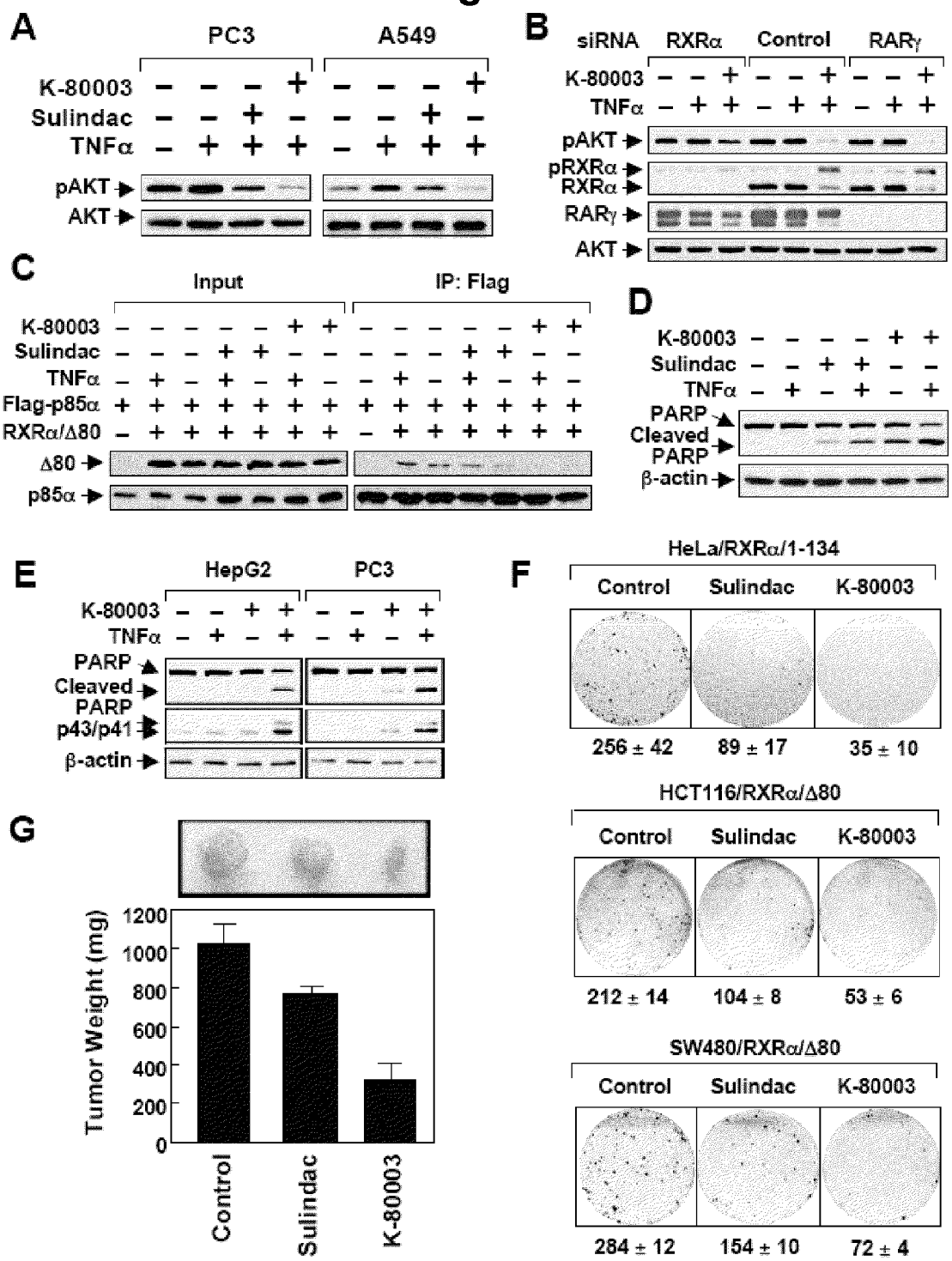
FIG. 8 shows that K-80003 is a potent inhibitor of RXRα-dependent AKT activation. (a) Inhibition of AKT activation by Sulindac or K-80003 in the presence of TNFα. (b) RXRα-dependent inhibition of AKT activation by K-80003. PC3 cells transfected with RXRα or RARγ siRNA were pre-treated with K-80003 before exposure to TNFα (pRXRα: phosphorylated RXRα). (c) Inhibition of RXRα/Δ80 interaction with p85α by Sulindac and K-80003. A549 cells were transfected with Flag-p85α and Myc-RXRα/Δ80, treated with Sulindac or K-80003 before exposure to TNFα, and analyzed by coimmunoprecipitation using anti-Flag antibody. (d) Induction of PARP cleavage by Sulindac or K-80003 in the presence of TNFα. ZR-75-1 cells treated with TNFα and/or Sulindac or K-80003 were analyzed by immunoblotting. (e) Activation of caspase-8 by K-80003 in the presence of TNFα. Cells treated with TNFα and/or K-80003 were analyzed by immunoblotting. (f) Inhibition of clonogenic survival of RXRα/1-134 cells and RXRα/Δ80 stable clones by Sulindac and K-80003. (g) Inhibition of RXRα/Δ80 tumor growth in animals by Sulindac and K-80003.

The observation that full-length RXRα failed to interact with p85α suggested that the p85α-binding motif in the A/B domain is masked in RXRα. Thus, the N-terminal A/B domain of RXRα could interact with the full-length RXRα (Supp. FIG. 8a), revealing an intramolecular interaction.

Expression vectors GFP-RXRα/1-134 and Myc-RXRα were transfected into HEK293T cells. Interaction was analyzed by Co-IP using anti-Myc antibody (Supp. FIG. 8a). The full-length RXRα or RXRα/1-134 fused with GFP at its N-terminal end and the full-length RXRα tagged with the Myc epitope at its C-terminal end were cotransfected into HEK293T cells. Thirty-six hrs later, cell lysates were analyzed by IP and WB with an anti-Myc antibody.

The N-terminal A/B domain bound to RXRα (Supp. FIG. 8a). Expression of RXRα N-terminal fragment induced RXRα cleavage (Supp. FIG. 8b). Transfection of RXRα/1-134 together with the full-length RXRα enhanced levels of tRXRα (Supp. FIG. 8b), likely due to its disruption of the intramolecular interaction by competition, resulted in the exposure of proteolytic sites in the RXRα N-terminus.

Figure 14:
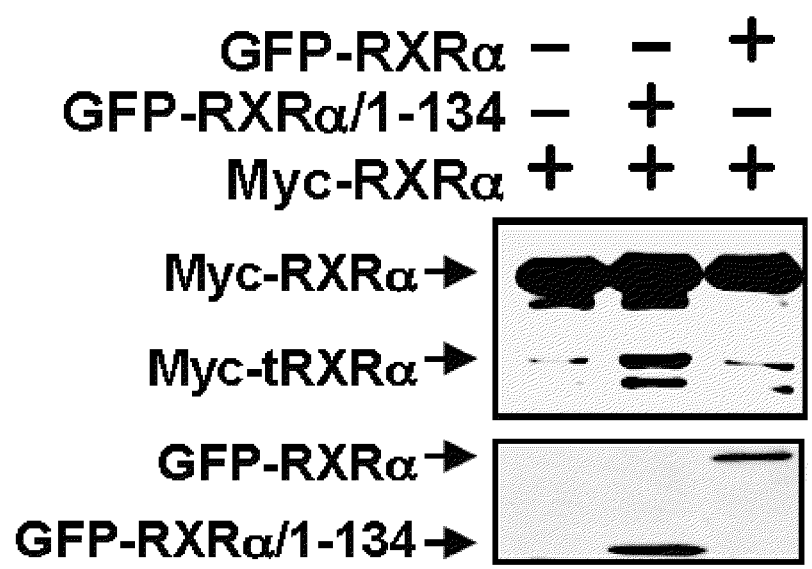
FIG. 14 is related to FIG. 4 and shows the production of endogenous tRXRα by stable expression of RXRα/1-134.

Transfection of the N-terminal region of RXRα, RXRα/1-134, could enhance the tRXRα level (FIG. 14). To study the role of endogenous tRXRα, RXRα/1-134 was stably expressed in HeLa cells, and significantly increased tRXRα protein in cells stably expressing RXRα/1-134, which was accompanied by a decrease in endogenous full-length RXRα protein (FIG. 4C). Compared to parental HeLa cells, the HeLa/RXRα/1-134 stable clone had higher AKT activation (FIG. 4C) and grew rapidly in soft agar (FIG. 4D), suggesting a role for endogenous tRXRα in AKT activation and cell transforming activity. In the colony formation assay, Sulindac strongly inhibited colonies formed by the stable clone (FIG. 4E). The clinical relevance of tRXRα was illustrated by the presence of tRXRα in tumor tissues from breast cancer patients, but not in the corresponding tumor surrounding tissues and normal tissues (FIG. 4F). Similar results were obtained in liver cancer patients. Immunohistochemical analysis of RXRα in human liver cancer specimens revealed strong cytoplasmic RXRα staining in tumor tissue, but not in the corresponding tumor surrounding tissue (FIG. 4G). Together, these results demonstrate that tRXRα may contribute to the growth and survival of cancer cells by activating AKT, and that tRXRα-mediated activities can be negatively regulated by Sulindac.

Example 8

Synthesis of Sulindac Analogs

Figure 18:
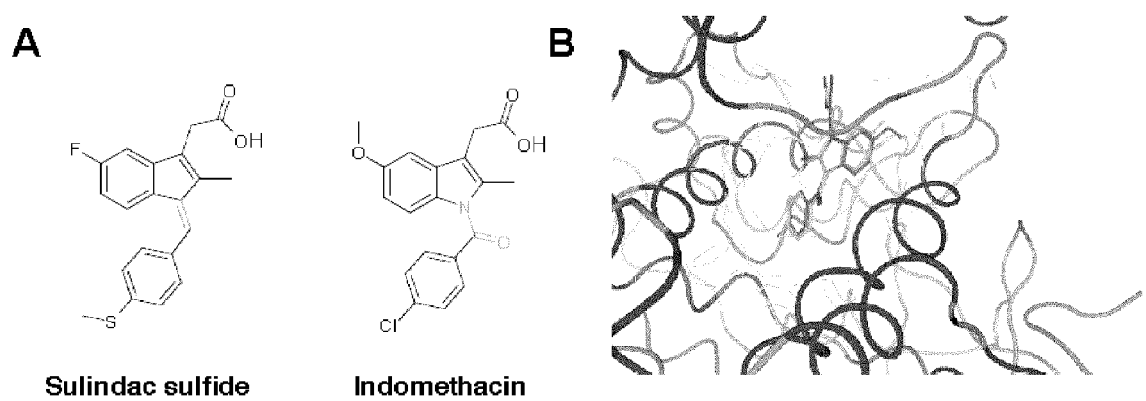
FIGS. 18A-B are related to FIG. 7 and show the design of some of the RXRα-selective Sulindac analogs described herein.

The finding that RXRα served as an intracellular target of Sulindac action provided an opportunity to identify RXRα-selective Sulindac derivatives for suppressing AKT activity. The binding of Sulindac to RXRα and COX-2 (FIGS. 7A, 18B) was compared to design Sulindac analogs, which favor RXRα binding, but disfavor COX-binding. Two dimensional structures of sulindac sulfide and indomethacin were compared (FIG. 18A). An overlay of Sulindac and indomethacin bound in the active site of COX-2 was generated (FIG. 18B). Sulindac was intuitively modeled to bind to COX-2 similar to indomethacin.

Figure 19:
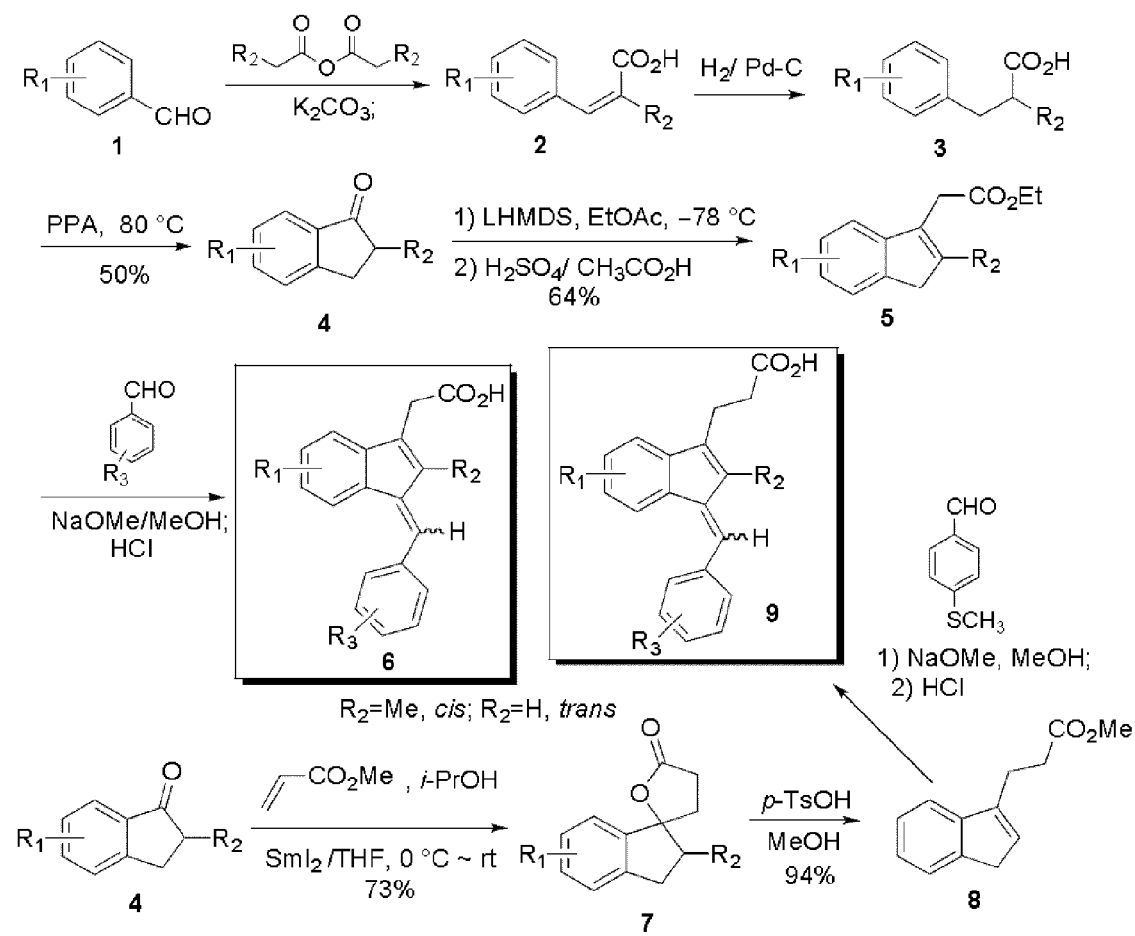
FIG. 19 is related to FIG. 8 and shows a synthesis of Sulindac analog K-80003.

Analogs were designed and synthesized (FIG. 19). Substituted indanone derivatives (4) were prepared using substituted benzaldehyde (1) as starting material. In a Perkin-reaction, derivative (1) was treated with appropriate anhydride to give derivative (2), which was then reduced by catalytic hydrogenation to give derivative (3). A polyphosphoric acid (PPA)-catalyzed intramolecular Friedel-Crafts acylation closed the 5-membered ring to give the 1-indanone derivative (4). Treatment of derivative (4) with the enolate generated from ethyl acetate and lithium hexamethyldisilylamide (LHMDS), followed by dehydration under acidic conditions gave the desired acetate (5). The produced indene-3-acetate (5) reacted with substituted benzaldehyde (Claisen-Schmidt-reaction) to give, after acidification, the Sulindac analogs (Z-6). One step for the synthesis of Sulindac analogs (9) is the samarium diiodide ($SmI_2$)-mediated reductive coupling of 1-indanone derivative (4) with methyl acrylate, which gave spirolactone (7). Treatment of a methanolic solution of (7) with a catalytic amount of para-toluenesulfonic acid (p-TsOH) yielded the dehydrated product (8), which was subjected to Claisen-Schmidt-reaction and acidification to give Sulindac analogs (9). Noteworthy is that, in the Claisen-Schmidt-reactions of compounds (5/8), when $R_2=CH_3$, cis (Z)-isomers of compounds (6/9) formed predominantly; while in the case of $R_2=H$, trans (E)-isomers of compounds (6/9) formed predominantly.

Example 9

Evaluation of Sulindac Analogs

Figure 7:
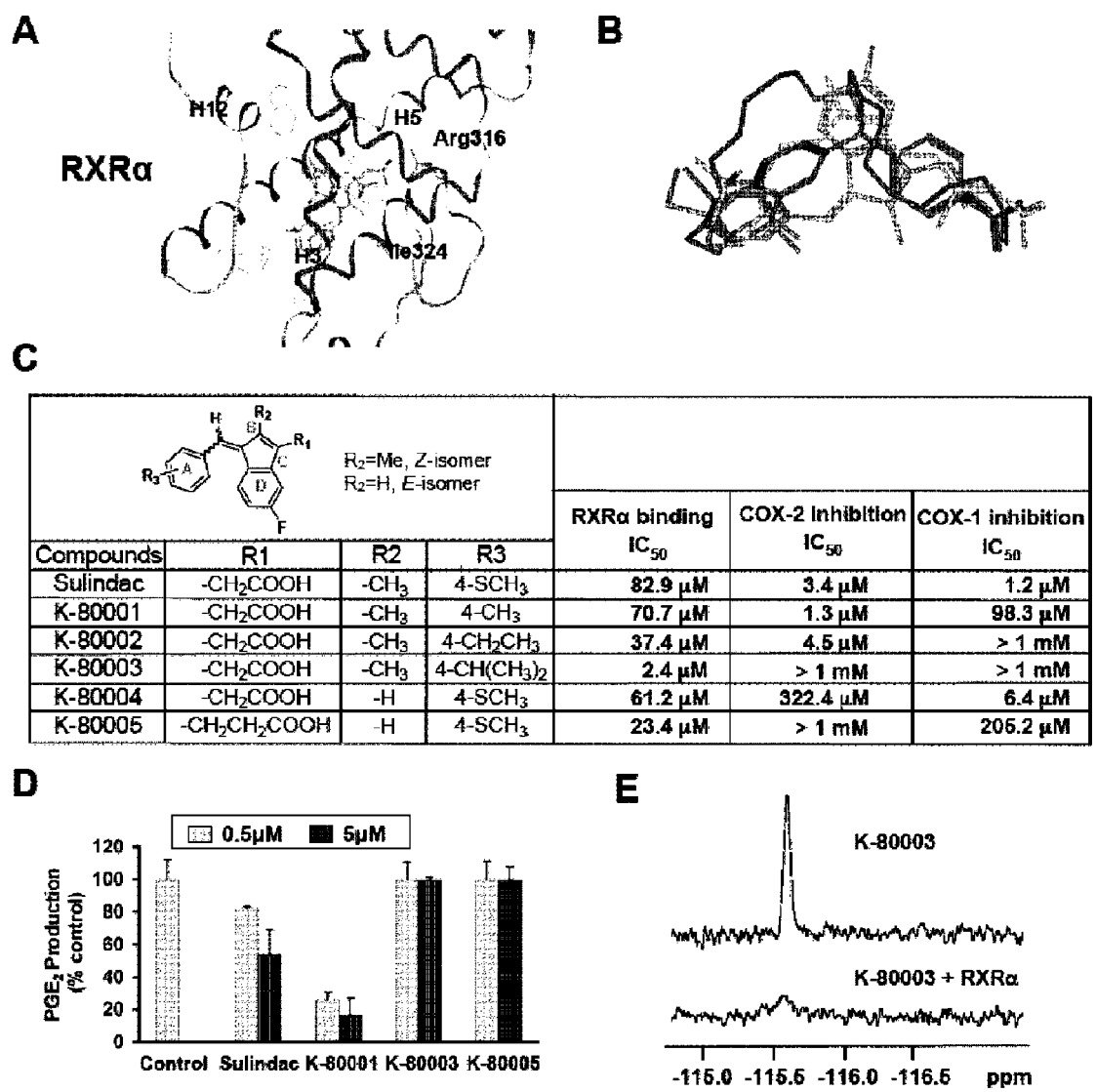
FIG. 7 shows the design, synthesis, and evaluation of RXRα-selective Sulindac analogs. (a) Docking of sulindac sulfide to the LBP of RXRα in reference to 9-cis-RA. Side chains within 4 Å of the ligands are displayed in grey. (b) Comparison of orientation and position of docked sulindac sulfide to the crystal structures of 9-cis-RA, DHA, and BMS649. (c) RXRα binding and inhibition of COX-1 and COX-2 activities by Sulindac analogs. RXRα binding was measured by competition ligand-binding assays. (d) Inhibition of PGE2 production by Sulindac and analogs. A549 cells stimulated with TNFα were treated with Sulindac or analogs. (e) Comparison of $^{19}F$ NMR spectra of K-80003 in the absence and presence of RXRα LBD.

Docking of Sulindac to the LBP of RXRα in reference to 9-cis-RA was evaluated to identify strategies for structural modifications of Sulindac to dissociate its COX inhibition from RXRα-binding activity. The docking of Sulindac to RXRα is shown in FIG. 7A. The orientation and position of docked Sulindac was compared to the crystal structures of 9-cis-RA, DHA and BMS649 (FIG. 7B). Sulindac bound in a mode where its carboxylate group was aligned with the carboxylate group found in all RXRα ligands examined (FIG. 7B), interacting with Arg316 in the RXRα LBP. The benzyl methyl sulfide portion of Sulindac bound to the hydrophobic region of the RXRα LBP, overlapping with the a-ionone ring of 9-cis-RA. In this binding mode, Van der Waals interaction of the —SCH3 group at position 4 (FIG. 7C) with the RXRα protein was not optimal and there was space for modification to improve the binding to RXRα The idea of making use of position 4 to design RXRα-selective analogs was fully supported by the fact that sulindac prodrug, sulindac sulfoxide and the metabolite sulindac sulfone show no COX-inhibiting activity, whereas the metabolite sulindac sulfide (used herein) is a potent COX inhibitor (Haanen, 2001). As shown in FIG. 7A, the carboxylate group of Sulindac was positioned away from Arg316 compared to the equivalent ones in RXRα ligands DHA, BMS649, and 9-cis-RA. Replacing —CH2COOH at position D with a bulkier group such as —CH2CH2COOH would help place the carboxylate group closer to Arg316 to achieve good charge-charge interaction with RXRα as observed in 9-cis-RA.

Candidate compounds were also examined by docking to the crystal structure of COX-2 (FIG. 18) to identify non-COX binders. Based on these considerations, five analogs were designed and synthesized (FIGS. 7C and 19). Their evaluation showed that all analogs retained RXRα-binding activity, with K-80003 being the most potent (about 34-fold higher than Sulindac), likely due to its iso-propyl (i-Pr) group at position 4, which has improved interaction with the hydrophobic residues on Helix7 of RXRα Significantly, K-80003 and K-80005 had no detectable inhibition of COX activities (FIG. 7C) and failed to inhibit constitutive and TNFα (FIG. 7D) or IL-1β (not shown)-induced prostaglandin E2 (PGE2) production. The binding of K-80003 to RXRα was also confirmed by 19F NMR binding assays (FIG. 7E). Thus, Sulindac's RXRα-binding can be dissociated from its COX-binding.

A549 cells were seeded in 24-well plates in DMEM with 10% fetal bovine serum. After overnight culture, cells were stimulated with 10 ng/ml IL-1β in DMEM medium without serum for 24 hr. After 10 min pretreatment with the indicated concentrations of Sulindac or analog, cells were co-treated with 10 μM arachidonic acid and Sulindac or its analog for 30 min at 37° C. Medium was collected and immediately assayed. PGE2 production was measured with Prostaglandin E2 EIA Kit-Monoclonal according to the manufacturer's instructions (Cayman Chemical, Ann Arbor, Mich.). PGE2 production (%) is expressed as the ratio of PGE2 produced in the presence of compound to that with vehicle alone.

Figure 20:
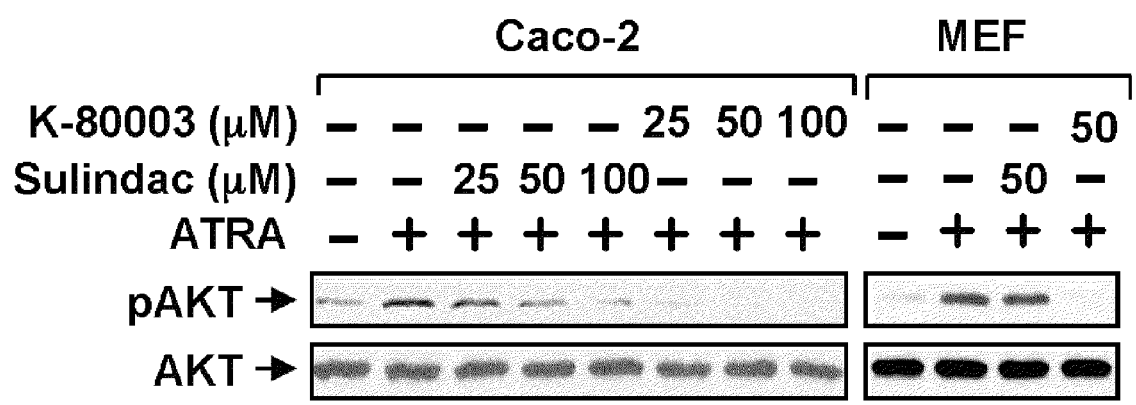
FIG. 20 is related to FIG. 8 and shows that K-80003 is more effective than Sulindac in inhibiting AKT activation by all-trans-retinoic acid.

Evaluation of the analogs showed that they all retained RXRα-binding activity, with K-80003 being the most potent (about 34-fold higher than Sulindac) (FIG. 7C), likely due to the iso-propyl (i-Pr) group at position 4, which showed improved interaction with the hydrophobic residues on Helix7 of RXRα. K-80003 and K-80005 had no detectable inhibition of COX activities (FIG. 7C) and did not inhibit constitutive or TNFα- (FIG. 7D) or IL-1β-induced prostaglandin E2 (PGE2) production (not shown). $^{19}$F NMR spectra of K-80003 (100 μM) were compared in the absence and presence of 10 μM RXRα LBD (FIG. 7E). Caco-2 and MEF cells were treated with the indicated concentration of Sulindac or K-80003 for 30 min, then stimulated with all-trans-RA ($10^{-7}$ M) for 15 min. AKT activation was analyzed by immunoblotting. PC3 cells transfected with RXRα or RARγ siRNA were pre-treated with K-80003 (50 μM) for 1 hr before exposed to TNFα (10 ng/ml) for 30 min (pRXRα: phosphorylated RXRα). A549 cells were transfected with Flag-p85α and Myc-RXRα/Δ80, treated with Sulindac (50 μM) or K-80003 (50 μM) for 1 hr, exposed to TNFα for 30 min, and analyzed by coimmunoprecipitation using an anti-Flag antibody. K-80003 (50 μM) was much more effective than Sulindac (50 μM) in inhibiting ATRA-induced AKT activation (FIG. 20), and TNFα-induced AKT activation (FIG. 8A), the colony formation of a HeLa/RXRα/1-134 stable clone (FIG. 8B), and the interaction of p85α with RXRα/Δ80 (FIG. 8C). Reducing RXRα expression by siRNA largely impaired the inhibitory effect of K-80003 on AKT activation in PC3 cells. In comparison, a reduction of RARα expression by RARα siRNA did not show such an effect. Thus, inhibition of AKT activation by K-80003 was also dependent on RXRα expression (FIG. 8B).

Co-immunoprecipitation assays demonstrated that the interaction of RXRα/Δ80 with p85α either in the absence or presence of TNFα was potently inhibited by K-80003 as compared to the effect of Sulindac (FIG. 8C).

ZR-75-1 cells were treated with TNFα and/or Sulindac (75 μM) or K-80003 (50 μM) for 6 hr and analyzed by immunoblotting. K-80003 was also more effective than Sulindac in inducing PARP cleavage when used together with TNFα in ZR-75-1 cells (FIG. 8D). Similar to Sulindac, K-80003 in combination with TNFα synergistically induced PARP cleavage and caspase-8 activation in HepG2 and PC3 cells (FIG. 8E).

In clonogenic survival assays, colony formation of HeLa/RXRα/1-134 stable clone and RXRα/Δ80 stable clones was almost completely suppressed by K-80003, revealing its ability to inhibit cell growth (FIG. 8F). The inhibitory effect of K-80003 on AKT activation was abrogated by RXRα, but not RARγ siRNA (FIG. 8F), suggesting a role of RXRα in mediating its effects.

Mice (n=6) were treated intraperitoneally with corn oil, Sulindac (60 mg/kg), or K-80003 (60 mg/kg) for two weeks. Tumors were removed and measured. Significantly, K-80003 exhibited a much more potent inhibitory effect than Sulindac on the growth of RXRα/Δ80 tumor in animals (FIG. 8G). Together, the RXRα-selective Sulindac analog K-80003 is a potent inhibitor of RXRα-mediated PI3K/AKT signaling and cancer cell growth.

Example 10

Screening Sulindac Analogs in a Mammal

A panel of Sulindac analogs is selected to screen for a compound with the ability to induce apoptosis in cells. Each candidate compound is introduced to a mouse and analyzed to determine whether it is capable of suppressing the activity of AKT, activating caspase-8, activating BAX, inhibiting cFLIP, and/or degrading Bid in cells. Compounds identified during the screening can be used for further screening assays or methods of treatment as disclosed herein.

Example 11

Treating Cancer in a Human Patient

A human patient in need treatment for cancer is identified and administered a compound known to interact with RXRα and function independent of the COX-2 pathway. The patient is monitored for stabilization or improvement of cancer resulting from administration of the compound. An antitumorigenic effect is observed in the patient following administration of the compound.

Example 12

Preventing Cancer in a Human Patient

A human patient with an elevated risk of developing cancer relative to the general population is identified and instructed to take a 150 mg tablet containing the active ingredient K-80003 twice daily. The patient is monitored and does not develop cancer following administration of the compound.

Example 13

Sulindac Activation of TNFα-Induced Extrinsic Apoptotic Pathway

HepG2 cells cultured in medium with 1% FBS were treated with SR11237 (1 µM) for 1 hr, then TNFα (10 ng/ml) and/or Sulindac (75 µM) for 4 hr, and analyzed by immunoblotting. HepG2 cells transfected with control or RXRα siRNA were treated with TNFα and/or Sulindac and analyzed by immunoblotting.

Figure 16:
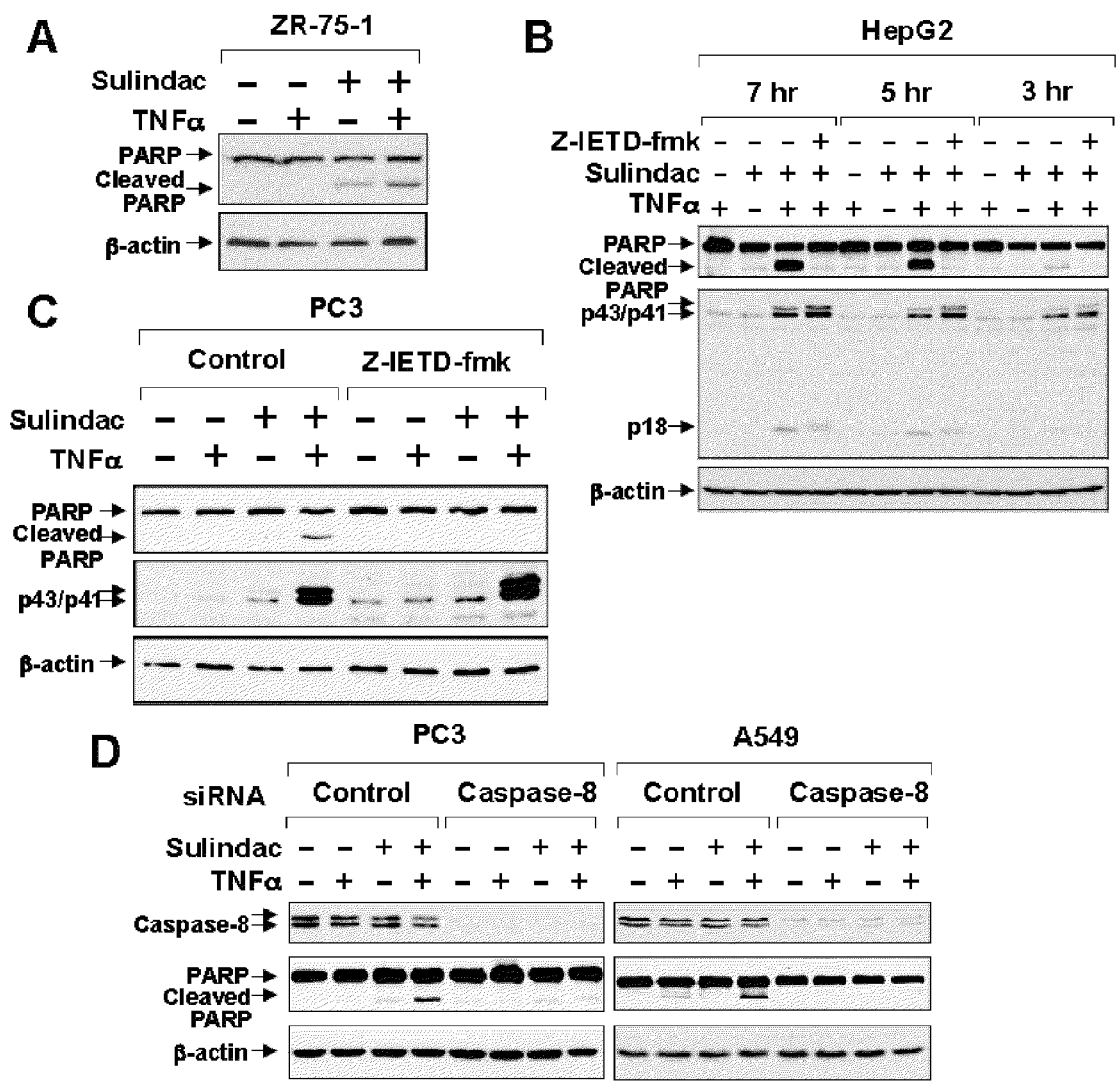
FIGS. 16A-D are related to FIG. 6 and show that Sulindac-induced apoptosis is mediated by a death receptor-dependent extrinsic apoptotic pathway.
Figure 17:
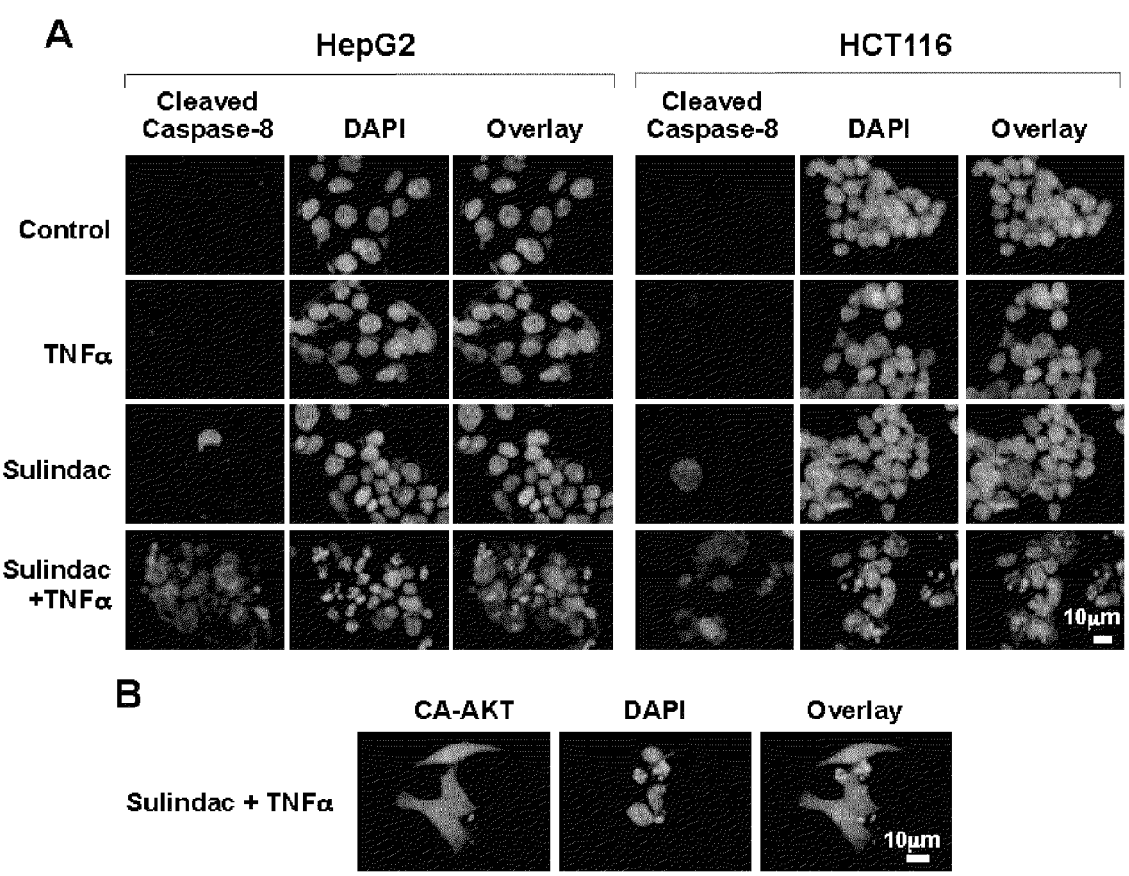
FIGS. 17A-B are related to FIG. 6 and show synergistic activation of caspase-8 by the Sulindac/TNFα combination in both HepG2 and HCT116 cancer cell lines, and shows that activation of AKT inhibits apoptosis induced by Sulindac/TNFα combination.

Treatment of HepG2 liver cancer cells (FIG. 6A) and other cancer cell lines (FIGS. 16 and 17) with Sulindac and TNFα effectively induced PARP cleavage and caspase-8 activation (indicated by cleaved caspase-8 products, p43/p41), while treatment of these cells with either Sulindac or TNFα alone had little effect. The apoptotic effect of Sulindac/TNFα combination was partially suppressed by RXRα-selective ligand SR11237 (FIG. 6A) or transfection of RXRα siRNA (FIG. 6B), again demonstrating a role for RXRα.

Figure 6:
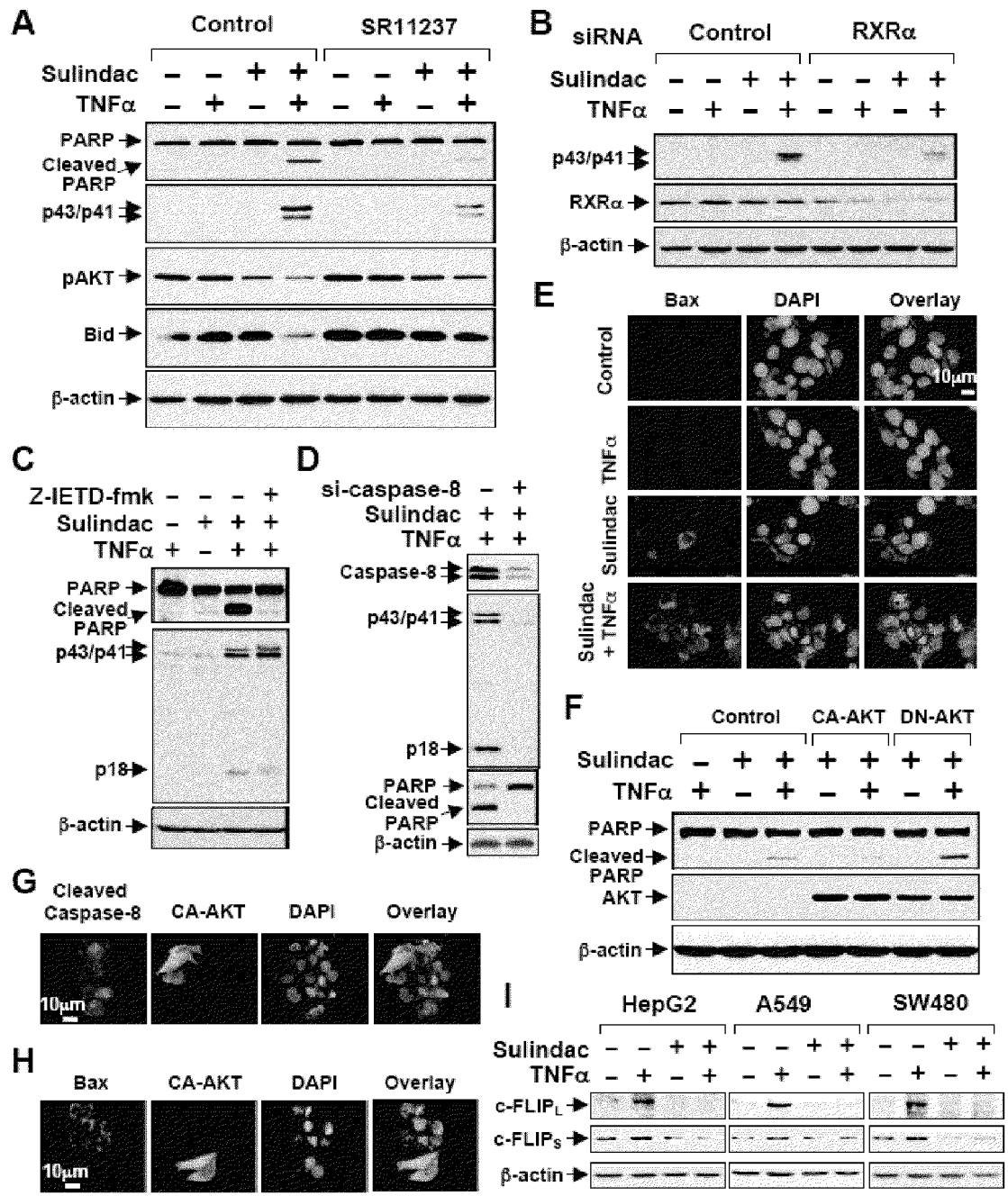
FIG. 6 shows the activation of a TNFα-induced extrinsic apoptotic pathway by Sulindac. (a) Synergistic induction of apoptosis by Sulindac/TNFα combination and its inhibition by RXRα ligand. HepG2 cells cultured in medium with 1% FBS were treated with SR11237, then TNFα and/or Sulindac, and analyzed by immunoblotting. (b) Inhibition of Sulindac/TNFα-induced caspase-8 cleavage by RXRα siRNA. HepG2 cells transfected with control or RXRα siRNA were treated with TNFα and/or Sulindac and analyzed by immunoblotting. Inhibition of Sulindac/TNFα-induced PARP cleavage by caspase-8 inhibitor (c) and siRNA (d). HepG2 cells transfected with control or caspase-8 siRNA or pretreated with ZIETD-fmk were treated with TNFα and Sulindac and analyzed by immunoblotting. (e) Activation of Bax by Sulindac and TNFα. HepG2 cells treated with TNFα and/or Sulindac were immunostained with Bax/6A7 antibody. (f) Regulation of Sulindac/TNFα-induced PARP cleavage by AKT. PC3 cells transfected with CA-AKT or DN-AKT were treated with TNFα and/or Sulindac, and analyzed by immunoblotting. Activation of caspase-8 (g) and Bax (h) by Sulindac and TNFα. HepG2 cells transfected with CA-AKT were treated with TNFα and Sulindac, and immunostained with anti-cleaved caspase-8 or Bax/6A7 antibody. (i) Regulation of c-FLIP expression by TNFα and Sulindac. Cells treated with TNFα and/or Sulindac were analyzed by immunoblotting.

HepG2 cells transfected with control or caspase-8 siRNA or pretreated with ZIETD-fmk (40 µM) for 1 hr were treated with TNFα and Sulindac and analyzed by immunoblotting. a complete suppression of Sulindac/TNFα-induced PARP cleavage (FIGS. 6C and 16B-C). Similar results were obtained when cells were transfected with Caspase-8 siRNA (FIGS. 6D and 16D). Thus, Sulindac/TNFα-induced apoptosis is mediated by the extrinsic apoptotic pathway.

Activation of Bax by Sulindac and TNFα HepG2 cells treated with TNFα and/or Sulindac were immunostained with Bax/6A7 antibody. About 15% Sulindac-treated cells while about 60% Sulindac/TNFα-treated cells showed Bax staining. Potential Sulindac activation of the extrinsic apoptotic pathway resulted in Bax activation was also examined. HepG2 cells treated with TNFα or Sulindac alone or together were examined for Bax activation by immunostaining using conformation-sensitive Bax/6A7 antibody. Significant Bax staining was observed only when cells were treated with both TNFα and Sulindac (FIG. 6E). Cross-talk between extrinsic and intrinsic apoptotic pathways can be linked through Bid cleavage and activation (Li et al., *Cell* 94 (4), 491-501 (1998)). Indeed, Bid was significantly degraded in cells treated with TNFα and Sulindac (FIG. 6A), suggesting that Sulindac/TNFα-induced Bax activation might be mediated through Bid activation.

PC3 cells transfected with CA-AKT or DN-AKT were treated with TNFα and/or Sulindac, and analyzed by immunoblotting (FIG. 6F). Activation of caspase-8 (FIG. 6G) and Bax (FIG. 6H) by Sulindac and TNFα HepG2 cells transfected with CA-AKT were treated with TNFα and Sulindac, and immunostained with anti-cleaved caspase-8 or Bax/6A7 antibody. About 80% nontransfected and 15% CA-AKT-transfected cells showed caspase-8 staining. About 60% nontransfected and about 13% CA-AKT-transfected cells exhibited Bax staining. Sulindac/TNFα-induced PARP cleavage was inhibited by transfection of constitutive-active AKT (CA-AKT) but enhanced by transfection of dominant-negative AKT (DN-AKT) (FIG. 6F). Consistently, induction of apoptosis (FIG. 17B) and activation of caspase-8 (FIG. 6G) and Bax (FIG. 6H) by Sulindac/TNFα combination was inhibited by CA-AKT.

Cells treated with TNFα and/or Sulindac for 6 hr were analyzed by immunoblotting (FIG. 6I). The expression of c-FLIP, a downstream target gene of AKT signaling, which acts as a potent inhibitor of the extrinsic apoptotic pathway by inhibiting caspase-8 activation, was examined. Treatment of HepG2, A549, and SW480 cells with TNFα resulted in strong induction of both short form (c-FLIPS) and long form (c-FLIPL) of c-FLIP, which was inhibited by Sulindac (FIG. 6I). Thus, Sulindac may induce apoptosis by suppressing the inducing effect of TNFα on c-FLIP expression.

Example 14

Growth Inhibition in Breast Tumor with K-80003

Figure 21:
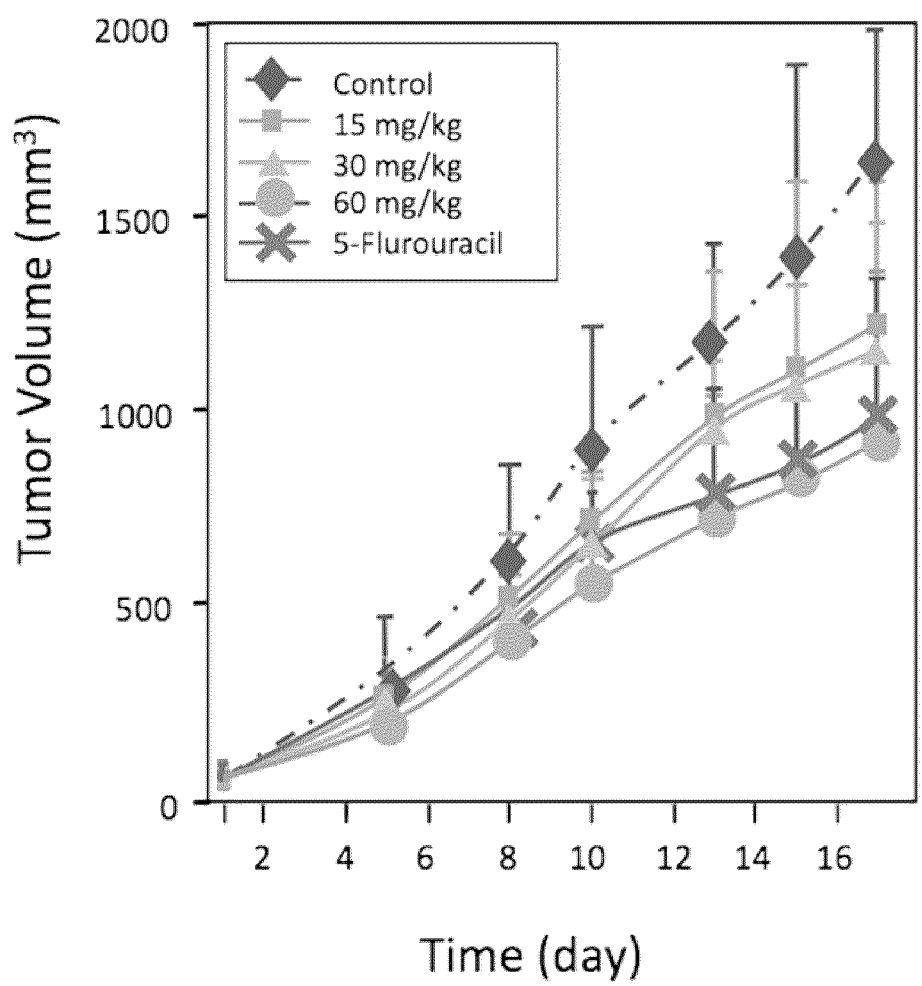
FIGS. 21A-C show the growth inhibitory effect of oral administration of K-80003 on MCF-7 breast tumor grown in mice. (A) Breast tumor volume over time in mice treated with oral K-80003 or a control. (B) Breast tumor tissue from mice treated with control. (C) Breast tumor tissue from mice treated with K-80003.

The growth inhibitory effect of oral administration of K-80003 on MCF-7 breast tumor tissue grown in mice was investigated. K-80003 was dissolved in NaHCO$_3$ (pH 8.0). Mice with MCF-7 breast tumor tissue were administered 15 mg/kg K-80003, 30 mg/kg K-80003, 60 mg/kg K-80003, or a control in 100 ul total volume by gavage once daily. Tumor volume measured over 20 days indicated that mice treated with oral K-80003 exhibited a dose-dependent decrease in tumor volume compared to mice treated with control (FIG. 21A).

Example 15

Preclinical Studies of K-80003

Figure 22:
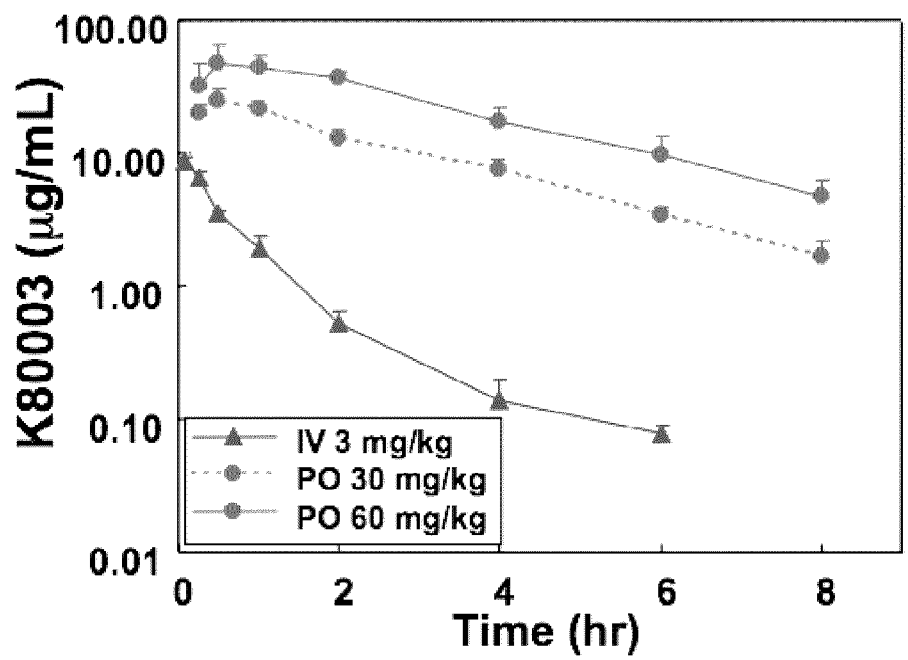
FIGS. 22A-C show toxicity and PK profiles for preclinical studies of K-80003. (A) Toxicity data. (B) Bioavailability data. (C) Pharmacokinetic data.

Preclinical studies of K-80003 were performed, including the investigation of toxicity, bioavailability, and pharmacokinetics. K-80003 exhibited very low toxicity (FIG. 22A), increased bioavailability in oral compared to intravenous formulation (FIG. 22B), and desirable PK profiles (FIG. 22C).

Example 16

Production of Analogs 3-(4-Fluorophenyl)-2-methylacrylic acid (2a)

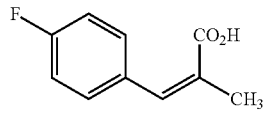

Propionic anhydride (31.0 mL, 242 mmol) was added to potassium carbonate (18.2 g, 132 mmol) at 0° C. After stirring for 5 min to mix up, p-fluorobenzaldehyde (1a) (13.0 mL, 120 mmol) was added. The mixture was heated at 160° C. for 12 h. After cooling with an ice bath, to the reaction mixture was added water. The resultant yellow precipitate was filtered, and washed with EtOAc to yield the crude acid 2a, which was used in the next step as it was. An analytical sample of the known acrylic acid 2a ((40) was obtained by recrystallization from MeOH. 2a: pale yellow crystals. M.p. 155-158° C. (MeOH). IR (KBr): $v_{max}$=3429, 3076, 2972, 1665, 1596, 1508, 1425, 1313, 1298, 1224 cm$^{-1}$; $^1$H NMR (400 MHz, CD$_3$OD) δ: 2.09 (s, 3H, CCH$_3$), 7.22-7.11 (m, 2H, Ph-H), 7.52-7.43 (m, 1H, Ph-H), 7.69 (s, 1H, CH=CCH$_3$) ppm; $^{13}$C NMR (100 MHz, CD$_3$OD) δ: 12.7, 114.8, 115.1, 131.4, 131.5, 132.1, 132.2, 137.5, 161.3, 163.75, 170.4 ppm; MS (ESI) m/z 179 (M-H$^+$).

3-(4-Fluorophenyl)-2-methylpropanoic acid (3a)

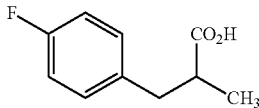

A mixture of the crude acrylic acid 2a (14.3 g, 79.4 mmol) and 10% Pd/C (1.35 g) in methanol (190 mL) was hydrogenated under 20 atm of hydrogen for 10 h. The catalyst was filtered off and the filtrate concentrated to give crude 3a, which was used in the next step as it was. An analytical sample of compound 3a (40) was obtained by flash column chromatography on silica gel (ethyl acetate:PE, 1:2). 3a: colorless oil. IR (film): $\nu_{max}$=3406, 2972, 2933, 1701, 1560, 1509, 1460, 1406, 1223 cm$^{-1}$; $^1$H NMR (400 MHz, CDCl$_3$) δ: 1.17 (d, J=6.82 Hz, 3H, CHCH$_3$), 2.77-2.61 (m, 2H, CH$_2$CH), 3.02 (dd, J=13.18, 6.35 Hz, 1H, CH$_2$CH), 7.00-6.93 (m, 2H, Ph-H), 7.16-7.11 (m, 2H, Ph-H) ppm; $^{13}$C NMR (100 MHz, CDCl$_3$) δ: 16.4, 38.4, 41.4, 115.1, 115.1, 130.3, 130.4, 134.5, 134.6, 160.4, 162.8, 182.6 ppm; MS (ESI) m/z 181 (M-H$^+$).

6-Fluoro-2-methyl-2,3-dihydroinden-1-one (4a)

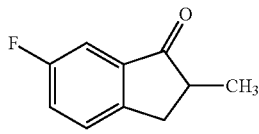

A mixture of the crude propanoic acid derivative 3a (3.20 g), and polyphosphoric acid (47.0 g) was heated at 80° C. for 4 hours. The resulting mixture was poured into ice water and extracted with EtOAc. The combined extracts were washed with a saturated aqueous NaHCO$_3$ to remove the starting acids, and then washed with brine, dried over anhydrous Na$_2$SO$_4$, filtered, and concentration under reduced pressure. The residue was purified by flash column chromatography (ethyl acetate:PE, 1:30) to give compound 4a (40) as a pale yellow oil (1.44 g, 50%). The NaHCO$_3$ layer was acidified with conc. HCl, extracted with EtOAc (3×30 mL). The combined extracts were washed with brine, dried over anhydrous Na$_2$SO$_4$, filtered and concentrated under reduced pressure to give the recovered starting material 3a (34%). The data for 4a: IR (film) $\nu_{max}$=3064, 2968, 2932, 2873, 1716, 1611, 1509, 1486, 1444, 1264, 1158 cm$^{-1}$; $^1$H NMR (400 MHz, CDCl$_3$) δ: 1.32 (d, J=7.37 Hz, 3H, CHCH$_3$), 2.82-2.65 (m, 2H, CH$_2$CH), 3.37 (dd, J=16.71, 7.55 Hz, 1H, CH$_2$CH), 7.33-7.26 (m, 1H, Ph-H), 7.44-7.36 (m, 2H, Ph-H) ppm; $^{13}$C NMR (100 MHz, CDCl$_3$) δ: 16.2, 34.4, 42.9, 76.3, 109.7, 109.9, 122.2, 122.5, 127.8, 127.9, 138.1, 148.8, 149.6, 161.1, 163.6, 208.5 ppm; MS (ESI) m/z 187 (M+Na$^+$).

Ethyl 2-(6-Fluoro-2-methyl-3H-inden-1-yl)acetate (5a)

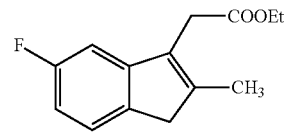 [SMILES: CCOC(=O)CC1=C(C)Cc2ccc(F)cc21]

To a solution of HMDS (15.0 mL, 56.9 mmol) in anhydrous THF (38.0 mL) at 0° C. was added dropwise n-BuLi (2.5 M solution in n-hexane, 17.0 mL, 42.8 mmol). After stirring for about 30 min, the mixture was cooled to −78° C. and was added EtOAc (4.20 mL, 42.8 mmol). The mixture was stirred at −78° C. for another 30 min. To the resulting mixture was added dropwise a solution of indenone 4a in anhydrous THF (40 mL). The mixture was stirred at −78° C. for another 4 h and then quenched with a saturated aqueous NH$_4$Cl. The mixture was extracted with EtOAc (3×20 mL). The combined organic layers were dried over anhydrous Na$_2$SO$_4$, filtered, and concentration under reduced pressure. To the residue was added HOAc/H$_2$SO$_4$ (10/1, 55 mL). After stirring for 5 hours at r.t., the mixture was extracted with CH$_2$Cl$_2$ (3×15 mL). The combined extracts were washed successively with water, saturated NaHCO$_3$, and brine, dried over Na$_2$SO$_4$, filtered, and concentrated under reduced pressure. The residue was purified by flash column chromatography on silica gel (ethyl acetate:PE, 1:30) to give compound 5a (40) as a colorless oil (3.26 g, 70%). IR (film) $\nu_{max}$=2981, 2911, 1736, 1614, 1590, 1473, 1368, 1329, 1308, 1256, 1154, 1034 cm$^{-1}$; $^1$H NMR (400 MHz, CDCl$_3$) δ: 1.25 (t, J=7.13 Hz, 3H, COOCH$_2$CH$_3$), 2.12 (s, 3H, CCH$_3$), 3.29 (s, 2H, PhCH$_2$C), 3.48 (s, 2H, PhCCH$_2$), 4.14 (q, J=7.13 Hz, 2H, COOCH$_2$CH$_3$), 6.79 (ddd, J=9.62, 8.12, 2.41 Hz, 1H, Ph-H), 6.96 (dd, J=9.33, 2.40 Hz, 1H, Ph-H), 7.25 (dd, J=8.17, 4.93 Hz, 1H, Ph-H) ppm; $^{13}$C NMR (100 MHz, CDCl$_3$) δ: 14.1, 14.3, 31.5, 42.1, 60.9, 105.6, 105.9, 110.2, 110.4, 123.6, 123.7, 129.6, 129.6, 137.2, 137.2, 144.6, 147.8, 147.9, 161.2, 163.6, 170.7 ppm; MS (ESI) m/z 257 (M+Na$^+$).

(Z)-2-(3-(4-(Methylthio)benzylidene)-6-fluoro-2-methyl-3H-inden-1-yl)acetic acid (Sulindac sulfide) (6a)

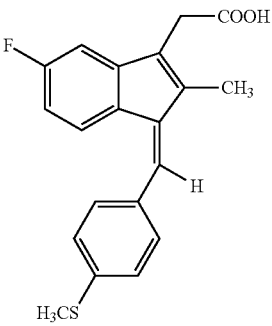

To a solution of indene 5a (650 mg, 3 mmol) in MeOH (4.6 mL) was added 2N NaOMe (4.6 mL, 9 mmol) at room temperature to get an orange mixture. After stirring for 20 min, to the mixture was added p-(methylthio)benzaldehyde (0.8 mL, 7.5 mmol). The resulting mixture was refluxed at 80° C. for 3.5 h. After concentration under reduced pressure, the residue was poured into a 1N HCl solution. After stirring for another 10 h at room temperature, the mixture was extracted with EtOAc (3×15 mL). The combined organic layers were dried over anhydrous $Na_2SO_4$, filtered, and concentrated under reduced pressure. The residue was purified by flash chromatography (ethyl acetate:PE, 1:2.5) to give predominantly the cis (Z) isomer 6a (Sulindac sulfide) (40) as a yellow solid (868 mg, 85%). The trans (E) isomer was obtained in about 2%. M.p. 182-185° C. (EtOAc) (lit. (40) M.p. 180-184° C.). IR (KBr) $v_{max}$=3445, 3012, 2914, 2850, 1702, 1602, 1589, 1465, 1410, 1320, 1240, 1171, 1085 cm$^{-1}$; $^1$H NMR (400 MHz, DMSO-d$_6$) δ: 2.15 (s, 3H, C=CCH$_3$), 2.54 (s, 3H, SCH$_3$), 3.57 (s, 2H, CH$_2$COO), 6.77-6.71 (m, 1H, vinyl H), 7.01 (dd, J=9.31, 2.25 Hz, 1H, vinyl H), 7.25-7.46 (m, 5H, Ph-H), 12.40 (s, 1H, COOH) ppm; $^{13}$C NMR (100 MHz, CDCl$_3$) δ: 10.7, 14.7, 31.5, 106.1, 106.4, 110.6, 110.8, 123.4, 123.5, 125.8, 130.0, 130.3, 131.0, 132.1, 132.6, 138.5, 139.5, 139.5, 139.5, 147.2, 147.3, 161.5, 161.6, 172.1 ppm; MS (ESI) m/z 331 (M+Na$^+$).

Following the procedure described for Sulindac sulfide (6a), and by condensation of indene 5a with an appropriate aromatic aldehyde, compounds K-80001 to K-80003 were synthesized, respectively.

(Z)-2-(3-(4-Methylbenzylidene)-6-fluoro-2-methyl-3H-inden-1-yl)acetic acid (6b) (K-80001)

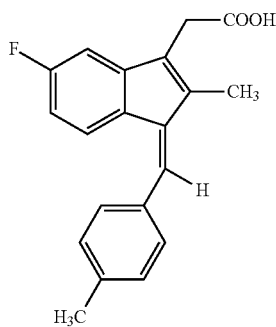 [SMILES: CC1=C(CC(=O)O)c2cc(F)ccc2/C1=C\c1ccc(C)cc1]

Yellow solid. M.p. 155-158° C. yield: 87%. IR (KBr) $v_{max}$=3426, 3022, 2959, 2915, 1733, 1717, 1655, 1599, 1512, 1470, 1408, 1381, 1214, 1172 cm$^{-1}$; $^1$H NMR (400 MHz, CDCl$_3$) δ: 2.19 (s, 3H, C=CCH$_3$), 2.41 (s, 3H, Ph-CH$_3$), 3.58 (s, 2H, CH$_2$CO$_2$H), 6.59-6.53 (m, 1H, vinyl H), 6.87 (dd, J=8.98, 2.40 Hz, 1H, vinyl H), 7.44-7.16 (m, 6H, Ph-H) ppm; $^{13}$C NMR (100 MHz, CDCl$_3$) δ: 10.61, 21.43, 29.73, 31.44, 105.54, 105.77, 110.48, 110.71, 123.73, 123.83, 129.21, 129.32, 129.78, 129.80, 129.84, 129.87, 131.00, 131.02, 133.48, 138.29, 138.95, 139.76, 146.13, 146.22, 161.84, 164.29, 176.68 ppm; MS (ESI) m/z 363 (M+Na$^+$). Anal. Calcd for $C_{20}H_{17}FO_2$: C, 77.90; H, 5.56. Found: C, 77.88; H, 5.99.

(Z)-2-(3-(4-Ethylbenzylidene)-6-fluoro-2-methyl-3H-inden-1-yl)acetic acid (6c) (K-80002)

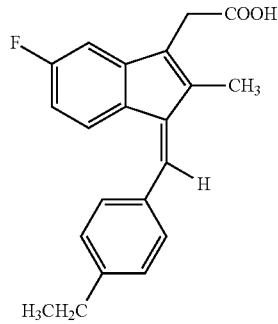

Yellow solid. M.p. 159-162° C. yield: 83%. IR (KBr) $v_{max}$=3082, 3024, 2965, 2923, 1705, 1604, 1473, 1465, 1413, 1312, 1229, 1168 cm$^{-1}$; $^1$H NMR (400 MHz, CDCl$_3$) δ: 1.29 (t, J=7.61 Hz, 3H, CH$_2$CH$_3$), 2.20 (s, 3H, C=CCH$_3$), 2.71 (q, J=7.60 Hz, 2H, CH$_2$CH$_3$), 3.59 (s, 2H, CH$_2$COO), 6.60-6.54 (m, 1H, aromatic vinyl H), 6.88 (dd, J=8.97, 2.39 Hz, 1H, aromatic vinyl H), 7.19-7.44 (m, 5H, Ph-H) ppm; $^{13}$C NMR (100 MHz, CDCl$_3$) δ: 10.6, 15.4, 28.7, 31.4, 105.5, 105.7, 110.5, 110.7, 123.7, 123.8, 128.0, 129.4, 129.7, 129.9, 131.0, 133.7, 138.9, 139.7, 144.6, 161.8, 164.2, 176.4 ppm; MS (ESI) m/z 345 (M+Na$^+$). Anal. Calcd for $C_{21}H_{19}FO_2$: C, 78.24; H, 5.94. Found: C, 78.21; H, 5.55.

(Z)-2-(3-(4-Iso-propylbenzylidene)-6-fluoro-2-methyl-3H-inden-1-yl)acetic acid (6d) (K-80003)

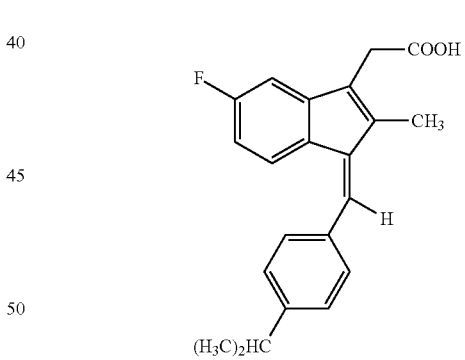

Yellow solid. M.p. 146-149° C.; yield: 79%. IR (KBr) $v_{max}$=3025, 2958, 2871, 1701, 1629, 1603, 1507, 1464, 1412, 1315, 1293, 1171, 1134 cm$^{-1}$; $^1$H NMR (400 MHz, CDCl$_3$) δ: 1.31 (d, J=6.95 Hz, 6H, CH(CH$_3$)$_2$), 2.20 (s, 3H, C=CCH$_3$), 2.97 (td, J=13.81, 6.91 Hz, 1H, CH(CH$_3$)2), 3.59 (s, 2H, CH$_2$COO), 6.61-6.88 (m, 2H, aromatic vinyl H), 7.19-7.46 (m, 6H, Ph-H); $^{13}$C NMR (100 MHz, CDCl$_3$) δ: 10.6, 23.9, 31.3, 34.0, 76.7, 105.5, 105.7, 110.5, 110.7, 123.7, 123.8, 126.5, 129.4, 129.7, 129.8, 131.0, 133.7, 139.0, 139.6, 146.1, 146.2, 149.3, 161.8, 164.2, 176.1 ppm; MS (ESI) m/z 359 (M+Na$^+$). Anal. Calcd for $C_{22}H_{21}FO_2$: C, 78.55; H, 6.29. Found: C, 78.13; H, 6.02.

Ethyl 2-(6-fluoro-3H-inden-1-yl)acetate (5b)

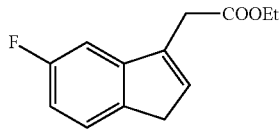 [SMILES: CCOC(=O)CC1=CCc2ccc(F)cc21]

To a solution of iso-propylamine (0.27 mL, 2 mmol) in anhydrous THF (4 mL) at 0° C. was added dropwise n-BuLi (2.5 M solution in n-hexane, 0.8 mL, 2 mmol). After stirring for about 30 min., the mixture was cooled to −78° C. and EtOAc (0.2 mL, 2 mmol) was added. After stirring at −78° C. for another 30 min., indenone 4b (150 mg, 1 mmol) in anhydrous THF (0.7 mL) was added dropwise. The mixture was stirred at −78° C. for another 2 h and then was quenched with saturated NH$_4$Cl. The mixture was extracted with EtOAc (3×5 mL). The combined organic layers were dried over anhydrous Na$_2$SO$_4$, filtered, and concentrated under reduced pressure. The residue was taken with AcOH/H$_2$SO$_4$ (10/1, 3 mL). After stirring for 3 h at r.t., the mixture was extracted with CH$_2$Cl$_2$ (3×5 mL). The combined extracts were washed successively with water, saturated NaHCO$_3$, and brine. The organic phase was dried over anhydrous Na$_2$SO$_4$, filtered, and concentrated under reduced pressure. The residue was purified by flash column chromatography on silica gel (ethyl acetate:PE, 1:30) to give 5b as a colorless oil (99 mg, 49%). IR (film) $v_{max}$=3054, 2982, 2931, 1704, 1636, 1486, 1446, 1369, 1345, 1288, 1276 cm$^{-1}$; $^1$H NMR (400 MHz, CDCl$_3$) δ: 1.28 (t, J=7.15 Hz, 3H, CH$_2$CH$_3$), 3.35 (s, 2H, CH$_2$CO$_2$Et), 3.56 (dd, J=2.93, 1.51 Hz, 2H, CH$_2$CH), 4.19 (q, J=7.15 Hz, 2H, CH$_3$CH$_2$), 6.52 (s, 1H, C=CH), 6.93-7.36 (m, 3H, Ph-H) ppm; $^{13}$C NMR (100 MHz, CDCl$_3$) δ: 14.2, 34.1, 37.4, 61.0, 106.4, 106.7, 111.4, 111.6, 124.3, 124.4, 134.1, 136.3, 136.4, 139.2, 139.3, 146.3, 146.4, 161.1, 163.5, 170.72 ppm. Anal. Calcd for C$_{13}$H=FO=: C, 70.90; H, 5.95. Found: C, 71.30; H, 6.23.

(E)-2-(3-(4-(Methylthio)benzylidene)-6-fluoro-3H-inden-1-yl)acetic acid (6e) (K-80004)

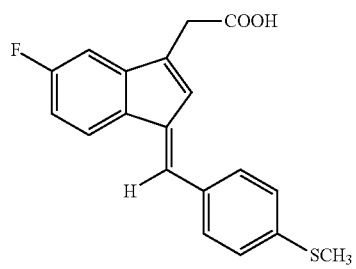 [SMILES: CSc1ccc(/C=C2\C=C(CC(=O)O)c3cc(F)ccc32)cc1]

To a solution of indene derivative 5b (506 mg, 2.50 mmol) in MeOH (4 mL) was added 2N NaOMe (4 mL, 4 mmol) at room temperature. After stirring for 20 min, to the resulting mixture was added p-(methylthio)benzaldehyde (0.65 mL, 2.50 mmol). The mixture was refluxed at 80° C. for 3.5 h. The resulting solution was concentrated under reduced pressure, and then poured into 1N HCl. After stirring for 10 hours at r.t., the mixture was extracted with EtOAc (3×10 mL). The combined organic layers were dried over anhydrous Na$_2$SO$_4$, filtered, and concentrated under reduced pressure. The residue was purified by flash column chromatography on silica gel (ethyl acetate:PE, 1:2.5) to give trans (E) isomer 6e (K-80004) as a yellow solid (429 mg, 48%). M.p. 180-182° C. (EtOAc). $^1$H NMR (400 MHz, CDCl$_3$) δ: 2.54 (s, 3H, SCH$_3$), 3.69 (s, 2H, CH$_2$COO), 7.09-7.84 (m, 9H, Ph-H), 12.52 (s, 1H, COOH) ppm; $^{13}$C NMR (100 MHz, CDCl$_3$) δ: 13.6, 115.5, 115.7, 127.3, 131.7, 131.8, 139.9, 161.5, 163.9, 174.0 ppm. Anal. Calcd for C$_{19}$H$_{15}$FO$_2$S: C, 69.92; H, 4.63; F, 5.82; 0, 9.80; S, 9.82. Found: C, 70.16; H, 4.92.

Spiro(dihydro-2(3H)furanone-5-1'(2'H)(3'H)-6-fluoro-indane (7a)

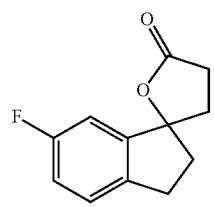 [SMILES: O=C1CCC2(CCc3ccc(F)cc32)O1]

A solution of 6-fluoro-1-indanone 4b (75.0 mg, 0.50 mmol), iso-propanol (0.190 mL, 2.50 mmol), and methyl acrylate (0.45 mL, 5 mmol) in THF (10 mL) was purged with argon for 20 min and cooled to 0° C. A SmI$_2$ (1.50 mmol) solution in THF (15 mL) was added through transfer needle. After 5 min, the reaction was quenched with sat. K$_2$CO$_3$ (2 mL). The resulting mixture was extracted with EtOAc (3×3 mL). The combined organic phases were washed with brine, dried over anhydrous Na$_2$SO$_4$, filtered and concentrated under reduced pressure. The residue was purified by flash column chromatography on silica gel eluting with EtOAc-PE (1:6) to give compound 7a (74.5 mg, 0.37 mmol, 73%) as a colorless oil; IR (film) $v_{max}$: 3058, 2945, 2856, 1766, 1603, 1494, 1155 cm$^{-1}$; $^1$H NMR (400 MHz, CDCl$_3$) δ: 2.28-2.52 (m, 4H, ArCCH$_2$), 2.77 (dt, J=8.0, 1.2 Hz, 2H, ArCCH$_2$CH$_2$CO), 2.81-2.90 (m, 1H, ArCH$_2$), 3.00-3.09 (m, 1H, ArCH$_2$), 6.96-7.03 (m, 2H, Ar—H), 7.18-7.23 (m, 1H, Ar—H); $^{13}$C NMR (100 MHz, CDCl$_3$) δ: 28.7, 29.5, 33.3, 39.4, 94.1, 109.7 (d, J$_{C-F}$=22.4 Hz) 116.6 (d, J$_{C-F}$=22.5 Hz), 126.2 (d, J$_{C-F}$=8.3 Hz), 138.8, 144.7 (d, J$_{C-F}$=7.4 Hz), 162.2 (d, J$_{C-F}$=233.5 Hz), 176.0 ppm; Anal. Calcd for C$_{12}$H$_{11}$FO$_2$: C, 69.89; H, 5.38. Found: C, 69.97; H, 5.62.

Methyl 3-(6-Fluoro-3H-inden-1-yl) propanoate (8a)

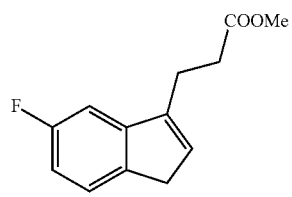 [SMILES: COC(=O)CCC1=CCc2ccc(F)cc21]

To a solution of spiro(dihydro-2(3H)furanone-5-1'(2'H)(3'H)-6-fluoro-indane 7a (61 mg, 3 mmol) in CH$_3$OH (1.5 mL) was added p-TsOH (6 mg). The mixture was refluxed for 2 hours. The reaction was quenched with a saturated aqueous solution of NaHCO₃ (2.0 mL). The resulting mixture was extracted with EtOAc (3×2 mL). The combined organic phases were washed with brine, dried over anhydrous Na₂SO₄, filtered and concentrated under reduced pressure. The residue was purified by flash column chromatography on silica gel eluting with EtOAc-PE (1:300) to give compound 8a (61 mg, 0.28 mmol, 94%) as a pale yellow oil. IR (film) $v_{max}$: 2959, 2901, 1739, 1585, 1606, 1473, 1254, 1162 cm⁻¹; ¹H NMR (400 MHz, CDCl₃) δ: 2.68-2.73 (m, 2H, CH₂COO), 2.82-2.88 (m, 2H, ArCCH₂), 3.28-3.31 (m, 2H, ArCH₂), 3.71 (s, 3H, COOCH₃), 6.30 (t, 1H, J=1.6 Hz, ArC=CH), 6.83-6.91 (m, 1H, Ar—H), 7.02-7.06 (m, 1H, Ar—H), 7.33-7.38 (m, 1H, Ar—H); ¹³C NMR (100 MHz, CDCl₃) δ: 22.9, 32.4, 37.3, 51.7, 106.0 (d, $J_{C-F}$=23.1 Hz), 111.4 (d, $J_{C-F}$=22.8 Hz), 124.4 (d, $J_{C-F}$=8.9 Hz), 130.3, 139.5, 142.4 (d, $J_{C-F}$=3.0 Hz), 146.9 (d, $J_{C-F}$=8.5 Hz), 162.4 (d, $J_{C-F}$=240.6 Hz), 173.4 ppm; Anal. Calcd for C₁₃H₁₃FO₂: C, 70.90; H, 5.95. Found: C, 70.50; H, 5.97.

(E)-Methyl 3-(3-(4-(methylthio)benzylidene)-6-fluoro-3H-inden-1-yl)propanoate (9a) (K-80005)

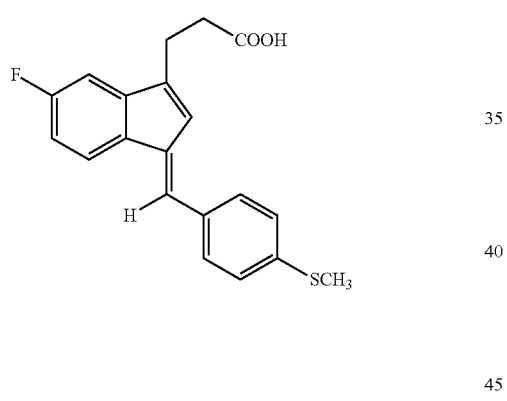

A solution of methyl 3-(6-fluoro-3H-inden-1-yl) propanoate 8a (110 mg, 0.5 mmol) in CH₃OH (1 mL) was purged with nitrogen for 10 min and cooled to 0° C. A freshly prepared CH₃ONa (0.75 mmol) in CH₃OH (1 mL) was added dropwise. After stirring for 30 min., 4-(methylthio)benzaldehyde (63 μL, 0.6 mmol) was added dropwise. The mixture was refluxed for 2 hours. After cooling, the reaction was quenched with water (3 mL) and stirred at room temperature for 10 min. The mixture was acidified with 1 M HCl to reach pH=4. The solvent was evaporated under reduced pressure, and the residue was extracted with EtOAc (3×5 mL). The combined organic layers were washed with brine (2 mL), dried over anhydrous Na₂SO₄, filtered and concentrated in vacuo. The residue was purified by flash column chromatography on silica gel eluting with EtOAc-PE (1:4) to give trans (E)-isomer 9a (112 mg, 66%) as a yellow solid. M.p.: 182-184° C. (EtOAc); IR (KBr) $v_{max}$: 3055, 2988, 2925, 1711, 1640, 1488, 1445, 1656, 1290, 1277 cm⁻¹; ¹H NMR (400 MHz, CDCl₃) δ: 2.53 (s, 3H, SCH₃), 2.68 (t, 2H, J=7.6 Hz, CH₂COO), 2.84 (t, 2H, J=7.6 Hz, ArCCH₂), 6.96-7.84 (m, 9H, Ar—H), 12.21 (s, COOH); ¹³C NMR (100 MHz, CDCl₃) δ: 14.3, 22.6, 32.0, 106.1 (d, $J_{C-F}$=23.4 Hz), 111.5 (d, $J_{C-F}$=23.0 Hz), 120.5 (d, $J_{C-F}$=9.2 Hz), 122.6, 125.8 (2C), 127.3, 130.4 (2C), 132.8, 134.1, 136.4, 139.4, 143.2 (d, $J_{C-F}$=8.8 Hz), 146.3, 162.2 (d, $J_{C-F}$=240.5 Hz), 173.8 ppm; Anal. Calcd for C₂₀H₁₇FO₂S: C, 70.57; H, 5.03; S, 9.42. Found: C, 70.20; H, 4.62; S, 9.01.

K-80003 Analog No. 1 (R1 Variant; Yellow Solid):

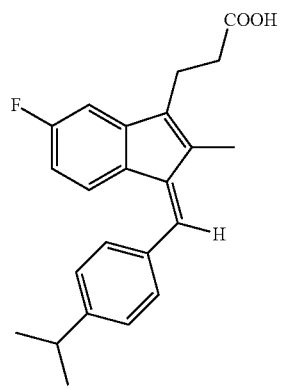 [SMILES: CC1=C(CCC(=O)O)c2cc(F)ccc2/C1=C\c1ccc(C(C)C)cc1]

K-80003 Analog No. 2 (R1 Variant; Yellow Solid):

K-80003 Analog No. 3 (R1 Variant; Yellow Solid):

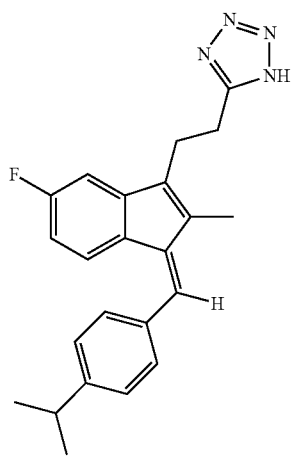 [SMILES: CC1=C(CCc2nnn[nH]2)c2cc(F)ccc2/C1=C\c1ccc(C(C)C)cc1]

K-80003 Analog No. 4 (R1 Variant; Yellow Solid):
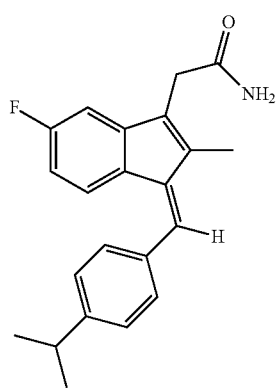 [SMILES: CC1=C(CC(N)=O)c2cc(F)ccc2/C1=C\c1ccc(C(C)C)cc1]
K-80003 Analog No. 5 (R1 Variant; Yellow Solid):
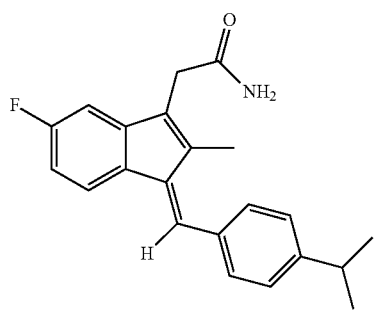 [SMILES: CC1=C(CC(N)=O)c2cc(F)ccc2/C1=C/c1ccc(C(C)C)cc1]
K-80003 Analog No. 6 (R1 Variant; Yellow Solid):
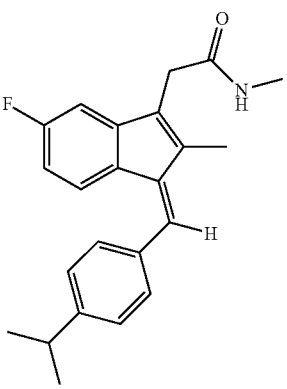 [SMILES: CNC(=O)CC1=C(C)/C(=C/c2ccc(C(C)C)cc2)c2ccc(F)cc21]
K-80003 Analog No. 7 (R1 Variant; Yellow Solid):
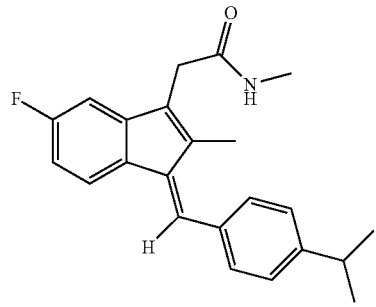 [SMILES: CNC(=O)CC1=C(C)/C(=C\c2ccc(C(C)C)cc2)c2ccc(F)cc21]
K-80003 Analog No. 8 (R2 Variant; Yellow Solid):
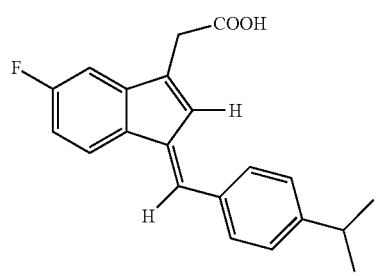 [SMILES: CC(C)c1ccc(/C=C2\C=C(CC(=O)O)c3cc(F)ccc32)cc1]
K-80003 Analog No. 9 (R2 Variant; Yellow Solid):
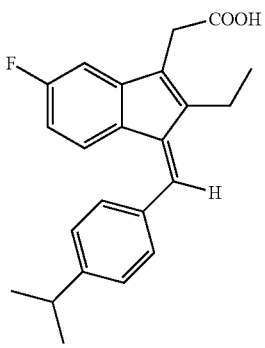 [SMILES: CCC1=C(CC(=O)O)c2cc(F)ccc2/C1=C\c1ccc(C(C)C)cc1]
K-80003 Analog No. 10 (R2 Variant; Yellow Solid):
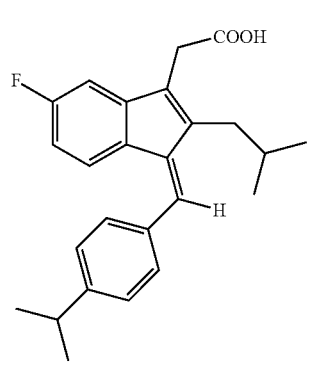 [SMILES: CC(C)CC1=C(CC(=O)O)c2cc(F)ccc2/C1=C\c1ccc(C(C)C)cc1]

K-80003 Analog No. 11 (R3 Variant; Yellow Solid):
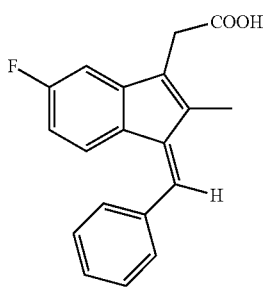 [SMILES: CC1=C(CC(=O)O)c2cc(F)ccc2/C1=C\c1ccccc1]
K-80003 Analog No. 12 (R3 Variant; Yellow Solid):
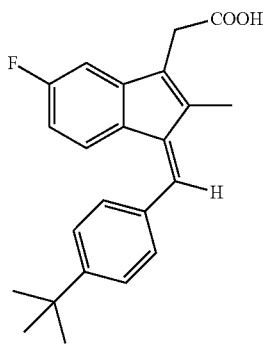 [SMILES: CC1=C(CC(=O)O)c2cc(F)ccc2/C1=C\c1ccc(C(C)(C)C)cc1]
K-80003 Analog No. 13 (R3 Variant; Yellow Solid):
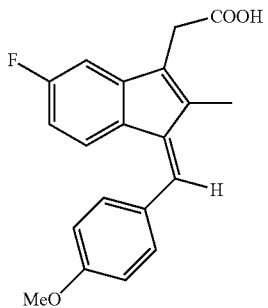 [SMILES: COc1ccc(/C=C2/C(C)=C(CC(=O)O)c3cc(F)ccc32)cc1]
K-80003 Analog No. 14 (R3 Variant; Yellow Solid):
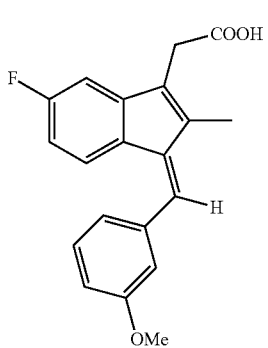 [SMILES: COc1cccc(/C=C2/C(C)=C(CC(=O)O)c3cc(F)ccc32)c1]
K-80003 Analog No. 15 (R3 Variant; Yellow Solid):
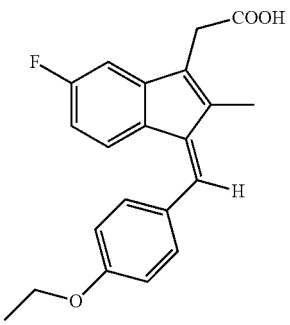 [SMILES: CCOc1ccc(/C=C2/C(C)=C(CC(=O)O)c3cc(F)ccc32)cc1]
K-80003 Analog No. 16 (R3 Variant; Yellow Solid):
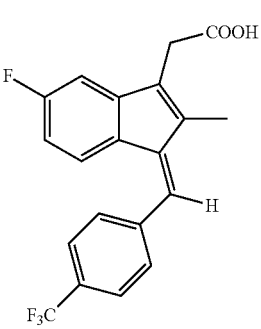 [SMILES: CC1=C(CC(=O)O)c2cc(F)ccc2/C1=C\c1ccc(C(F)(F)F)cc1]
K-80003 Analog No. 17 (R3 Variant; Yellow Solid):
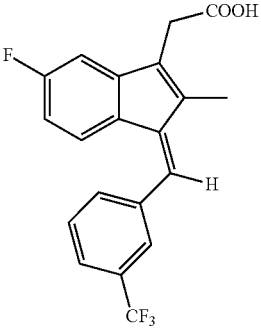 [SMILES: CC1=C(CC(=O)O)c2cc(F)ccc2/C1=C\c1cccc(C(F)(F)F)c1]
K-80003 Analog No. 18 (R3 Variant; Yellow Solid):
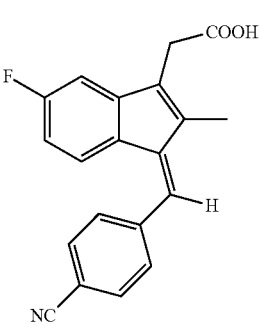 [SMILES: CC1=C(CC(=O)O)c2cc(F)ccc2/C1=C\c1ccc(C#N)cc1]

K-80003 Analog No. 19 (R3 Variant; Yellow Solid):
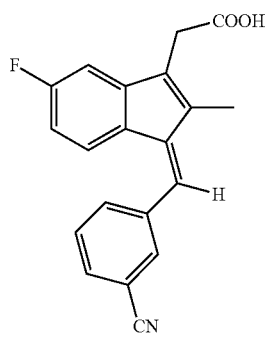 [SMILES: CC1=C(CC(=O)O)c2cc(F)ccc2/C1=C\c1cccc(C#N)c1]
K-80003 Analog No. 20 (R3 Variant; Yellow Solid):
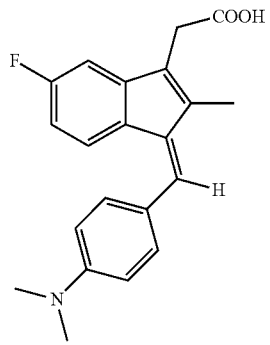 [SMILES: CC1=C(CC(=O)O)c2cc(F)ccc2/C1=C\c1ccc(N(C)C)cc1]
K-80003 Analog No. 21 (R3 Variant; Yellow Solid):
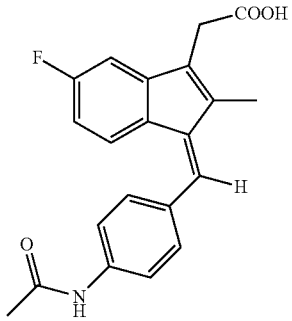 [SMILES: CC(=O)Nc1ccc(/C=C2/C(C)=C(CC(=O)O)c3cc(F)ccc32)cc1]
K-80003 Analog No. 22 (R4 Variant; Yellow Solid):
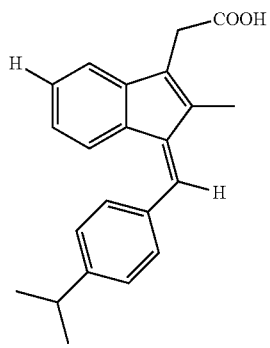 [SMILES: CC1=C(CC(=O)O)c2ccccc2/C1=C\c1ccc(C(C)C)cc1]
K-80003 Analog No. 23 (R4 Variant; Yellow Solid):
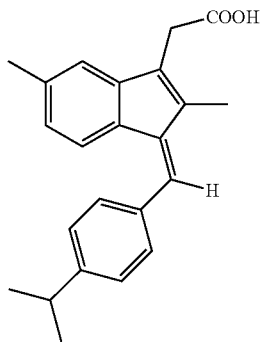
K-80003 Analog No. 24 (R4 Variant; Yellow Solid):
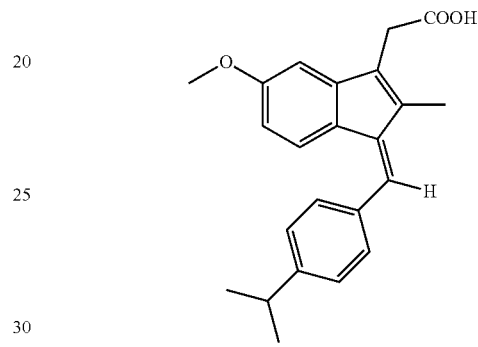
K-80003 Analog No. 25 (R1 Variant):
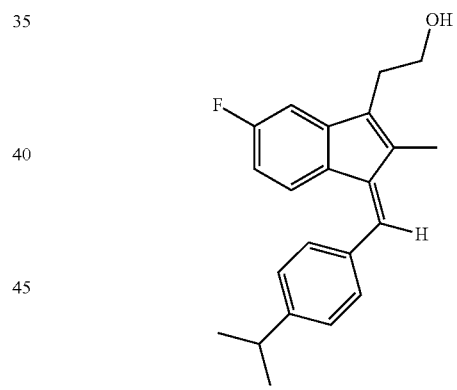
K-80003 Analog No. 26 (R1 Variant):
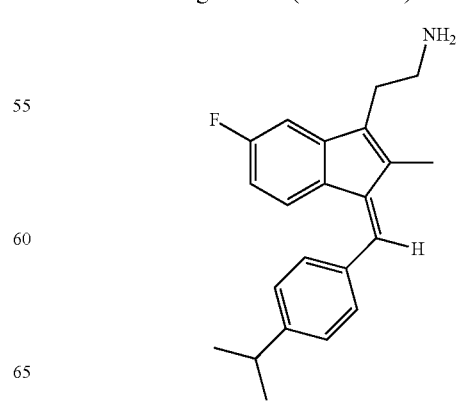

K-80003 Analog No. 27 (R3 Variant):
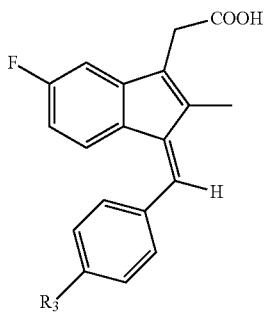
K-80003 Analog No. 28 (R3 Variant):
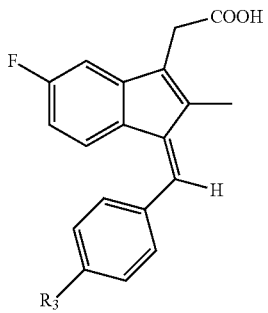
K-80003 Analog No. 29 (R3 Variant):
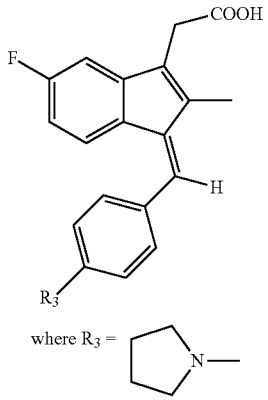
where $R_3$ =
K-80003 Analog No. 30 (R3 Variant):
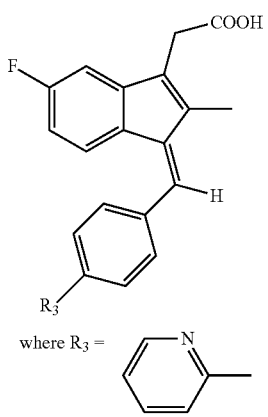
where $R_3$ =
K-80003 Analog No. 31 (R4 Variant):
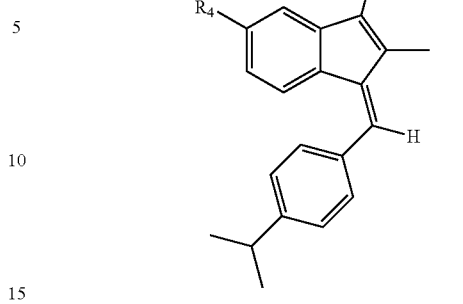
where $R_4$=Et.
K-80003 Analog No. 32 (R4 Variant):
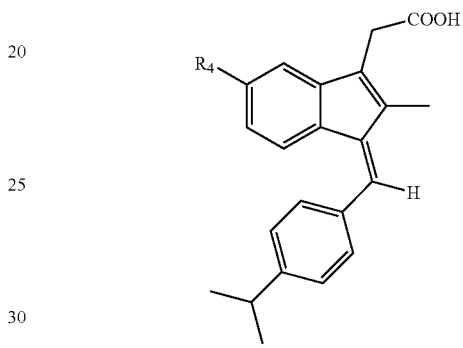
where $R_4$=EtO.
K-80003 Analog No. 33 (R4 Variant):
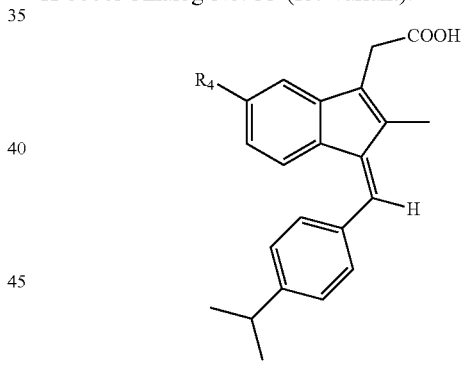
where $R_4$=i-Pr.
K-80003 Analog No. 34 (R4 Variant):
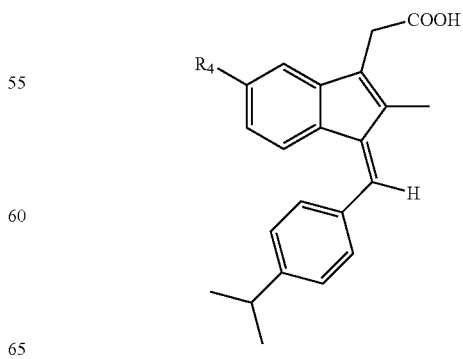
where $R_4$=Cl.

Summary of Methods

Plasmids

The construction of RXRα and Myc-RXRα has been described (Kolluri, S. K. et al., *Proc Natl Acad Sci* USA 102 (7), 2525-2530 (2005); Cao, X., et al., Retinoid X receptor regulates Nur77/TR3-dependent apoptosis [corrected] by modulating its nuclear export and mitochondrial targeting. *Mol Cell Biol* 24(22), 9705-9725 (2004); Masia, S. et al., Rapid, nongenomic actions of retinoic acid on phosphatidylinositol-3-kinase signaling pathway mediated by the retinoic acid receptor. *Mol Endocrinol* 21 (10), 2391-2402 (2007); Ohashi, E. et al., *Cancer Res* 69 (8), 3443-3450 (2009); Balkwill, F., *Nat Rev Cancer* 9 (5), 361-371 (2009); Han, Y. H. et al., *Oncogene* 25 (21), 2974-2986 (2006)). Flag-p85α was constructed by polymerase chain reaction (PCR) using forward primer, 5'-ccggaattccatgagtgctgagggg-tacc-3' (SEQ ID NO:1) and the reverse primer, 5'-acgcgtc-gactcatcgcctctgctgtgcat-3' (SEQ ID NO:2). PCR product was digested with Eco RI and Sal I and cloned into pCMV-Flag vector. RXRα mutants were constructed using the QUIKCHANGE® mutagenesis kit (Stratagene, La Jolla, Calif.) with the following oligonucleotides as primers: RXRα/F313S/R316E, 5'-GGAACGAGCTGCTGATCGC-CTCCTCCTCCCACGAGTCCATAGCTGT-GAAAGATGGG (forward—SEQ ID NO: 3) and 5'-CCCATCTTTCACAGCTATGGACTCGTGGGAG-GAGGAGGCGATCAGCAGCTCGTTCC (reverse—SEQ ID NO: 4); RXRα/A80, 5'-CCGGAATTCGGaccacacccac-cctgggc-3' (forward—SEQ ID NO: 5) and 5'-CCGCTC-GAGctaagtcatttggtgcggcg-3' (reverse—SEQ ID NO: 6); and RXRα/Δ100, 5'-CCGGAATTCGGgtcagcagcagcgaggac-3' (forward—SEQ ID NO: 5) and 5'-CCGCTCGAGctaagt-catttggtgcggcg-3' (reverse—SEQ ID NO: 6). PCR products were digested with EcoR I and Xho I, and ligated into pCMV-Myc vector.

Cell Culture

ZR-75-1 human breast cancer, LNCaP and PC3 prostate cancer, and H460 lung cancer cells were cultured in RPMI 1640 supplemented with 10% fetal bovine serum (FBS). HepG2 liver cancer and MCF-7 human cancer cells were maintained in MEM containing 10% FBS. HEK293T human embryonic kidney cells, CV-1 green monkey kidney cells, MEF cells, A549 human lung cancer cells, HaCat human keratinocyte cells, BHK baby hamster kidney cells, Caco2 human colon cancer carcinoma cells, SW480 human colon adenocarcinoma cells, and HCT116 human colon cells were maintained in DMEM supplemented with 10% FBS. The F9 murine embryonal carcinoma cell line had both alleles of RXRα disrupted (Clifford, J. et al., *Embo J* 15 (16), 4142-4155 (1996)). The cell cultures were maintained at 37° C. in a 5% $CO_2$ humidified atmosphere.

Antibodies and Reagents

Anti-phospho-Akt (Ser 473, D9E, #4060) was from Cell Signaling Technology (Danvers, Mass.). Anti-β-actin (A1978) and anti-Flag (M2, F3165) antibodies were obtained from Sigma-Aldrich (St. Louis, Mo.). Anti-p85α (#06-195) antibody was purchased from Millipore (Billerica, Mass.). Antibodies for Akt1(C-20) sc-1618, GFP (B-2) sc-9996, HSP60 (N-20) sc-1052, c-Myc (9E10) sc-40PI3, RARγ (C-19) sc-550, RXRα (D20) sc-553, RXRα (ΔN197) sc-774, PARP (H-250) sc-7150 were from Santa Cruz Biotechnology (Santa Cruz, Calif.). ECL, Anti-rabbit and anti-mouse IgG, Horseradish Peroxidase-Linked Species-Specific antibodies were from GE Healthcare (Little Chalfont, Buckinghamshire, UK). ALEXA FLUOR® 594 goat anti-rabbit IgG (A-11012) and ALEXA FLUOR® 488 goat anti-mouse IgG (A-10667) were purchased from Invitrogen (Carlsbad, Calif.). Protein A/G Plus-Agarose (sc-2003) was from Santa Cruz Biotechnology (Santa Cruz, Calif.). Recombinant Human TNFα (210-TA) was from R&D Systems (Minneapolis, Minn.). Protease Inhibitor Cocktail Tablets were from Roche (Basel, Switzerland). 9-cis-retinoic acid (9-cis-RA) (R4643). Sulindac sulfide and its analogues were dissolved in dimethyl sulfoxides (DMSO) in stock solutions of 100 mM. All-trans-retinoic acid (ATRA) (R2625) and chymotrypsin were from Sigma-Aldrich (St. Louis, Mo.). SR11237 was kindly provided by Dr. Marcia I. Dawson (Burnham Institute).

Ligand-Binding Assay

Bacterially expressed His-tagged RXRα ligand-binding domain (LBD) (aa 223-462) was incubated with $[^3H]$-9-cis-RA (Amersham Biosciences, Amersham, UK) in ligand binding assay buffer in the presence or absence of various concentrations of unlabeled 9-cis-RA or sulindac sulfide. The RXRα LBD protein was captured by nickel-coated beads. Bound radiolabeled 9-cis-RA was determined in a scintillation counter as described (Kolluri, S. K. et al., Proc Natl Acad Sci USA 102 (7), 2525-2530 (2005)).

HPLC Analysis of Sulindac Sulfide Binding to RXRα Protein in Cells

Expression vector containing receptor fused to C-terminal TAP fusion (Stratagene, La Jolla, Calif.) was transfected into HEK293 cells using FuGene 6 transfection reagent (Roche, Basel, Switzerland). The cells were maintained in exponential growth in complete medium, DMEM (Mediatech Inc., Herndon, Va.) supplemented with 10% calf serum (SCS, Hyclone Logan, Utah), 2 mM glutamine, penicillin (100 U/ml) and streptomycin (100 µg/ml). At two days post-transfection cells were switched into medium containing 400 mg/ml G418 until 20 days post-transfection, when dishes were scored for drug-resistant colonies. Expression of RXRα fusion protein was determined by immunoblotting. Cells were grown to confluency in four 150 mm plates and subsequently treated with or without 100 mM sulindac sulfide for 3 hr. After treatment, cells were twice washed in 50 ml cold PBS and streptavidin based purification carried out as described in INTERPLAY™ Mammalian TAP System (Stratagene, La Jolla, Calif.) manual up through initial wash of streptavidin beads with provided streptavidin binding buffer. A 0.1 ml portion of dilute sulfuric acid solution (pH 2) was then added followed by 1.0 ml of acetonitrile. The samples were then vortexed for 30 sec on a vortex mixer and subsequently centrifuged (1000 g×5 min). The liquid sample was then transferred to a second tube and evaporated to dryness under a stream of nitrogen. The residue was redissolved in 0.12 ml of chromatographic mobile phase, and a 0.1 ml portion was injected into the HPLC. HPLC analysis was performed using microsorb-mv 100-3 C18 100×4.6 column (Varian, Palo Alto, Calif.). The mobile phase consisted of 4% v/v aqueous acetic acid and acetonitrile (30:70) pumped at flow rate of 1.0 ml/min. Detection of sulindac sulfide was performed using a photoarray detector (Waters model 2996, Waters Corporation, Milford, Mass.), which collected spectra between 200 and 450 nM. A standard solution of sulindac sulfide was used to obtain the calibration curve. Characteristic peak spectrum and retention time was used for identification, and peak areas at 4max used for quantification were calculated by using MILLENNIUM CHROMATOGRAPHY MANAGER software (Waters Corporation, Milford, Mass.). One of three similar experiments was shown.

Proteolytic Protection Assay

RXRα LBD was synthesized by in vitro transcription-translation using rabbit reticulocyte lysates (Promega, Fitchburg, Wis.) as described previously (Kolluri, S. K. et al., Proc Natl Acad Sci USA 102 (7), 2525-2530 (2005); Zhang, X. K. et al., Nature 355 (6359), 441-446 (1992); Zhang, X.-K. et al., Nature. 358 (6387), 587-591 (1992)). In vitro translated $^{35}$[S]methionine labeled RXRα-LBD was preincubated with solvent (1% DMSO), Sulindac (100 µM) or 9-cis-RA ($10^{-7}$ M) for 30 min. and then digested with indicated concentration of chymotrypsin. Digested fragments were separated by PAGE.

Transient Transfection Assays

Cells ($1\times10^5$ cells/well) seeded in 24-well plates were transiently transfected using a modified calcium phosphate precipitation procedure as described (Kolluri, S. K. et al., Proc Natl Acad Sci USA 102 (7), 2525-2530 (2005); Cao, X., et al., Mol Cell Biol 24(22), 9705-9725 (2004)).

Apoptosis Assays

For nuclear morphological change analysis, cells were trypsinized, washed with PBS, fixed with 3.7% paraformaldehyde, and stained with DAPI (4,6-diamidino-2-phenylindole) (1 mg/ml) to visualize the nuclei by fluorescent microscopy (Masia, S. et al., Rapid, nongenomic actions of retinoic acid on phosphatidylinositol-3-kinase signaling pathway mediated by the retinoic acid receptor. Mol Endocrinol 21 (10), 2391-2402 (2007); Ohashi, E. et al., Cancer Res 69 (8), 3443-3450 (2009); Balkwill, F., Nat Rev Cancer 9 (5), 361-371 (2009)). The percentages of apoptotic cells were determined by counting at least 300 GFP-positive cells having nuclear fragmentation and/or chromatin condensation. For the determination of DNA fragmentation, the Cell Death Detection ELISA$^{PLUS}$ (Roche Applied Science, Penzberg, Bavaria, Germany) was used. One of three similar experiments was shown.

RXRα and RARγ siRNA

RXRα siRNA siGENOME SMARpool (M-003443-02), RARγ siRNA siGENOME SMARpool (M-003439-01), and siRNA Non-specific Control IX (D-001206-09-05) were purchased from DHARMACON (Lafayette, Colo.). A 2.5 µl aliquot of 20 mM siRNA/per well was transfected into cells grown in 12-well plates by using oligofectamine reagent (Invitrogen, Carlsbad, Calif.) according to manufacturer's recommendations. Two days after transfection the cells were harvested for Western blotting.

Immunoblotting

For immunoblotting, cell lysates were boiled in SDS sample buffer, resolved by SDS-polyacrylamide gel electrophoresis, and transferred to nitrocellulose. After transfer, the membranes were blocked in 5% milk in TBST (10 mM Tris-HCl, pH. 8.0, 150 mM NaCl, 0.05% Tween 20) containing antibody. The membranes were then washed three times with TBST, then incubated for 1 hr at room temperature in 5% milk in TBST containing horseradish peroxide-linked anti-immunoglobulin.

Coimmunoprecipitation (CoIP) Assays

For the CoIP assay, cells or cells transfected with indicated expression vectors were suspended in lysis buffer (50 mM Tris-HCl, pH 7.4; 150 mM NaCl; 20 mM EDTA; 1% NP-40; 1 mM PMSF; 50 mg/ml Leupeptin; 20 mg/ml Aprotinin; 0.1 mM Na$_3$VO$_4$; and 1 mM DTT). Cell extracts were cleared by incubation with the Protein A/G plus Agarose beads (Santa Cruz Biotechnology, Santa Cruz, Calif.) and then incubated with appropriate antibody and 30 ml of Protein A or G plus Agarose beads overnight at 4° C. Beads were then washed and boiled in Laemmli gel-loading solution before performing SDS-PAGE/immunoblotting using polyclonal or monoclonal antibodies. Immunoreactive products were detected by chemiluminescence with an enhanced chemiluminescence system (ECL™) (Amersham Biosciences, Amersham, UK).

HeLa-RXRα/1-134 Stable Clone and Soft Agar Assay

RXRα N-terminal fragment, 1-134, was cloned into pNTAP vector (Stratagene, La Jolla, Calif.). The resulting pNTAP-RXRα/1-134 was transfected into HeLa cells. 48 hr after transfection, cells were selected with 400 mg/ml G418 for 2 weeks. Single clones were picked up and examined by immunoblotting. HeLa RXR/α1-134 stable clone and HeLa cells transfected with control pNTAP vector were seeded at $5\times10^3$ cells/well (6 well plate) in DMEM supplemented with 10% FBS and 0.35% agarose with 0.5% bed agar. After 12 days incubation at 37° C., colonies were stained with 0.005% crystal violet for 1 h and counted.

Colony Formation Assay

HeLa RXR/α1-134 stable clone and control HeLa cells were seeded in 6-well plate, 350 cells/well. Five days later, cells were treated with Sulindac (50 µM) and K-80003 (25 µM) in 0.5% serum medium for 3 days. After washed with PBS, cells were fixed with 4% paraformaldehyde in PBS for 20 min. Colonies were stained with 0.1% crystal violet for 30 min, and pictures were taken and colonies were counted.

Human Tissues and Evaluation

Breast and liver tumor tissues and their surrounding tissues were obtained by surgical resection from cancer patients. Histological normal specimens, which were about at least 3~5 cm distant from the tumor nodule, were obtained from the corresponding patients. The study was approved by Xiamen University Institute for Biomedical Research Ethics Committee, and all of the patients gave informed consent.

Tissues from patients with primary hepatocellular carcinoma (HCC, n=6) or breast cancer (n=6) were collected for detecting the expression of RXRα. For the immunoblotting assay, tumor and its surrounding tissues were separately prepared and lysed in a modified RIPA buffer. The lysates were electrophoresed on an 8% SDS-PAGE gel and transferred onto PVDF membranes. The membranes were sequentially incubated with ΔN197 anti-RXRα antibody (1:1000) overnight at 4° C. and horseradish peroxidase conjugated anti-rabbit IgG antibody (1:5000) at room temperature for 1 hr, and detected by enhanced chemiluminescence (ECL™) (Amersham Biosciences, Amersham, UK). The stripped blots were reprobed with monoclonal anti-GAPDH antibody (1:2000) for loading control. For immunohistochemistry analysis, tissue sections were incubated with the ΔN197 anti-RXRα antibody (1:500) overnight at 4° C. and detected with goat antirabbit-specific immunoglobulins (1:100) at room temperature for 30 minutes. The slides were counterstained with hematoxylin.

Confocal Microscopy

Cells transfected with Myc-tagged RXRα/Δ80 and Flag-tagged p85α were seeded on chamber slides overnight. Cells were fixed in PBS containing 3.7% paraformaldehyde for 10 min and washed twice with PBS. Cells were then permeabilized with 0.1% triton X-100 in PBS for 5 min. Fixed cells were pre-incubated for 30 min in PBS containing 5% BSA at room temperature. Cells were stained with polyclonal anti-Myc antibody (1:500 dilution) and anti-Flag antibody (1:500 dilution) followed by Cy3-conjugated antirabbit IgG (1:1000, Sigma-Aldrich, St. Louis, Mo.) or FITC-labeled anti-mouse IgG (1:500, Sigma-Aldrich, St. Louis, Mo.). Confocal microscopy data shown in the manuscript are representative of at least three similar experiments.

Subcellular Fractionation

Subcellular fractionation was performed as described with minor modifications (Cao, X., et al., Mol Cell Biol 24(22), 9705-9725 (2004); Ohashi, E. et al., Cancer Res 69 (8), 3443-3450 (2009)).

Briefly, cells ($1\times10^7$ cells) suspended in 0.5 ml hypotonic buffer (250 mM sucrose, 20 mM HEPES-KOH, pH 7.4, 10 mM KCl, 10 mM $MgCl_2$, 0.5 mM EGTA, 1.5 mM EDTA, pH 8.0, and 1 mM DTT) with proteinase inhibitors were homogenized and cell extracts were centrifuged at 800×g for 10 min. The pellet containing nuclei was resuspended in 200 μl 1.6 M sucrose in hypotonic buffer plus protease inhibitors and laid over 1 ml 2.0 M sucrose in the same buffer, then centrifuged at 150,000×g for 90 min at 4° C. to obtain the nuclear fraction. The supernatant was centrifuged at 10,000×g for 30 min at 4° C. to obtain cytoplasmic fractions. Nuclear and cytoplasmic fractions were resuspended in 100 μl lysis buffer (10 mM Tris, pH 7.4, 150 mM NaCl, 1% Triton X-100, 5 mM EDTA, pH 8.0) with a cocktail of proteinase inhibitors for immunoblotting analysis.

COX Assays

COX Fluorescent Activity Assay Kit (700200), COX Fluorescent Inhibitor Screening Assay Kit (700100) and Prostaglandin E2 Enzyme Immunoassay (EIA) Kit (514010) were obtained from Cayman Chemical (Ann Arbor, Mich.). COX-1 and COX-2 activity assay were performed according to the manufacturer's protocol.

Chemical Synthesis

The $^1$H NMR and $^{13}$C NMR spectra were recorded on a Bruker AV 400 spectrometer (Bremen, Germany). $^1$H NMR spectra were registered in the indicated solvent, and chemical shifts are expressed in parts per million (δ) relative to internal $Me_4Si$. IR spectra were recorded on a Nicolet Avatar 360 FT-IR spectrophotometer (Thermo Fisher Scientific, Waltham, Mass.). Mass spectra were recorded with a Bruker Dalton Esquire 3000 plus (ESI direct injection) (Bremen, Germany). Elemental analyses were performed using a Vario RL analyzer. Melting points were determined on an X-4 Micromelting point apparatus and are uncorrected. The 6-fluoro-1-indanone 4b used in this study is commercially available. Tetrahydrofuran was distilled prior to use from sodium benzophenone ketyl. Dichloromethane was distilled from phosphorus pentoxide. Methanol was distilled from magnesium turnings and iodine. Silica gel (zhifu, 300-400 mesh) from Yantai Silica Gel Factory (China) was used for column chromatography, eluting (unless otherwise stated) with ethyl acetate/petroleum ether (PE) (60-90° C.) mixture or dichloromethane/methanol.

\* \* \* \* \*

While the present invention has been described in some detail for purposes of clarity and understanding, one skilled in the art will appreciate that various changes in form and detail can be made without departing from the true scope of the invention. All figures, tables, patents, patent applications and publications referred to herein are hereby incorporated by reference in their entireties.

---

What is claimed is:

1. A compound of formula (I), or a sodium salt thereof, having the structure:

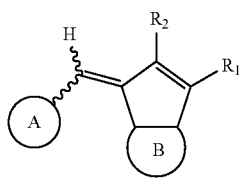

(I)

wherein A is a phenyl, and wherein A is substituted by one or two substituents independently selected from the group consisting of C2-3 alkyl, n-butyl, iso-butyl, sec-butyl, —CF$_3$, a C3-C4 cycloalkyl, and a C4-C5 cycloalkylalkyl;
wherein B is a fused phenyl, and wherein B is substituted by a fluoro;
wherein R$_1$ is —(CR$_5$R$_6$)$_n$COOH;
wherein R$_2$ is CH$_3$;
wherein R$_5$ and R$_6$ are H; and
wherein n is 1 or 2.

2. A compound of formula (II), or a sodium salt thereof, having the structure:

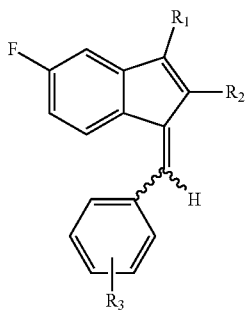

(II)

wherein R$_1$ is selected from the group consisting of CH$_2$COOH and CH$_2$CH$_2$COOH;
wherein R$_2$ is CH$_3$; and
wherein R$_3$ is selected from the group consisting of 4-CH$_2$CH$_3$, and 4-CH(CH$_3$)$_2$.

3. The compound of claim 2, or a sodium salt thereof, selected from the group consisting of:

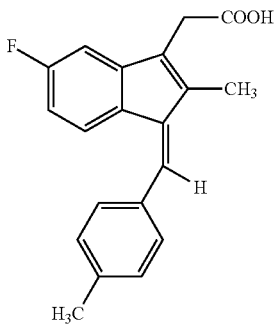

and

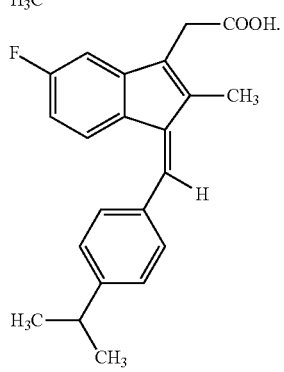

4. The compound of claim 2, or a sodium salt thereof, selected from the group consisting of:

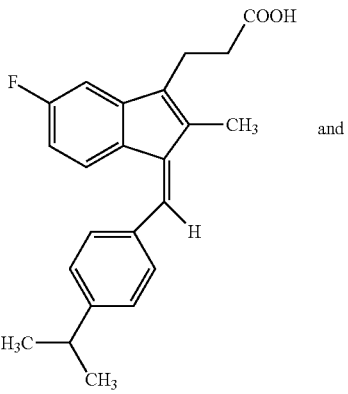

and

-continued

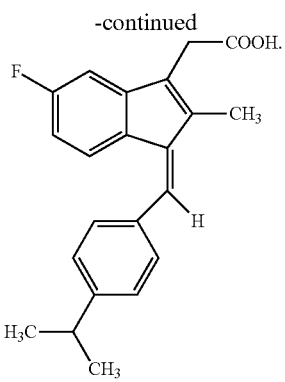

5. The compound of claim 2, or a sodium salt thereof, having the structure:

6. A compound, or a sodium salt thereof, having the structure:

7. A pharmaceutical composition comprising a compound of claim 1, or a sodium salt thereof, and a pharmaceutically acceptable excipient.

8. A pharmaceutical composition comprising a compound of claim 2, or a sodium salt thereof, and a pharmaceutically acceptable excipient.

9. A pharmaceutical composition comprising a compound of claim 6, or a sodium salt thereof, and a pharmaceutically acceptable excipient.

* * * * *